US012616690B2

(12) United States Patent
Khleif et al.

(10) Patent No.: US 12,616,690 B2
(45) **Date of Patent: *May 5, 2026**

(54) SPECIFIC AKT3 ACTIVATOR AND USES THEREOF

(71) Applicant: Augusta University Research Institute, Inc., Augusta, GA (US)

(72) Inventors: Samir Khleif, Silver Spring, MD (US); Mikayel Mkrtichyan, Tujunga, CA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/606,834

(22) Filed: Mar. 15, 2024

(65) Prior Publication Data

US 2025/0009735 A1 Jan. 9, 2025

Related U.S. Application Data

(63) Continuation of application No. 16/645,293, filed as application No. PCT/US2018/049715 on Sep. 6, 2018, now Pat. No. 11,957,673.

(60) Provisional application No. 62/555,141, filed on Sep. 7, 2017, provisional application No. 62/657,345, filed on Apr. 13, 2018, provisional application No. 62/659,870, filed on Apr. 19, 2018.

(51) Int. Cl.

| | |
|---|---|
| ***A61K 31/4709*** | (2006.01) |
| ***A61K 31/42*** | (2006.01) |
| ***A61K 31/436*** | (2006.01) |
| ***A61K 31/52*** | (2006.01) |
| ***A61K 31/5377*** | (2006.01) |
| ***A61K 31/573*** | (2006.01) |
| ***A61K 38/13*** | (2006.01) |
| ***A61K 38/17*** | (2006.01) |
| ***A61K 39/395*** | (2006.01) |
| ***A61K 40/11*** | (2025.01) |
| ***A61K 40/22*** | (2025.01) |
| ***A61K 40/41*** | (2025.01) |
| ***A61K 40/42*** | (2025.01) |
| ***A61P 37/06*** | (2006.01) |
| ***C07D 401/12*** | (2006.01) |

(52) U.S. Cl.

CPC .......... *A61K 31/4709* (2013.01); *A61K 31/42* (2013.01); *A61K 31/436* (2013.01); *A61K 31/52* (2013.01); *A61K 31/5377* (2013.01); *A61K 31/573* (2013.01); *A61K 38/13* (2013.01); *A61K 38/1774* (2013.01); *A61K 38/1793* (2013.01); *A61K 39/3955* (2013.01); *A61K 40/11* (2025.01); *A61K 40/22* (2025.01); *A61K 40/416* (2025.01); *A61K 40/42* (2025.01); *A61K 40/4242* (2025.01); *A61P 37/06* (2018.01); *C07D 401/12* (2013.01)

(58) Field of Classification Search

CPC .......................... C07D 401/12; A61K 31/4709

See application file for complete search history.

(56) References Cited

U.S. PATENT DOCUMENTS

| | | | |
|---|---|---|---|
| 3,987,102 A | 10/1976 | Karrer | |
| 5,190,929 A | 3/1993 | Borch et al. | |
| 6,387,051 B1 | 5/2002 | Ragauskas et al. | |
| 6,395,876 B1 | 5/2002 | Munn et al. | |
| 6,451,840 B1 | 9/2002 | Munn et al. | |
| 6,809,194 B1 | 10/2004 | Reinhard et al. | |
| 6,949,535 B2 | 9/2005 | Sadhu et al. | |
| 7,790,746 B2 | 9/2010 | Phiasivongsa et al. | |
| 7,939,546 B2 | 5/2011 | Phiasivongsa et al. | |
| 8,535,656 B2 | 9/2013 | Banks et al. | |
| 8,546,082 B2 | 10/2013 | Hall et al. | |
| RE44,599 E | 11/2013 | Fowler et al. | |
| 8,672,851 B1 | 3/2014 | Quirk et al. | |
| 9,101,573 B2 | 8/2015 | Bassaganya-Riera et al. | |
| 9,398,861 B2 | 7/2016 | Bellezza et al. | |
| 9,606,120 B2 | 3/2017 | Bettsworth et al. | |
| 9,707,278 B2 | 7/2017 | Khleif et al. | |
| 10,159,731 B2 | 12/2018 | Khleif et al. | |
| 10,292,978 B2 | 5/2019 | Khleif et al. | |
| 10,342,868 B2 | 7/2019 | Khleif et al. | |
| 10,525,049 B2 | 1/2020 | Khleif et al. | |
| 10,588,966 B2 | 3/2020 | Khleif et al. | |
| 10,980,878 B2 | 4/2021 | Khleif et al. | |
| 11,013,735 B2 | 5/2021 | Khleif et al. | |
| 11,291,719 B2 | 4/2022 | Khleif et al. | |
| 11,957,673 B2 * | 4/2024 | Khleif | A61K 38/13 |
| 2004/0106634 A1 | 6/2004 | Satoh et al. | |

(Continued)

FOREIGN PATENT DOCUMENTS

| | | |
|---|---|---|
| AU | 2018329840 A1 | 3/2020 |
| BR | 112020003494 A2 | 8/2020 |
| CA | 3074641 A1 | 3/2019 |
| CL | 200502832 A1 | 6/2006 |
| CL | 2011003297 A1 | 6/2012 |
| CL | 2020000127 A1 | 4/2020 |
| CL | 2020000363 A1 | 6/2020 |

(Continued)

OTHER PUBLICATIONS

Abu Eid, et al., AKT inhibition mitigates terminal differentiation and preserves central memory phenotype of CD8 T cells, J Immunother Cancer., vol. 2 (Suppl 3): P93, 2014, 1 page.

(Continued)

*Primary Examiner* — Paul V Ward

(74) *Attorney, Agent, or Firm* — PABST PATENT GROUP LLP

(57) ABSTRACT

Compositions and methods of selectively activating Akt3 are provided.

32 Claims, 34 Drawing Sheets

Specification includes a Sequence Listing.

(56) References Cited

U.S. PATENT DOCUMENTS

| | | | |
|---|---|---|---|
| 2006/0142178 | A1 | 6/2006 | Barnett et al. |
| 2007/0142440 | A1 | 6/2007 | Burgdorf et al. |
| 2007/0202077 | A1 | 8/2007 | Brodsky et al. |
| 2008/0175814 | A1 | 7/2008 | Phiasivongsa et al. |
| 2009/0099106 | A1 | 4/2009 | Phiasivongsa et al. |
| 2009/0285772 | A1 | 11/2009 | Phiasivongsa et al. |
| 2010/0063130 | A1 | 3/2010 | Tsubata et al. |
| 2010/0135900 | A1 | 6/2010 | Cerveny et al. |
| 2011/0135655 | A1 | 6/2011 | Katsikis et al. |
| 2012/0010229 | A1 | 1/2012 | Macdougall et al. |
| 2013/0150684 | A1 | 6/2013 | Cooner |
| 2015/0051489 | A1 | 2/2015 | Caluser et al. |
| 2016/0000367 | A1 | 1/2016 | Lyon |
| 2016/0051669 | A1 | 2/2016 | Khleif et al. |
| 2017/0202829 | A1 | 7/2017 | Khleif et al. |
| 2017/0202956 | A1 | 7/2017 | Khleif et al. |
| 2017/0216355 | A1 | 8/2017 | Khleif et al. |
| 2018/0271870 | A1 | 9/2018 | Khleif et al. |
| 2020/0046692 | A1 | 2/2020 | Khleif et al. |
| 2020/0077906 | A1 | 3/2020 | Lyon |
| 2020/0109365 | A1 | 4/2020 | Friedman |
| 2020/0164067 | A1 | 5/2020 | Khleif et al. |
| 2020/0390884 | A1 | 12/2020 | Khleif et al. |
| 2021/0006313 | A1 | 1/2021 | Rune et al. |
| 2021/0113550 | A1 | 4/2021 | Khleif et al. |
| 2021/0196817 | A1 | 7/2021 | Khleif et al. |
| 2023/0201188 | A1 | 6/2023 | Khleif |
| 2024/0316190 | A1 | 9/2024 | Khleif et al. |

FOREIGN PATENT DOCUMENTS

| | | | |
|---|---|---|---|
| CL | 2020000376 | A1 | 8/2020 |
| CL | 2020000553 | A1 | 8/2020 |
| CL | 2020002073 | A1 | 12/2020 |
| CL | 2020002082 | A1 | 12/2020 |
| CL | 2020002943 | A1 | 3/2021 |
| CN | 111093663 | A | 5/2020 |
| CO | 2020003120 | A2 | 4/2020 |
| EP | 3678666 | A1 | 7/2020 |
| IL | 272909 | A | 4/2020 |
| JP | S5018628 | A | 2/1975 |
| JP | H01113369 | A | 5/1989 |
| JP | 2006521394 | A | 9/2006 |
| JP | 2007536280 | A | 12/2007 |
| JP | 2010506856 | A | 3/2010 |
| JP | 2010521487 | A | 6/2010 |
| JP | 2016535755 | A | 11/2016 |
| JP | 2020533317 | A | 11/2020 |
| KR | 20200052304 | A | 5/2020 |
| MX | 2020002611 | A | 7/2020 |
| RU | 2421454 | C2 | 6/2011 |
| RU | 2487121 | C2 | 7/2013 |
| RU | 2579513 | C2 | 4/2016 |
| WO | 2004084933 | A1 | 10/2004 |
| WO | 2005113494 | A2 | 12/2005 |
| WO | 2006048146 | A1 | 5/2006 |
| WO | 2008046085 | A2 | 4/2008 |
| WO | 2008112913 | A1 | 9/2008 |
| WO | 2008147482 | A2 | 12/2008 |
| WO | 2010151791 | A1 | 12/2010 |
| WO | 2012037204 | A1 | 3/2012 |
| WO | 2015069594 | A1 | 5/2015 |
| WO | 2015188119 | A1 | 12/2015 |
| WO | 2016109665 | A1 | 7/2016 |
| WO | 2019051063 | A1 | 3/2019 |

OTHER PUBLICATIONS

Abu-Eid, et al., Akt1 and -2 inhibition diminishes terminal differentiation and enhances central memory CD8+ T-cell proliferation and survival, Oncoimmunology., vol. 4, No. 5: e1005448, May 2015.

Abu-Eid, et al., Selective inhibition of regulatory T cells by targeting the PI3K-Akt pathway, Cancer Immunol Res., vol. 2, No. 11, Nov. 2014, pp. 1080-1089.

Advisory Action received for U.S. Appl. No. 15/540,455, mailed on Oct. 7, 2020, 3 pages.

Advisory Action received for U.S. Appl. No. 15/407,659, mailed on Oct. 5, 2018.

Ahmad, et al., Functional redundancy of PI3K isoforms in conventional T cells provides a selective Treg-targeting strategy through inhibition of PI3K-delta isoform, J. Immunother Cancer., vol. 2(Suppl 3): O4, 2014.

Ali, et al., Inactivation of PI(3)K p110δ breaks regulatory T-cell-mediated immune tolerance to cancer, Nature, vol. 510, No. 7505, Jun. 19, 2014, pp. 407-411.

Ali, et al., Synthesis and structure-activity relationship studies of HIV-1 virion infectivity factor (Vif) inhibitors that block viral replication, ChemMedChem., vol. 7, No. 7, Jul. 2012, pp. 1217-1229.

Araki, et al., mTOR regulates memory CD8 T-cell differentiation, Nature, vol. 460, 2009, pp. 108-112.

Atwell, et al., Potential antitumor agents. 13. Bisquaternary salts, J Med Chem., vol. 16, No. 6, Jun. 1973, pp. 673-678.

Atwell, et al., Potential antitumor agents. 15. Bisquaternary salts, J Med Chem., vol. 17, No. 9, Sep. 1974, pp. 930-934.

Bach, Jean-Francois, The effect of infections on susceptibility to autoimmune and allergic diseases, N Engl J Med., vol. 347, No. 12, Sep. 19, 2002, pp. 911-920.

Barka, et al., Transduction of TAT-HA-beta-galactosidase fusion protein into salivary gland-derived cells and organ cultures of the developing gland, and into rat submandibular gland in vivo, J Histochem Cytochem, vol. 48, No. 11, Nov. 2000, pp. 1453-1460.

Basu, et al., Cutting edge: Foxp3-mediated induction of pim 2 allows human T regulatory cells to preferentially expand in rapamycin, J Immunol., vol. 180, No. 9, May 1, 2008, pp. 5794-5798.

Battaglia, et al., Rapamycin selectively expands CD4+CD25+ FoxP3+ regulatory T cells, Blood, vol. 105, No. 12, Jun. 15, 2005, pp. 4743-4748.

Bell, et al., Targeting RNA-protein interactions within the human immunodeficiency virus type 1 lifecycle, Biochemistry, vol. 52, No. 51, Dec. 23, 2013, pp. 9269-9274.

Bernstein, et al., Role for a bidentate ribonuclease in the initiation step of RNA interference, Nature, vol. 409, No. 6818, Jan. 18, 2001, pp. 363-366.

Bluestone, et al., Natural versus adaptive regulatory T cells, Nat Rev Immunol., vol. 3, No. 3, Mar. 2003, pp. 253-257.

Boland, et al., Mapping of Deletion and Translocation Breakpoints in 1944 Implicates the Serine/Threonine Kinase AKT3 in Postnatal Microcephaly and Agenesis of the Corpus Callosum, Am J Hum Genet., vol. 81, No. 2, Aug. 2007, pp. 292-303.

Braithwaite, et al., Existence of an extended series of antitumor compounds which bind to deoxyribonucleic acid by nonintercalative means, Biochemistry, vol. 19, No. 6, Mar. 18, 1980, pp. 1101-1106.

Brana, et al., A parallel-arm phase I trial of the humanised anti-IGF-1R antibody dalotuzumab in combination with the AKT inhibitor MK-2206, the mTOR inhibitor ridaforolimus, or the NOTCH inhibitor MK-0752, in patients with advanced solid tumours, Br J Cancer, vol. 111, No. 10, Nov. 11, 2014, pp. 1932-1944.

Cain, et al., Potential antitumour agents. 11. 9-anilinoacridines, J Med Chem., vol. 14, No. 4, Apr. 1971, pp. 311-315.

Carbone, et al., EBV-Associated Lymphoproliferative Disorders: Classification and Treatment, The Oncologist, vol. 13, No. 5, May 2008, pp. 577-585.

Carson, et al., Impaired T cell receptor signaling in Foxp3+ CD4 T cells, Ann N Y Acad Sci., vol. 1103, Apr. 2007, pp. 167-178.

Chen, et al., Conversion of Peripheral CD4+CD25- Naive T Cells to CD4+CD25+ Regulatory T Cells by TGF-β Induction of Transcription Factor Foxp3, J Exp Med., vol. 198, No. 12, Dec. 15, 2003, pp. 1875-1886.

Communication pursuant to Rules 70(2) and 70a(2) EPC Received for EP Application No. 18854685, mailed on May 26, 2021, 1 page.

Conery, et al., Akt interacts directly with Smad3 to regulate the sensitivity to TGF-beta induced apoptosis, Nat Cell Biol., vol. 6, No. 4, Apr. 2004, pp. 366-372.

(56) References Cited

OTHER PUBLICATIONS

Covey, et al., Topoisomerase II-mediated DNA damage produced by 4'-(9-acridinylamino)methanesulfon-m-anisidide and related acridines in L1210 cells and isolated nuclei: relation to cytotoxicity, Cancer Res., vol. 48, No. 4, Feb. 15, 1988, pp. 860-865.
Crellin, et al., Altered activation of AKT is required for the suppressive function of human CD4+CD25+ T regulatory cells, Blood, vol. 109, No. 5, Mar. 1, 2007, pp. 2014-2022.
Crellin, et al., Flow cytometry-based methods for studying signaling in human CD4+CD25+FOXP3+ T regulatory cells, J Immunol Methods, vol. 324, No. 1-2, Jul. 31, 2007, pp. 92-104.
Crompton, et al., Akt inhibition enhances expansion of potent tumor-specific lymphocytes with memory cell characteristics, Cancer Res., vol. 75, No. 2, Jan. 15, 2015, pp. 296-305.
Dannull, et al., Enhancement of vaccine-mediated antitumor immunity in cancer patients after depletion of regulatory T cells, J Clin Invest., vol. 115, No. 12, Dec. 1, 2005, pp. 3623-3633.
Debosch, et al., Akt2 regulates cardiac metabolism and cardiomyocyte survival, J Biol Chem., vol. 281, No. 43, Oct. 27, 2006, pp. 32841-32851.
Denisova, et al., Akt Inhibitor MK2206 Prevents Influenza pH1N1 Virus Infection In Vitro, Antimicrob Agents Chemother., vol. 58, No. 7, Jul. 2014, pp. 3689-3696.
Denny, et al., Potential antitumor agents. 29. Quantitative structure-activity relationships for the antileukemic bisquaternary ammonium heterocycles, J Med Chem., vol. 22, No. 2, Feb. 1979, pp. 134-150.
Derossi, et al., The third helix of the Antennapedia homeodomain translocates through biological membranes, J Biol Chem., vol. 269, No. 14, Apr. 8, 1994, pp. 10444-10450.
Ding, et al., Integrating light-sheet imaging with virtual reality to recapitulate developmental cardiac mechanics, JCI Insight, vol. 2, No. 22: e97180, Nov. 16, 2017, 12 pages.
Dubois, et al., Akt3-Mediated Protection Against Inflammatory Demyelinating Disease, Front Immunol., vol. 10, No. 1738, Jul. 25, 2019, pp. 1-19.
Dudley, et al., CD8+ enriched "young" tumor infiltrating lymphocytes can mediate regression of metastatic melanoma, Clin Cancer Res., vol. 16, No. 24, Dec. 15, 2010, pp. 6122-6131.
Elbashir, et al., Duplexes of 21-nucleotide RNAs mediate RNA interference in cultured mammalian cells, Nature, vol. 411, No. 6836, May 24, 2001, pp. 494-498.
Elbashir, et al., RNA interference is mediated by 21- and 22-nucleotide RNAs, Genes Dev., vol. 15, No. 2, Jan. 15, 2001, pp. 188-200.
Emamian, et al., Convergent evidence for impaired AKT1-GSK3beta signaling in schizophrenia, Nat Genet., vol. 36, No. 2, Feb. 2004, pp. 131-137.
European Search Report and Search Opinion Received for EP Application No. 18854685, mailed on May 7, 2021, 6 pages.
Examiner Interview Summary received for U.S. Appl. No. 14/832,915, mailed on Nov. 24, 2020, 2 pages.
Final Office Action received for U.S. Appl. No. 16/989,481, mailed on Oct. 6, 2021, 7 pages.
Final Office Action received for U.S. Appl. No. 16/782,811, mailed on Nov. 13, 2020, 7 pages.
Final Rejection received for U.S. Appl. No. 14/832,915, mailed on May 23, 2018.
Final Rejection received for U.S. Appl. No. 14/832,915, mailed on Oct. 10, 2019.
Final Rejection received for U.S. Appl. No. 15/407,600, mailed on Jun. 15, 2018.
Final Rejection received for U.S. Appl. No. 15/407,659, mailed on May 22, 2018.
Final Rejection received for U.S. Appl. No. 15/540,455, mailed on Feb. 24, 2020.
Finlay, et al., Phosphoinositide 3-kinase (PI3K) and the nutrient sensing mTOR (mammalian target of rapamycin) pathways control T cell migration, Ann N Y Acad Sci., vol. 1183, Jan. 2010, pp. 149-157.
Fire, et al., Potent and specific genetic interference by double-stranded RNA in Caenorhabditis elegans, Nature, vol. 391, No. 6669, Feb. 19, 1998, pp. 806-811.
First Examiners Report received for CL 0578-2020, mailed on Aug. 6, 2021, 28 pages (5 pages of English Translation and 23 pages of Official Copy).
Fontenot, et al., Foxp3 programs the development and function of CD4+CD25+ regulatory T cells, Nat Immunol., vol. 4, No. 4, Apr. 2003, pp. 330-336.
Fousteri, et al., Subcutaneous insulin B:9-23/IFA immunisation induces Tregs that control late-stage prediabetes in NOD mice through IL-10 and IFNgamma, Diabetologia, vol. 53, No. 9, Sep. 2010, pp. 1958-1970.
Franke, Thomas, Intracellular Signaling by Akt: Bound to Be Specific, Science Signaling, vol. 1, No. 24: pe29, Feb. 2008.
Frankel, et al., Cellular uptake of the tat protein from human immunodeficiency virus, Cell, vol. 55, No. 6, Dec. 23, 1988, pp. 1189-1193.
Furman, et al., An Isoform-Selective Inhibitor of Phosphatidylinositol 3-Kinase P110{delta}, Demonstrates Clinical Activity and Pharmacodynamic Effects In Patients with Relapsed or Refractory Chronic Lymphocytic Leukemia, Blood (ASH Annual Abstracts), vol. 116: Abstract 55, 2010, 3 pages.
Gamage, et al., Structure-activity relationships for 4-anilinoquinoline derivatives as inhibitors of the DNA methyltransferase enzyme DNMT1, Bioorg Med Chem., vol. 21, No. 11, Jun. 1, 2013, pp. 3147-3153.
Garofalo, et al., Severe diabetes, age-dependent loss of adipose tissue, and mild growth deficiency in mice lacking Akt2/PKB beta, J Clin Invest., vol. 112, No. 2, Jul. 2003, pp. 197-208.
Genbank, *Homo sapiens* mRNA for phosphoinositide 3-kinase, Accession No. Y10055.2, May 18, 1997, 3 pages.
George, et al., A Family with Severe Insulin Resistance and Diabetes Mellitus due to a Missense Mutation in AKT2, Science., vol. 304, No. 5675, May 28, 2004, pp. 1325-1328.
Glisic, et al., Inducible regulatory T cells (iTregs) from recent-onset type 1 diabetes subjects show increased in vitro suppression and higher ITCH levels compared with controls, Cell Tissue Res., vol. 339, No. 3, Mar. 2010, pp. 585-595.
Hammond, et al., An RNA-directed nuclease mediates post-transcriptional gene silencing in Drosophila cells, Nature, vol. 404, No. 6775, Mar. 16, 2000, pp. 293-296.
Hannon, Gregory J., RNA interference, Nature, vol. 418, No. 6894, Jul. 11, 2002, pp. 244-251.
Haribhai, et al., A Requisite Role for Induced Regulatory T cells in Tolerance Based on Expanding Antigen Receptor Diversity, Immunity., vol. 35, No. 1, Jul. 22, 2011, pp. 109-122.
Haxhinasto, et al., The AKT-mTOR axis regulates de novo differentiation of CD4+Foxp3+ cells, J Exp Med., vol. 205, No. 3, Mar. 17, 2008, pp. 565-574.
Hayashi, et al., Inhibition of experimental asthma by indoleamine 2,3-dioxygenase, J Clin Invest., vol. 114, No. 2, Jul. 15, 2004, pp. 270-279.
Hayreh, S S., The role of optic nerve sheath fenestration in management of anterior ischemic optic neuropathy, Arch Ophthalmol., vol. 108, No. 8, Aug. 1990, pp. 1063-1065.
Hinrichs, et al., Human effector CD8+ T cells derived from naive rather than memory subsets possess superior traits for adoptive immunotherapy, Blood, vol. 117, No. 3, Jan. 20, 2011, pp. 808-814.
Ho, et al., Synthetic protein transduction domains: enhanced transduction potential in vitro and in vivo, Cancer Res., vol. 61, No. 2, Jan. 15, 2001, pp. 474-477.
Ho, et al., Tolerizing DNA vaccines for autoimmune arthritis, Autoimmunity, vol. 39, No. 8, Dec. 2006, pp. 675-682.
Hori, et al., Control of Regulatory T Cell Development by the Transcription Factor Foxp3, SCIENCE, vol. 299, No. 5609, Jan. 9, 2003, pp. 1057-1061.
Hyrup, et al., Peptide nucleic acids (PNA): synthesis, properties and potential applications, Bioorg Med Chem, vol. 4, No. 1, Jan. 1996, pp. 5-23.
Ilan, Yaron, Oral tolerance: can we make it work?, Hum Immunol., vol. 70, No. 10, Oct. 2009, pp. 768-776.

(56) References Cited

OTHER PUBLICATIONS

International Preliminary Report on Patentability received for PCT Patent Application No. PCT/US15/068061, mailed on Jul. 13, 2017, 6 pages.
International Preliminary Report on Patentability received for PCT Patent Application No. PCT/US18/049715, mailed on Mar. 19, 2020, 9 pages.
International Search Report and Written Opinion received for PCT Patent Application No. PCT/US18/049715, mailed on Jan. 16, 2019, 12 pages.
International Search Report and Written Opinion received for PCT Patent Application No. PCT/US2015/068061, mailed on May 5, 2016, 7 pages.
International Search Report received for PCT Patent Application No. PCT/US2021/027987, mailed on Sep. 9, 2021, 6 pages.
International Search Report received for PCT Patent Application No. PCT/US2021/044909, mailed on Dec. 2, 2021, 3 pages.
Johnson, et al., Targeting the immunoregulatory indoleamine 2,3 dioxygenase pathway in immunotherapy, Immunotherapy., vol. 1, No. 4, Jul. 1, 2009, pp. 645-661.
Juntilla, et al., Akt1 and Akt2 are required for alphabeta thymocyte survival and differentiation, Proc Natl Acad Sci U S A., vol. 104, No. 29, Jul. 17, 2007, pp. 12105-12110.
Kabouridis, Panagiotis S., Biological applications of protein transduction technology, Trends Biotechnol., vol. 21, No. 11, Nov. 2003, pp. 498-503.
Kamiński, et al., T cell Activation is Driven by an ADP-Dependent Glucokinase Linking Enhanced Glycolysis with Mitochondrial Reactive Oxygen Species Generation, Cell Rep., vol. 2, No. 5, Nov. 29, 2012, pp. 1300-1315.
Kane, et al., The PI-3 kinase/Akt pathway and T cell activation: pleiotropic pathways downstream of PIP3, Immunol Rev., vol. 192, Apr. 2003, pp. 7-20.
Khare, et al., Whole-Cell Screening-Based Identification of Inhibitors against the Intraphagosomal Survival of Mycobacterium tuberculosis, Antimicrob Agents Chemother., vol. 57, No. 12, Dec. 2013, pp. 6372-6377.
Khattri, et al., An essential role for Scurfin in CD4+CD25+ T regulatory cells, Nat Immunol., vol. 4, No. 4, Apr. 2003, pp. 337-342.
Killer, et al., Architecture of arachnoid trabeculae, pillars, and septa in the subarachnoid space of the human optic nerve: anatomy and clinical considerations, Br J Ophthalmol., vol. 87, No. 6, Jun. 2003, pp. 777-781.
Kim, et al., Natural and inducible TH17 cells are regulated differently by Akt and mTOR pathways, Nat Immunol., vol. 14, No. 6, Jun. 2013, pp. 611-618.
Kim, et al., Role of PI3K/Akt signaling in memory CD8 T cell differentiation, Front Immunol, vol. 4, No. 20, Feb. 1, 2013, pp. 1-11.
Kim, et al., Signal integration by Akt regulates CD8 T cell effector and memory differentiation, J Immunol., vol. 188, No. 9, May 1, 2012, pp. 4305-4314.
Kim, Hyung L., Antibody-based depletion of Foxp3+ T cells potentiates antitumor immune memory stimulated by mTOR inhibition, Oncoimmunology., vol. 3: e29081, 2014.
Kimberly, et al., Correlation of optic nerve sheath diameter with direct measurement of intracranial pressure, Acad Emerg Med., vol. 15, No. 2, Feb. 2008, pp. 201-204.
Klebanoff, et al., CD8+ T-cell memory in tumor immunology and immunotherapy, Immunol Rev., vol. 211, Jun. 2006, pp. 214-224.
Klebanoff, et al., Central memory self/tumor-reactive CD8+ T cells confer superior antitumor immunity compared with effector memory T cells, Proc Natl Acad Sci U S A., vol. 102, No. 27, Jul. 5, 2005, pp. 9571-9576.
Lei, et al., Regulatory T cell-mediated anti-inflammatory effects promote successful tissue repair in both indirect and direct manners, Front Pharmacol., vol. 6, No. 184, Sep. 2, 2015, pp. 1-10.
Li, et al., CD4+CD25+ regulatory T-cell lines from human cord blood have functional and molecular properties of T-cell anergy, Blood, vol. 106, No. 9, Nov. 1, 2005, pp. 3068-3073.
Li, et al., Regulating mammalian target of rapamycin to tune vaccination-induced CD8(+) T cell responses for tumor immunity, J Immunol., vol. 188, No. 7, Apr. 1, 2012, pp. 3080-3087.
Liang, et al., Design of new oxazaphosphorine anticancer drugs, Curr Pharm Des., vol. 13, No. 9, 2007, pp. 963-978.
Long, et al., Combination of rapamycin and IL-2 increases de novo induction of human CD4(+)CD25(+)FOXP3(+) T cells, J Autoimmun., vol. 30, No. 4, Jun. 2008, pp. 293-302.
Lou, et al., Dendritic cells strongly boost the antitumor activity of adoptively transferred T cells in vivo, Cancer research, vol. 64, No. 18, Sep. 15, 2004, pp. 6783-6790.
Maciolek, et al., Metabolism of activated T lymphocytes, Curr Opin Immunol., vol. 27, Apr. 2014, pp. 60-74.
Mao, et al., Unequal contribution of Akt isoforms in the double-negative to double-positive thymocyte transition, J Immunol., vol. 178, No. 9, May 1, 2007, pp. 5443-5453.
Martinez, et al., Single-stranded antisense siRNAs guide target RNA cleavage in RNAi, Cell, vol. 110, No. 5, Sep. 6, 2002, pp. 563-574.
Mineharu, et al., Blockade of mTOR signaling via rapamycin combined with immunotherapy augments antiglioma cytotoxic and memory T-cell functions, Mol Cancer Ther., vol. 13, No. 12, Dec. 2014, pp. 3024-3036.
Nakatani, et al., Up-regulation of Akt3 in estrogen receptor-deficient breast cancers and androgen-independent prostate cancer lines, J Biol Chem., vol. 274, No. 31, Jul. 30, 1999, pp. 21528-21532.
Napoli, et al., Introduction of a Chimeric Chalcone Synthase Gene into Petunia Results in Reversible Co-Suppression of Homologous Genes in trans, Plant Cell, vol. 2, No. 4, Apr. 1990, pp. 279-289.
Newton, et al., Evaluation of NTF1836 as an inhibitor of the mycothiol biosynthetic enzyme MshC in growing and non-replicating Mycobacterium tuberculosis, Bioorg Med Chem., vol. 19, No. 13, Jul. 1, 2011, pp. 3956-3964.
Non-Final Office Action received for U.S. Appl. No. 16/782,811, mailed on Jul. 29, 2020, 8 pages.
Non-Final Office Action received for U.S. Appl. No. 16/989,481, mailed on Apr. 28, 2021, 12 pages.
Non-Final Rejection received for U.S. Appl. No. 14/689,517, mailed on Jul. 12, 2016.
Non-Final Rejection received for U.S. Appl. No. 15/407,600, mailed on Dec. 6, 2017.
Non-Final Rejection received for U.S. Appl. No. 15/407,600, mailed on Dec. 28, 2018.
Non-Final Rejection received for U.S. Appl. No. 15/407,659, mailed on Dec. 13, 2017.
Non-Final Rejection received for U.S. Appl. No. 15/900,077, mailed on May 15, 2018.
Non-Final Rejection received for U.S. Appl. No. 16/269,146, mailed on Aug. 22, 2019.
Non-Final Rejection received for U.S. Appl. No. 14/832,915, mailed on Jun. 9, 2020.
Non-Final Rejection received for U.S. Appl. No. 14/832,915, mailed on Mar. 29, 2019.
Non-Final Rejection received for U.S. Appl. No. 14/832,915, mailed on Nov. 9, 2017.
Non-Final Rejection received for U.S. Appl. No. 15/540,455, mailed on Jan. 18, 2019.
Notice of Allowance received for U.S. Appl. No. 14/689,517, mailed on Apr. 26, 2017.
Notice of Allowance received for U.S. Appl. No. 15/407,600, mailed on Feb. 27, 2019.
Notice of Allowance received for U.S. Appl. No. 15/407,659, mailed on Jan. 10, 2019.
Notice of Allowance received for U.S. Appl. No. 15/900,077, mailed on Sep. 14, 2018.
Notice of Allowance received for U.S. Appl. No. 16/269,146, mailed on Nov. 26, 2019.
Notice of Allowance received for U.S. Appl. No. 16/416,509, mailed on Sep. 9, 2019.

(56) References Cited

OTHER PUBLICATIONS

Notice of Allowance received for U.S. Appl. No. 16/782,811, mailed on Dec. 23, 2020, 5 pages.
Nykanen, et al., ATP requirements and small interfering RNA structure in the RNA interference pathway, Cell, vol. 107, No. 3, Nov. 2, 2001, pp. 309-321.
O'Reilly, et al., Angiotensin-converting enzyme defines matrikine-regulated inflammation and fibrosis, JCI Insight, vol. 2, No. 22: e91923, Nov. 16, 2017.
Parry, et al., Signalling to suit function: tailoring phosphoinositide 3-kinase during T-cell activation, Trends in Immunology, vol. 28, 2007, pp. 161-168.
Patton, et al., Cutting edge: the phosphoinositide 3-kinase p110 delta is critical for the function of CD4+CD25+Foxp3+ regulatory T cells, J Immunol., vol. 177, No. 10, Nov. 15, 2006, pp. 6598-6602.
Patton, et al., The PI3K p110delta controls T-cell development, differentiation and regulation, Biochem Soc Trans., vol. 35 (Pt 2), Apr. 2007, pp. 167-171.
Pearce, et al., PI3Kδ Regulates the Magnitude of CD8+ T Cell Responses after Challenge with Listeria monocytogenes, J Immunol., vol. 195, No. 7, Oct. 1, 2015, pp. 3206-3217.
Printout from Uniprot describing gene Akt3 and the name of the protein encoded by the gene, Available at <http://www.uniprot.org/uniprot/Q9Y243>, Apr. 13, 2017.
Ranpura, et al., Finding and Characterizing the Complexes of Drug Like Molecules with Quadruplex DNA: Combined Use of an Enhanced Hydroxyl Radical Cleavage. Protocol and NMR, PLOS One, vol. 9, No. 4: e96218, 2014, pp. 1-7.
RecName: Full=phosphatidylinositol-4,5-bisphosphate 3-kinase catalytic subunit delta isoform; Short=P13-kinase subunit delta; Short=P13K-delta; Short:PtdIns-3-kinase subunit delta; AltName: Full=Phosphatidylinositol 4,5-bisphosphate 3-kinase 1, , Apr. 5, 1998, 9 pages.
Requirement for Restriction/Election received for U.S. Appl. No. 14/689,517, mailed on Oct. 29, 2015.
Requirement for Restriction/Election received for U.S. Appl. No. 14/832,915, mailed on Jun. 15, 2017.
Requirement for Restriction/Election received for U.S. Appl. No. 15/407,659, mailed on Jul. 14, 2017.
Requirement for Restriction/Election received for U.S. Appl. No. 15/540,455, mailed on Aug. 30, 2018.
Requirement for Restriction/Election received for U.S. Appl. No. 16/590,566, mailed on May 18, 2020.
Restifo, et al., Adoptive immunotherapy for cancer: harnessing the T cell response, Nat Rev Immunol., vol. 12, No. 4, Mar. 22, 2012, pp. 269-281.
Roberts, et al., Conventional and Unconventional T Cells, Clinical and Basic Immunodermatology, (Gaspari and Tyring (ed.)), Springer London (2008), Jan. 2008, pp. 85-104.
Roberts, et al., Differential contributions of central and effector memory T cells to recall responses, J Exp Med., vol. 202, No. 1, Jul. 4, 2005, pp. 123-133.
Romano, Gaetano, The role of the dysfunctional akt-related pathway in cancer: establishment and maintenance of a malignant cell phenotype, resistance to therapy, and future strategies for drug development, Review Scientifica (Cairo), Article ID 317186, 2013.
Rommel, et al., PI3K delta and PI3K gamma: partners in crime in inflammation in rheumatoid arthritis and beyond?, Nat Rev Immunol., vol. 7, No. 3, Mar. 2007, pp. 191-201.
Rosenberg, et al., Tumor progression can occur despite the induction of very high levels of self/tumor antigen-specific CD8+ T cells in patients with melanoma, J Immunol., vol. 175, No. 9, Nov. 1, 2005, pp. 6169-6176.
Sakaguchi, et al., Foxp3+ CD25+ CD4+ natural regulatory T cells in dominant self-tolerance and autoimmune disease, Immunol Rev., vol. 212, Aug. 2006, pp. 8-27.
Sakaguchi, et al., Immunologic self-tolerance maintained by activated T cells expressing IL-2 receptor alpha-chains (CD25). Breakdown of a single mechanism of self-tolerance causes various autoimmune diseases, J Immunol., vol. 155, No. 3, Aug. 1, 1995, pp. 1151-1164.
Sakaguchi, et al., Naturally arising Foxp3-expressing CD25+CD4+ regulatory T cells in self-tolerance and autoimmune disease, Curr Top Microbiol Immunol., vol. 305, 2006, pp. 51-66.
Sakaguchi, et al., Regulatory T cells and immune tolerance, Cell, vol. 133, No. 5, May 30, 2008, pp. 775-787.
Sakaguchi, S, Regulatory T cells: key controllers of immunologic self-tolerance, Cell, vol. 101, No. 5, 2000, pp. 455-458.
Sallusto, et al., Two subsets of memory T lymphocytes with distinct homing potentials and effector functions, Nature, vol. 401, 1999, pp. 708-712.
Samara, et al., CD4+Foxp3+ Regulatory T Cells are Dependent on PI3K Pathway Allowing for their Selective Inhibition, J. Immunother. Vol. 33, 2010, p. 873.
Sangai, et al., Biomarkers of Response to Akt Inhibitor MK-2206 in Breast Cancer, Clin Cancer Res., vol. 18, No. 20, Oct. 15, 2012, pp. 5816-5828.
Sasaki, et al., Design, synthesis, and biological activity of potent and orally available protein-coupled receptor 40 agonists, J Med Chem., vol. 54, No. 5, Mar. 10, 2011, pp. 1365-1378.
Sauer, et al., T cell receptor signaling controls Foxp3 expression via PI3K, Akt, and mTOR, Proc Natl Acad Sci U S A., vol. 105, No. 22, Jun. 3, 2008, pp. 7797-7802.
Schmidt, et al., Molecular Mechanisms of Treg-Mediated T Cell Suppression, Front Immunol., vol. 3, No. 51, 2012.
Sharma, et al., Targeting Akt3 signaling in malignant melanoma using isoselenocyanates, Clin Cancer Res., vol. 15, No. 5, Mar. 1, 2009, pp. 1674-1685.
Shirakura, et al., T-cell receptor gene therapy targeting melanoma-associated antigen-A4 inhibits human tumor growth in non-obese diabetic/SCID/ycnull mice, Cancer Science, vol. 103, No. 1, Jan. 2012, pp. 17-25.
Strauss, et al., Selective survival of naturally occurring human CD4+CD25+Foxp3+ regulatory T cells cultured with rapamycin, J Immunol., vol. 178, No. 1, Jan. 1, 2007, pp. 320-329.
Summerton, et al., Morpholino antisense oligomers: design, preparation, and properties, Antisense Nucleic Acid Drug Dev, vol. 7, No. 3, Jun. 1997, pp. 187-195.
Sun, et al., Activation of Akt and elF4E survival pathways by rapamycin-mediated mammalian target of rapamycin inhibition, Cancer Res., vol. 65, No. 16, Aug. 15, 2005, pp. 7052-7058.
Taha, et al., The use of docking-based comparative intermolecular contacts analysis to identify optimal docking conditions within glucokinase and to discover of new GK activators, J Comput Aided Mol Des., vol. 28, No. 5, May 2014, pp. 509-547.
Tschopp, et al., Essential role of protein kinase B gamma (PKB gamma/Akt3) in postnatal brain development but not in glucose homeostasis, Development, vol. 132, No. 13, Jul. 2005, pp. 2943-2954.
Tsiperson, et al., Suppression of inflammatory responses during MOG-induced experimental autoimmune encephalomyelitis is regulated by AKT3 signaling, J Immunol., vol. 190, No. 4, Feb. 15, 2013, pp. 1528-1539.
Ui-Tei, et al., Sensitive assay of RNA interference in Drosophila and Chinese hamster cultured cells using firefly luciferase gene as target, FEBS Lett., vol. 479, No. 3, Aug. 18, 2000, pp. 79-82.
Waart, et al., Inhibition of Akt signaling promotes the generation of superior tumor-reactive T cells for adoptive immunotherapy, Blood., vol. 124, No. 23, Nov. 27, 2014, pp. 3490-3500.
Wadia, et al., Transducible TAT-HA fusogenic peptide enhances escape of TAT-fusion proteins after lipid raft macropinocytosis, Nat Med., vol. 10, No. 3, Mar. 2004, pp. 310-315.
Walsh, et al., PTEN inhibits IL-2 receptor-mediated expansion of CD4+ CD25+ Tregs, J Clin Invest., vol. 116, No. 9, Sep. 2006, pp. 2521-2531.
Wang, et al., Glycogen Synthase Kinase 3: A Point of Convergence for the Host Inflammatory Response, Cytokine., vol. 53, No. 2, 2011, pp. 130-140.
Wen, et al., Effector cells derived from naive T cells used in tumor immunotherapy of mice bearing B16 melanoma, Chin Med J (Engl)., vol. 127, No. 7, 2014, pp. 1328-1333.

(56) References Cited

OTHER PUBLICATIONS

Wen, et al., The role of the transcription factor CREB in immune function, J Immunol., vol. 185, No. 11, Dec. 1, 2010, pp. 6413-6419.
Wender, et al., The design, synthesis, and evaluation of molecules that enable or enhance cellular uptake: peptoid molecular transporters, Proc Natl Acad Sci U S A., vol. 97, No. 24, Nov. 21, 2000, pp. 13003-13008.
Wherry, et al., Lineage relationship and protective immunity of memory CD8 T cell subsets, Nat Immunol., vol. 4, No. 3, Mar. 2003, pp. 225-234.
Wu, et al., Human effector T cells derived from central memory cells rather than CD8(+)T cells modified by tumor-specific TCR gene transfer possess superior traits for adoptive immunotherapy, Cancer Lett., vol. 339, No. 2, Oct. 10, 2013, pp. 195-207.
Xiao, et al., Mucosal tolerance: a two-edged sword to prevent and treat autoimmune diseases, Clin Immunol Immunopathol., vol. 85, No. 2, Nov. 1997, pp. 119-128.
Xiao, et al., Transcriptional and Translational Regulation of Transforming Growth Factor- Production in Response to Apoptotic Cells, J Immunol., vol. 181, No. 5, 2008, pp. 3575-3585.
Yang, et al., Protein kinase B alpha/Akt1 regulates placental development and fetal growth, J Biol Chem., vol. 278, No. 34, 2003, pp. 32124-32131.
Yap, et al., Interrogating two schedules of the AKT inhibitor MK-2206 in patients with advanced solid tumors incorporating novel pharmacodynamic and functional imaging biomarkers, Clin Cancer Res., vol. 20, No. 22, Nov. 15, 2014, pp. 5672-5685.
Yee, et al., Adoptive T cell therapy using antigen-specific CD8+ T cell clones for the treatment of patients with metastatic melanoma: in vivo persistence, migration, and antitumor effect of transferred T cells, Proc Natl Acad Sci U S A., vol. 99, No. 25, Dec. 10, 2002, pp. 16168-16173.
Zhou, et al., Depletion of CD4+ CD25+ regulatory T cells promotes CCL21-mediated antitumor immunity, PLoS One., vol. 8, No. 9: e73952, Sep. 2, 2013.
Onnis , et al., "Synthesis and Evaluation of Paracetamol Esters as Novel Fatty Acid Amide Hydrolase Inhibitors", Journal of Medicinal Chemistry, vol. 53, No. 5, 2010, pp. 2286-2298.
Ikezoe , et al., "Longitudinal inhibition of PI3K/Akt/mTOR signaling by LY294002 and rapamycin induces growth arrest of adult T-cell leukemia cells", Leuk Res., vol. 31, No. 5, May 2007, pp. 673-682.
Katsuya, et al., "Phosphatidylinositol 3-kinase-δ (PI3K-δ) is a potential therapeutic target in adult T-cell leukemia-lymphoma", Biomarker Research, vol. 6, No. 1: 24, Jul. 2018, 4 pages.

* cited by examiner mJJ64A structure

Controls

Akt3 KI

WT—normal colon

Rag—/—colitis—untreated

WT—normal colon

Rag—/— colitis—untreated

Rag—/—colitis—iTreg treated

Rag—/—colitis—mJJ64A (10mg/kg) treated

Rag—/—colitis—iTreg treated

Rag—/—colitis—mJJ64A (10mg/kg) treated

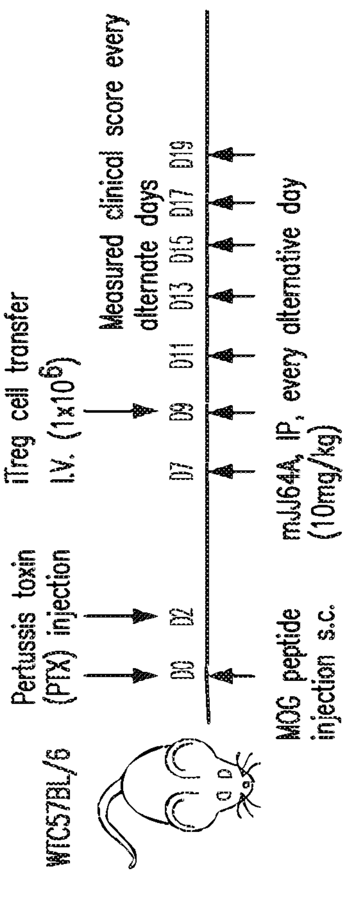
FIG. 19A
| Grade | Clinical sign |
|---|---|
| 0 | No clinical signs |
| 1 | Partially limp tail |
| 2 | One hind limb paralyzed |
| 3 | Hind limb paralyzed, weakness in forelimbs |
| 4 | Hind limb paralyzed, one forelimb paralyzed |
| 5 | Hind limbs paralyzed, both forelimbs paralyzed, |
| 6 | Moribund, Death |
FIG. 19B
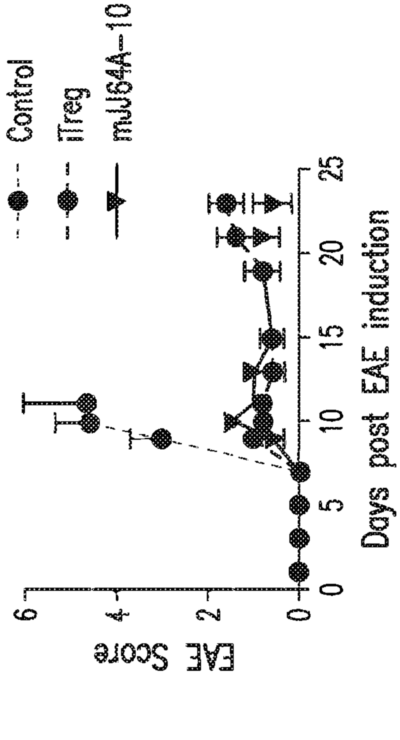
FIG. 19C
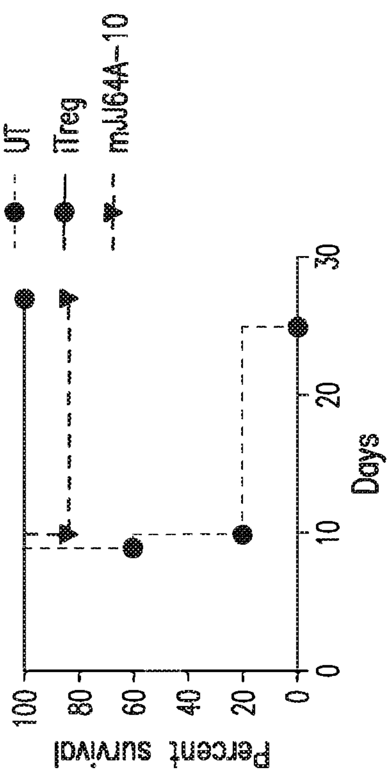
FIG. 19D

SEQUENCE LISTING

```
Sequence total quantity: 3
SEQ ID NO: 1            moltype = DNA  length = 1708
FEATURE                 Location/Qualifiers
source                  1..1708
                        mol_type = unassigned DNA
                        organism = Homo sapiens
SEQUENCE: 1
aggggagtca tcatgagcga tgttaccatt gtgaaggaag gttgggttca gaagagggga  60
gaatatataa aaaactggag gccaagatac ttccttttga agacagatgg ctcattcata  120
ggatataaag agaaacctca agatgtggat ttaccttatc ccctcaacaa cttttcagtg  180
gcaaaatgcc agttaatgaa aacagaacga ccaaagccaa acacatttat aatcagatgt  240
ctccagtgga ctactgttat agagagaaca tttcatgtag atactccaga ggaaagggaa  300
gaatggacag aagctatcca ggctgtagca gacagactgc agaggcaaga agaggagaga  360
atgaattgta gtccaacttc acaaattgat aatataggag aggaagagat ggatgcctct  420
acaacccatc ataaaagaaa gacaatgaat gattttgact atttgaaact actaggtaaa  480
ggcacttttg ggaaagttat tttggttcga gagaaggcaa gtggaaaata ctatgctatg  540
aagattctga agaaagaagt cattattgca aaggatgaag tggcacacac tctaactgaa  600
agcagagtat taaagaacac tagacatccc tttttaacat ccttgaaata ttccttccag  660
acaaaagacc gtttgtgttt tgtgatggaa tatgttaatg ggggcgagct gtttttccat  720
ttgtcgagag agcgggtgtt ctctgaggac cgcacacgtt tctatggtgc agaaattgtc  780
tctgccttgg actatctaca ttccggaaag attgtgtacc gtgatctcaa gttggagaat  840
ctaatgctgg acaaagatgg ccacataaaa attacagatt ttggactttg caaagaaggg  900
atcacagatg cagccaccat gaagacattc tgtggcactc cagaatatct ggcaccagag  960
gtgttagaag ataatgacta tggccgagca gtagactggt ggggcctagg ggttgtcatg  1020
tatgaaatga tgtgtgggag gttacctttc tacaaccagg accatgagaa actttttgaa  1080
ttaatattaa tggaagacat taaatttcct cgaacactct cttcagatgc aaaatcattg  1140
ctttcagggc tcttgataaa ggatccaaat aaacgccttg gtggaggacc agatgatgca  1200
aaagaaatta tgagacacag tttcttctct ggagtaaact ggcaagatgt atatgataaa  1260
aagcttgtac ctcctttttaa acctcaagta acatctgaga cagatactag atattttgat  1320
gaagaattta cagctcagac tattacaata acaccacctg aaaaatatga tgaggatggt  1380
atggactgca tggacaatga gaggcggccg catttccctc aattttccta ctctgcaagt  1440
ggacgagaat aagtctcttt cattctgcta cttcactgtc atcttcaatt tattactgaa  1500
aatgattcct ggacatcacc agtcctagct cttacacata gcaggggcac cttccgacat  1560
cccagaccag ccaagggtcc tcacccctcg ccacctttca ccctcatgaa aacacacata  1620
cacgcaaata cactccagtt tttgtttttg catgaaattg tatctcagtc taaggtctca  1680
tgctgttgct gctactgtct tactatta                                    1708

SEQ ID NO: 2            moltype = AA  length = 479
FEATURE                 Location/Qualifiers
source                  1..479
```

-continued

```
                         mol_type = protein
                         organism = Homo sapiens
SEQUENCE: 2
MSDVTIVKEG WVQKRGEYIK NWRPRYFLLK TDGSFIGYKE KPQDVDLPYP LNNFSVAKCQ  60
LMKTERPKPN TFIIRCLQWT TVIERTFHVD TPEEREEWTE AIQAVADRLQ RQEEERMNCS  120
PTSQIDNIGE EEMDASTTHH KRKTMNDFDY LKLLGKGTFG KVILVREKAS GKYYAMKILK  180
KEVIIAKDEV AHTLTESRVL KNTRHPFLTS LKYSFQTKDR LCFVMEYVNG GELFFHLSRE  240
RVFSEDRTRF YGAEIVSALD YLHSGKIVYR DLKLENLMLD KDGHIKITDF GLCKEGITDA  300
ATMKTFCGTP EYLAPEVLED NDYGRAVDWW GLGVVMYEMM CGRLPFYNQD HEKLFELILM  360
EDIKFPRTLS SDAKSLLSGL LIKDPNKRLG GGPDDAKEIM RHSFFSGVNW QDVYDKKLVP  420
PFKPQVTSET DTRYFDEEFT AQTITITPPE KYDEDGMDCM DNERRPHFPQ FSYSASGRE   479

SEQ ID NO: 3             moltype = AA  length = 478
FEATURE                  Location/Qualifiers
source                   1..478
                         mol_type = protein
                         organism = Homo sapiens
SEQUENCE: 3
SDVTIVKEGW VQKRGEYIKN WRPRYFLLKT DGSFIGYKEK PQDVDLPYPL NNFSVAKCQL  60
MKTERPKPNT FIIRCLQWTT VIERTFHVDT PEEREEWTEA IQAVADRLQR QEEERMNCSP  120
TSQIDNIGEE EMDASTTHHK RKTMNDFDYL KLLGKGTFGK VILVREKASG KYYAMKILKK  180
EVIIAKDEVA HTLTESRVLK NTRHPFLTSL KYSFQTKDRL CFVMEYVNGG ELFFHLSRER  240
VFSEDRTRFY GAEIVSALDY LHSGKIVYRD LKLENLMLDK DGHIKITDFG LCKEGITDAA  300
TMKTFCGTPE YLAPEVLEDN DYGRAVDWWG LGVVMYEMMC GRLPFYNQDH EKLFELILME  360
DIKFPRTLSS DAKSLLSGLL IKDPNKRLGG GPDDAKEIMR HSFFSGVNWQ DVYDKKLVPP  420
FKPQVTSETD TRYFDEEFTA QTITITPPEK YDEDGMDCMD NERRPHFPQF SYSASGRE    478
```

SPECIFIC AKT3 ACTIVATOR AND USES THEREOF

CROSS-REFERENCE TO RELATED APPLICATIONS

This application is a continuation of U.S. application Ser. No. 16/645,293 filed Mar. 6, 2020, which is a National Phase application under 35 U.S.C. § 371 of PCT/US2018/049715, filed Sep. 6, 2018, which claims benefit of and priority to U.S. Provisional Application Nos. 62/555,141 filed on Sep. 7, 2017, 62/657,345 filed on Apr. 13, 2018, and 62/659,870 filed on Apr. 19, 2018, which are incorporated by reference in their entirety.

REFERENCE TO SEQUENCE LISTING

The Sequence Listing XML submitted as a file named "AURI_2017_030_CON_ST26.xml," created on Mar. 11, 2024, and having a size of 6,331 bytes is hereby incorporated by reference pursuant to 37 C.F.R. § 1.834(c)(1).

FIELD OF THE INVENTION

The invention is generally directed to compositions and methods for selective activation of Akt3 activity, and methods of use thereof for modulating regulator T cells.

BACKGROUND OF THE INVENTION

Regulatory T cells (Tregs) are a subset of CD4+ T cells that suppress immune responses and are essential mediators of self-tolerance and immune homeostasis (Sakaguchi, et al., *Cell,* 133, 775-787 (2008)). Depletion or inactivation of Tregs results in the development of severe autoimmunity (Sakaguchi, et al., *J. Immunol.,* 155, 1151-1164 (1995)), and their accumulation inhibits anti-tumor immunity (Dannull, et al., *The Journal of clinical investigation,* 115, 3623-3633 (2005)). Tregs are characterized by Foxp3 expression, a transcription factor belonging to the Forkhead Box family of transcription factors. The Foxp3 is a master regulator of Tregs, as it is necessary for their development and function (Hori, *Science,* 299, 1057-1061 (2003); Fontenot, et al., *Nat Immunol.,* 4(4):330-6 (2003). Epub 2003 Mar. 3; Khattri, et al., *Nat Immunol.,* 4(4):337-42 (2003). Epub 2003 Mar. 3)).

There are two major types of Tregs: thymus-derived Tregs (or natural Tregs (nTregs)) that constitute 5-10% of the total peripheral CD4+ T cells, and peripheral TGFβ-induced Tregs (iTregs). Both types are shown to have immunosuppressive properties mediated via several processes that involve immunosuppressive soluble factors or cell contact (Bluestone, et al., *Nat Rev Immunol,* 3, 253-257 (2003); Glisic, et al., *Cell and Tissue Research,* 339, 585-595 (2010); Hori, *Science,* 299, 1057-1061 (2003); Sakaguchi, *Cell,* 101, 455-458 (2000); Sakagushi, et al., *Curr. Top Microbiol. Immunol.,* 305, 51-66 (2006); Sakagushi, et al., *Immunol., Rev.,* 212, 8-27 (2006); (Schmidt, et al., *Front Immunol.,* 3:51 (2012)). However, the molecular mechanisms by which nTreg and iTreg develop and then exhibit non-redundant roles to suppress the immunity are not fully understood (Dipica, et al., *Immunity,* 35(1):109-122 (2011)).

PI3K-Akt signaling affects many processes and is central to many signaling pathways. Akt phosphorylation and kinase activity are induced by PI3K activation, which is, in turn, induced by several growth factor receptors, TCR, CD28, and IL-2R, among many others (Parry, et al., *Trends in Immunology,* 28, 161-168 (2007)). In mammals, there are three Akt isoforms, namely Akt1, Akt2, and Akt3, encoded by three independent genes. In vitro, these isoforms appear to have redundant functions, as different extracellular inputs can induce similar Akt signaling patterns (Franke, Science 1, pe29-(2008)). However, isoform-specific knockouts show unique features and their involvement in diseases and physiological conditions is different (Boland, et al., *American Journal of Human Genetics,* 81, 292-303 (2007); DeBosch, et al., *J. Biol. Chem,* 281, 32841-32851 (2006); Emamian, et al., *Nat Genet,* 36, 131-137 (2004); Garofalo, et al., *The Journal of clinical investigation,* 112, 197-208 (2003); George, et al., *Science,* 304, 1325-1328 (2004); Nakatani, et al., *The Journal of Biological Chemistry,* 274, 21528-21532 (1999); Tschopp, et al., *Development* (Cambridge, England), 132, 2943-2954 (2005); Yang, et al., *J. Biol. Chem.,* 278, 32124-32131 (2003)).

Studies have shown that Akt1 and Akt2 can negatively regulate the transcriptional signature of Treg, thereby selectively affecting Treg lineage differentiation (Sauer, et al., *Proceedings of the National Academy of Sciences,* 105, 7797-7802 (2008a)). Additionally, although it was shown that inhibition of Akt1 and Akt2 isoforms increase Foxp3 expression in TGFβ induced iTregs (Sauer, et al., *Proc. Natl. Acad. Sci. USA,* 105, 7797-7802 (2008b)), the mechanism remained unclear. Another finding shows that deletion of Akt2 resulted in defective iTh17 cell differentiation but preserved nTh17 cell development (Kim, et al., *Nat Immunol.,* 14(6):611-8 (2013) Epub 2013 May 5). Further, Akt3 is also expressed in immune cells and the spinal cord of Akt3 knockout mice have decreased numbers of Foxp3+ regulatory T cells compared with wild type mice (Tsiperson, et al., *J Immunol.,* 190(4):1528-39 (2013) Epub 2013 Jan. 18)). Thus, although some studies have examined the relevance of Akt isoform expression on T cell biology (Carson, et al., *Annals of the New York Academy of Sciences,* 1103, 167-178 (2007), Crellin, et al., *Blood,* 109, 2014-2022 (2007a); Crellin, et al., *Journal of Immunological Methods,* 324, 92-104 (2007b); Haxhinasto, *J. Exp. Med.,* 205, 565-574 (2008); Li, et al., *Blood,* 106, 3068-3073 (2005); Patton, et al., *Biochem. Soc. Trans.,* 35, 167-171 (2007); Patton, et al., *J. Immunology* 177, 6598-6602 (2006); Sauer, et al., *Proc. Natl. Acad. Sci. USA,* 105, 7797-7802 (2008b); Walsh, et al., *J. Clin. Invest.,* 116, 2521-2531. (2006)), the roles that Akt isoforms play in Treg function and induction was not clear.

Therefore, it is an object of the invention to provide compounds and compositions for selectively activating Akt3 in immune cells.

It is another object of the invention to provide methods of decreasing an immune response in a subject.

Still another object of the invention is to provide methods of increasing a suppressive immune response in a subject.

SUMMARY OF THE INVENTION

Compositions and methods of selectively activating Akt3 are provided. One embodiment provides a compound according to Formula I:

Formula I

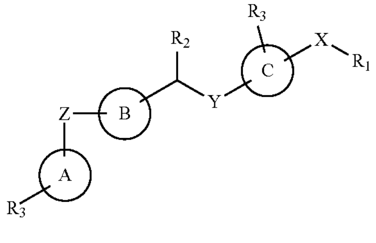

or a pharmaceutically acceptable enantiomer, salt, or solvate thereof, wherein:

rings A, B, and C are independently six-membered aryl or N-containing heteroaryl mono- or bicyclic ring systems containing zero or more N-atoms such as phenyl, pyridine, pyrimidine, pyridazine, pyrazine, triazine, quinoline, quinazoline, isoquinoline, naphthalene, naphthyridine, indole, isoindole, cinnoline, phthalazine, quinoxaline, pteridine, purine, and benzimidazole.

$R_1$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SH, —$SO_3H$, —CN, —$NH_2$, or a halogen;

X, Y, and Z are independently selected from =O, —NH, —S, —N—($C_1$-$C_{30}$)-alkyl, or —($C_1$-$C_{30}$)-aryl;

$R_2$ is selected from —($C_1$-$C_{30}$)-alkyl, =O, —OH, —$SO_2$, —SO, or —$SOCH_3$; and $R_3$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SH, —$SO_3H$, —CN, —$NH_2$, or a halogen.

Another embodiment provides a compound according to Formula II

Formula II

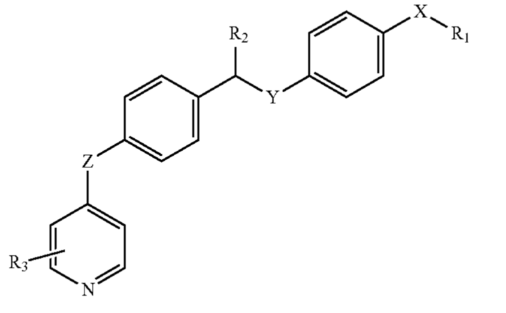

or a pharmaceutically acceptable enantiomer, salt, or solvate thereof, wherein:

$R_1$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SH, —$SO_3H$, —CN, —$NH_2$, or a halogen;

X, Y, and Z are independently selected from —O, —NH, —S, —N—($C_1$-$C_{30}$)-alkyl, or —($C_1$-$C_{30}$)-aryl;

$R_2$ is selected from —($C_1$-$C_{30}$)-alkyl, —O, —OH, —$SO_2$, —SO, or —$SOCH_3$; and $R_3$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SH, —$SO_3H$, —CN, —$NH_2$, or a halogen.

Another embodiment provides a compound according to Formula III:

Formula III

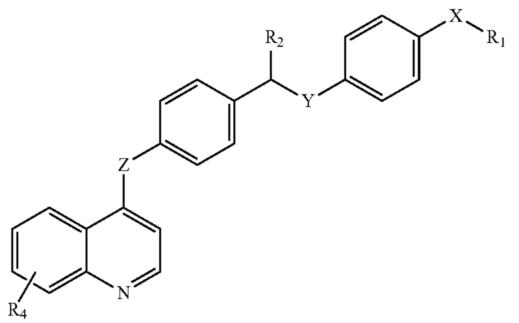

or a pharmaceutically acceptable enantiomer, salt, or solvate thereof, wherein.

$R_1$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl- $(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})$-alkyl$]_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SH, —$SO_3H$, —CN, —$NH_2$, or a halogen;

X, Y, and Z are independently selected from —O, —NH, —S, —N—$(C_1-C_{30})$-alkyl, or —$(C_1-C_{30})$-aryl;

$R_2$ is selected from —$(C_1-C_{30})$-alkyl, =O, —OH, —$SO_2$, —SO, or —$SOCH_3$; and $R_4$ is selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})$-alkyl$]_2$, —$(C_6-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SH, —$SO_3H$, —CN, —$NH_2$, or a halogen.

Another embodiment provides a compound according to Formula IV:

Formula IV

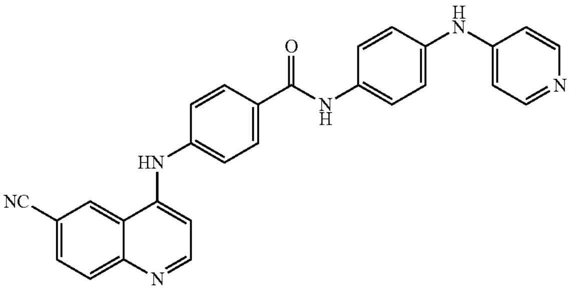

or a pharmaceutically acceptable enantiomer, salt, or solvate thereof.

It has been discovered that the compound according to Formula IV (also referred to as mJJ64A) selectively activates Akt3. The IUPAC name for mJJ64A is 4-(m-{[p-(4-Pyridylamino)phenylamino]carbonyl}phenylamino)-6-quinolinecarbonitrile. Because Akt3 modulates the suppressive function of natural Tregs and the polarization of induced Tregs, the compound of Formula IV and related compounds of Formulas I-III can be used for modulating immune responses.

One embodiment provides a method of increasing an immune suppressive response in a subject in need thereof comprising administering to the subject a composition including a compound according to Formula I, Formula II, Formula III, or Formula IV, or an enantiomer, polymorph, or pharmaceutically acceptable salt thereof that selectively activates Akt3 by an amount effective to increase the immune suppressive response in the subject.

For example, methods of increasing an immune suppressive response, decreasing an immune stimulating response, or a combination thereof in a subject in need thereof are disclosed. The methods typically include administering the subject a composition including a compound according to Formula I, Formula II, Formula III, or Formula IV, or an enantiomer, polymorph, or pharmaceutically acceptable salt thereof that selectively activates the bioactivity of Akt3 in an amount effective to increase or promote an immune suppressive response, decrease an immune stimulating response, or a combination thereof in the subject.

In some embodiments the immune suppressive response that is increased is selected from the group consisting of an immune suppressive function of natural Treg (nTreg) and the promotion of conventional T cells into induced Treg (iTreg). The immune suppressive function of nTreg can be the secretion of one or more anti-inflammatory cytokines. The anti-inflammatory cytokine(s) can IL10, TGFβ, or a combination thereof.

In some embodiments, the subject has an autoimmune disease. Therefore, methods of treating autoimmune diseases by administering to a subject in need thereof an effective amount of a compound according to Formula I, Formula II, Formula III, or Formula IV, or an enantiomer, polymorph, or pharmaceutically acceptable salt thereof that induces or increases the bioavailability or bioactivity of Akt3 are also disclosed.

Combination therapies including modulators of Akt3 bioactivity and methods of use thereof are also provided.

One embodiment provides a method of increasing an immune suppressive response in a subject in need thereof by administering to the subject a composition containing an effective amount of a compound according to Formula I, Formula II, Formula III, or Formula IV, or an enantiomer, polymorph, or pharmaceutically acceptable salt thereof that selectively activates Akt3 by an amount effective to increase the immune suppressive response in the subject. The subject can have an inflammatory disorder or disease, for example an autoimmune disease.

Another embodiment provides a method of treating an inflammatory disorder in a subject in need thereof by administering a composition comprising a compound according to Formula I, Formula II, Formula III, or Formula IV, or an enantiomer, polymorph, or pharmaceutically acceptable salt thereof that selectively activates Akt3 in an amount effective to increase, induce, or promote an immune suppressive response in the subject.

In some embodiments, the inflammatory disorder or disease is selected from the group consisting of rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, obesity, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

Another embodiment provides a method of treating an autoimmune disease by administering to a subject in need thereof a composition containing a compound according to Formula I, Formula II, Formula III, or Formula IV or an enantiomer, polymorph, or pharmaceutically acceptable salt thereof that selectively inhibits Akt3 in an amount effective to promote or enhance an immune suppressive response in the subject.

Exemplary autoimmune diseases include, but are not limited to rheumatoid arthritis, systemic lupus erythematosus, alopecia areata, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Crohn's disease multiple sclerosis, and myasthenia gravis.

In some embodiments, the immune suppressive response that is increased is selected from the group consisting of an immune suppressive function of natural Treg (nTreg) and induction of conventional T cells into induced Treg (iTreg). The immune suppressive function of nTreg can include the secretion of one or more anti-inflammatory cytokines, for example IL10, TGFβ, or a combination thereof.

Another embodiment provides a method of treating a subject in need thereof by administering an effective amount of a composition containing a compound according to Formula I, Formula II, Formula III, or Formula IV, or an enantiomer, polymorph, or pharmaceutically acceptable salt thereof in combination or alternation with a second immunosuppressive agent. Exemplary immunosuppressive agents include, but are not limited to prednisone, budesonide, prednisolone, cyclosporine, tacrolimus, sirolimus, everolimus, azathioprine, leflunomide, mycophenolate, abatacept, adalimumab, anakinra, certolizumab, etanercept, golimumab, infliximab, ixekizumab, natalizumab, rituximab, secukinumab, tocilizumab, ustekinumab, vedolizumab, basiliximab, daclizumab, muromonab, or combinations thereof.

In some embodiments, the compound according to Formula I, Formula II, Formula III, or Formula IV, or an enantiomer, polymorph, or pharmaceutically acceptable salt thereof is administered in an amount effective to increase FoxP3 expression on immune cells, for example T cells, including but not limited to Tregs such as iTregs and nTregs.

In other embodiments, the compound according to Formula I, Formula II, Formula III, or Formula IV, or an enantiomer, polymorph, or pharmaceutically acceptable salt thereof is administered in an amount effective to increase proliferation of iTregs and nTregs.

Still another embodiment provides a pharmaceutical composition containing a compound according to Formula I, Formula II, Formula III, or Formula IV, or an enantiomer, polymorph, or pharmaceutically acceptable salt thereof and an excipient. The compound according to Formula I, Formula II, Formula III, Formula IV, or an enantiomer, polymorph, or pharmaceutically acceptable salt thereof is typically in an amount effective to increase a suppressive immune response when administered to a subject in need thereof.

Another embodiment provides a method of increasing an immune suppressive response in subject in need thereof by contacting immune cells ex vivo with the compound according to Formula I, Formula II, Formula III, or Formula IV, or an enantiomer, polymorph, or pharmaceutically acceptable salt thereof, in an amount effective to increase expression of FoxP3 on the immune cells, and administering the contacted immune cells to the subject. In one embodiment, the immune cells are autologous immune cells. The immune cells can include T cells including but not limited to nTregs and iTregs.

Another embodiment provides a method for inhibiting or reducing transplant rejection in a subject in need thereof by administering to the subject an effective amount of a compound according to Formula I, Formula II, Formula III, or Formula IV, or an enantiomer, polymorph, or pharmaceutically acceptable salt thereof to increase FoxP3 expression on immune cells of the subject. In some embodiments, the increase of FoxP3 on immune cells of the subjects induces, promotes or increases a suppressive immune response in the subject.

Another embodiment provides a method for treating Graft-versus-host disease in a subject in need thereof by administering an effective amount of the compound according to Formula I, Formula II, Formula III, or Formula IV, or an enantiomer, polymorph, or pharmaceutically acceptable salt thereof to increase FoxP3 expression on immune cells of the subject.

Another embodiment provides a method for treating chronic infection in a subject in need thereof by administering an effective amount of the compound according to Formula I, Formula II, Formula III, or Formula IV, or an enantiomer, polymorph, or pharmaceutically acceptable salt thereof to increase FoxP3 expression on immune cells of the subject.

BRIEF DESCRIPTION OF THE DRAWINGS

FIG. 7D and FIG. 7G show IL2 expression in controls and Akt3 KI, respectively. FIG. 7E and FIG. 7H show actin expression in control and Akt3 KI, respectively. FIG. 7F and FIG. 7I show the overlay of the expression peaks of IL2 and actin for control and Akt3 KI, respectively.

FIG. 19A is a schematic illustration of induction of experimental autoimmune encephalomyelitis (EAE) model. FIG. 19B is a chart showing the grading criterion for scoring severity of EAE. FIG. 19C is a line graph showing EAE score over time (days post EAE induction) for control (●), iTreg (blue circle), and mJJ64A-10 (▼) treated mice. The X-axis represents time (days) and the Y-axis represents EAE score. FIG. 19D is a line graph showing percent survival over time (days) for untreated (●), iTreg treated (●), and mJJ64A-10 treated (▼) mice. The X-axis represents time (days) and the Y-axis represents percent survival.

DETAILED DESCRIPTION OF THE INVENTION

I. Definitions

Figure 1:
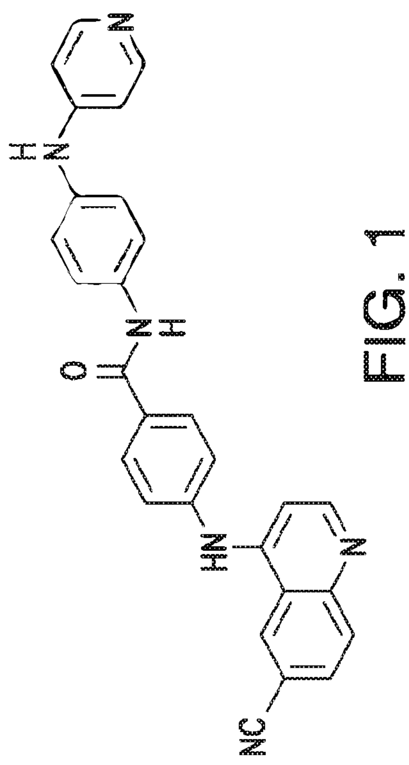
FIG. 1 shows the structure of the compound of Formula IV (mJJ64A).
Figures 2A, 2B, 2C, 2D, 2E, 2F:
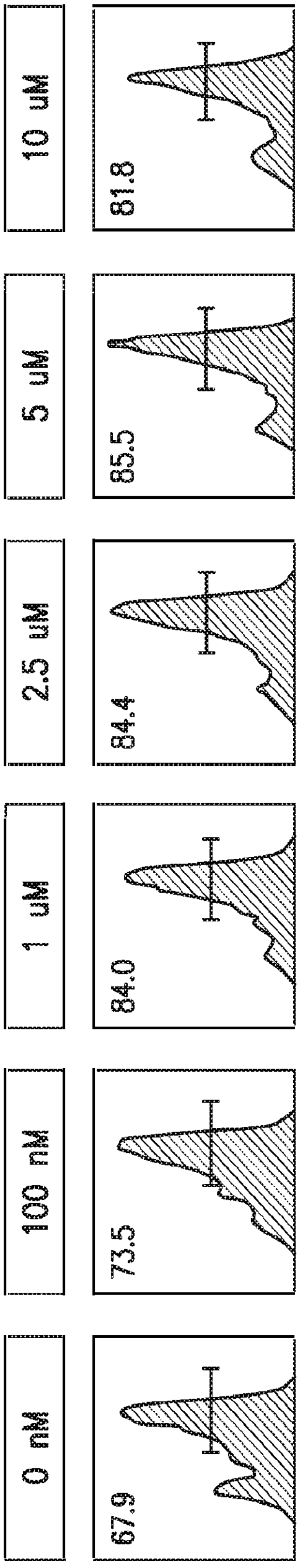
FIGS. 2A-2F are histograms of FACS sorted iTregs treated as indicated with mJJ64A.
Figure 2G:
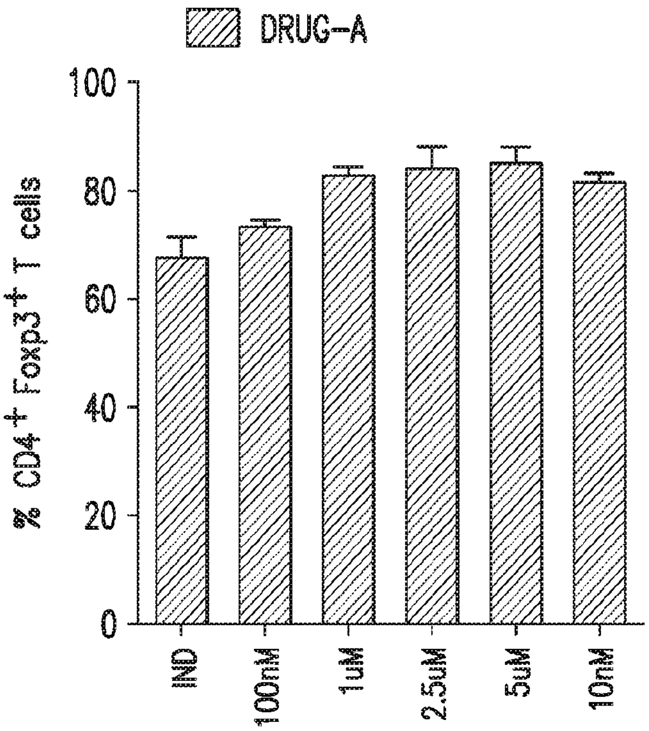
FIG. 2G is a bar graph showing percent CD4+Foxp3+ T cells treated with the indicated amount of mJJ64A.
Figure 2H:
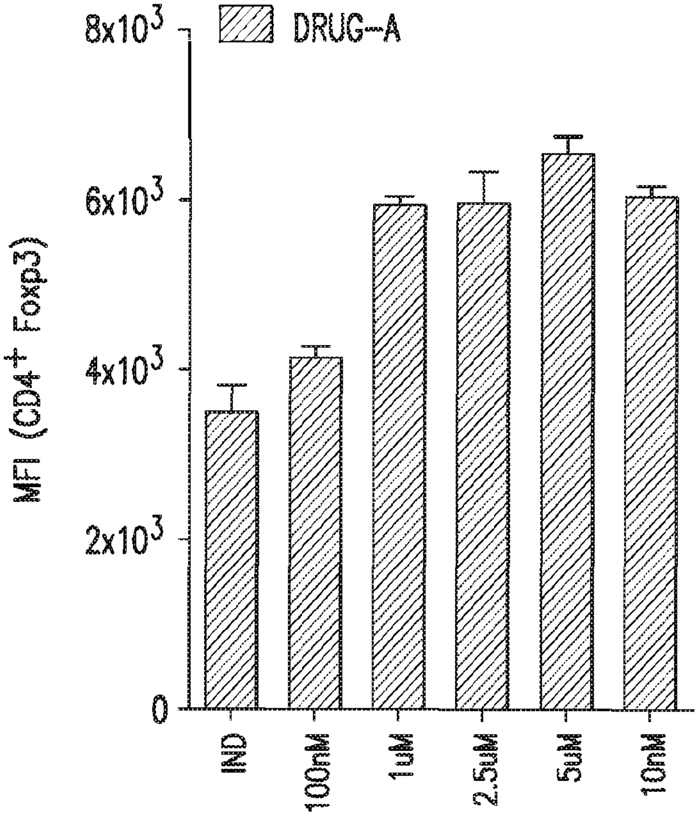
FIG. 2H is a bar graph of mean fluorescence intensity (MFI) (CD4+Foxp3 cells) treated as indicate with mJJ64A.

The term "stimulate expression of" means to affect expression of, for example to induce expression or activity, or induce increased/greater expression or activity relative to normal, healthy controls.

The terms "immune activating response", "activating immune response", and "immune stimulating response" refer to a response that initiates, induces, enhances, or increases the activation or efficiency of innate or adaptive immunity. Such immune responses include, for example, the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response can also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

The terms "suppressive immune response" and "immune suppressive response" refer to a response that reduces or prevents the activation or efficiency of innate or adaptive immunity.

The term "immune tolerance" as used herein refers to any mechanism by which a potentially injurious immune response is prevented, suppressed, or shifted to a non-injurious immune response (Bach, et al., *N. Eng. J. Med.,* 347:911-920 (2002)).

The term "tolerizing vaccine" as used herein is typically an antigen-specific therapy used to attenuate autoreactive T and/or B cell responses, while leaving global immune function intact.

An "immunogenic agent" or "immunogen" is capable of inducing an immunological response against itself on administration to a mammal, optionally in conjunction with an adjuvant.

The term "immune cell" refers to cells of the innate and acquired immune system including neutrophils, eosinophils, basophils, monocytes, macrophages, dendritic cells, lymphocytes including B cells, T cells, and natural killer cells.

As used herein "conventional T cells" are T lymphocytes that express an αβ T cell receptor (TCR) as well as a co-receptor CD4 or CD8. Conventional T cells are present in the peripheral blood, lymph nodes, and tissues. See, Roberts and Girardi, "Conventional and Unconventional T Cells", Clinical and Basic Immunodermatology, pp. 85-104, (Gaspari and Tyring (ed.)), Springer London (2008).

As used herein "unconventional T cells" are lymphocytes that express a γδ TCR and may commonly reside in an epithelial environment such as the skin, gastrointestinal tract, or genitourinary tract. Another subset of unconventional T cells is the invariant natural killer T (NKT) cell, which has phenotypic and functional capacities of a conventional T cell, as well as features of natural killer cells (e.g., cytolytic activity). See, Roberts and Girardi, "Conventional and Unconventional T Cells", Clinical and Basic Immunodermatology, pp. 85-104, (Gaspari and Tyring (ed.)), Springer London (2008).

As used herein "Treg" refers to a regulatory T cell or cells. Regulatory T cells are a subpopulation of T cells which modulate the immune system, maintain tolerance to self-antigens, abrogate autoimmune disease, and otherwise suppress immune stimulating or activating responses of other cells. Regulatory T cells come in many forms with the most well-understood being those that express CD4, CD25, and Foxp3.

As used herein "natural Treg" or "nTreg" refers to a regulatory T cell or cells that develop in the thymus.

As used herein "induced Treg" or "iTreg" refers to a regulatory T cell or cells that develop from mature CD4+ conventional T cells outside of the thymus.

The "bioactivity" of Akt3 refers to the biological function of the Akt3 polypeptide. Bioactivity can be increased or reduced by increasing or reducing the activity of basal levels of polypeptide, increasing or reducing the avidity of basal levels of polypeptide, the quantity of the polypeptide, the ratio of Akt3 relative to one or more other isoforms of Akt (e.g., Akt1 or Akt2) of the polypeptide, increasing or reducing the expression levels of the polypeptide (including by increasing or decreasing mRNA expression of Akt3), or a combination thereof. For example, bioavailable Akt3 polypeptide is a polypeptide that has kinase activity and can bind to and phosphorylate a substrate of Akt3. Akt3 polypeptide that is not bioavailable includes Akt3 polypeptide that is mis-localized or in-capable of binding to and phosphorylating Akt substrates.

As used herein, the phrase that a molecule "specifically binds" or "displays specific binding" to a target refers to a binding reaction which is determinative of the presence of the molecule in the presence of a heterogeneous population of other biologics.

Under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The terms "oligonucleotide" and "polynucleotide" generally refer to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "carrier" refers to an organic or inorganic ingredient, natural or synthetic, with which the active ingredient is combined to facilitate the application.

The term "pharmaceutically acceptable" means a non-toxic material that does not interfere with the effectiveness of the biological activity of the active ingredients.

The term "pharmaceutically-acceptable carrier" means one or more compatible solid or liquid fillers, dilutants or encapsulating substances which are suitable for administration to a human or other vertebrate animal.

The term "effective amount" or "therapeutically effective amount" means a dosage sufficient to provide treatment a disorder, disease, or condition being treated, or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "subject," and "patient" are used interchangeably herein, and refer to a mammal, including, but not limited to, humans, rodents, such as mice and rats, and other laboratory animals.

II. Compositions For Activating Akt3

Compositions and methods of their use for selectively activating Akt3 are provided herein.

One embodiment provides a compound of Formula I:

Formula I

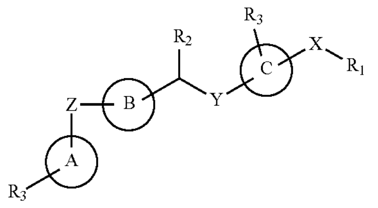

or a pharmaceutically acceptable enantiomer, salt, or solvate thereof, wherein:

rings A, B, and C are independently six-membered aryl or N-containing heteroaryl mono- or bicyclic ring systems containing zero or more N-atoms such as phenyl, pyridine, pyrimidine, pyridazine, pyrazine, triazine, quinoline, quinazoline, isoquinoline, naphthalene, naphthyridine, indole, isoindole, cinnoline, phthalazine, quinoxaline, pteridine, purine, and benzimidazole.

$R_1$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SH, —$SO_3H$, —CN, —$NH_2$, or a halogen;

X, Y, and Z are independently selected from =O, —NH, —S, —N—($C_1$-$C_{30}$)-alkyl, or —($C_1$-$C_{30}$)-aryl;

$R_2$ is selected from —($C_1$-$C_{30}$)-alkyl, =O, —OH, —$SO_2$, —SO, or —$SOCH_3$; and $R_3$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SH, —$SO_3H$, —CN, —$NH_2$, or a halogen.

Another embodiment provides a compound of Formula II:

Formula II

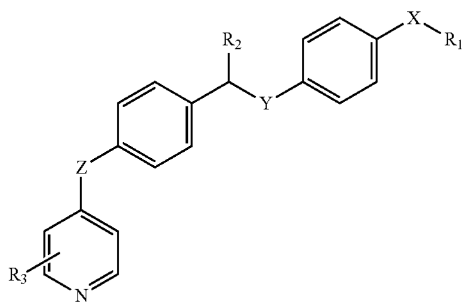

or a pharmaceutically acceptable enantiomer, salt, or solvate thereof, wherein:

$R_1$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —($C_3$-$C_{20}$)-heteroaryl groups optionally substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SH, —$SO_3H$, —CN, —$NH_2$, or a halogen;

X, Y, and Z are independently selected from —O, —NH, —S, —N—($C_1$-$C_{30}$)-alkyl, or —($C_1$-$C_{30}$)-aryl;

$R_2$ is selected from —($C_1$-$C_{30}$)-alkyl, —O, —OH, —$SO_2$, —SO, or —$SOCH_3$; and $R_3$ is selected from —($C_1$-$C_{30}$)-alkyl, —($C_3$-$C_{12}$)-cycloalkyl, —($C_3$-$C_{12}$)-heterocycloalkyl, —($C_6$-$C_{20}$)-aryl, or —$(C_3-C_{20})$-heteroaryl groups optionally substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})\text{-alkyl}]_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SH, —$SO_3H$, —CN, —$NH_2$, or a halogen.

Another embodiment provides a compound of Formula III:

Formula III

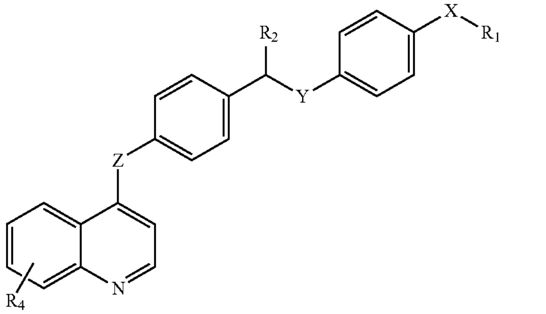

or a pharmaceutically acceptable enantiomer, salt, or solvate thereof, wherein:

$R_1$ is selected from —$(C_1-C_{30})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl groups optionally substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})\text{-alkyl}]2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SH, —$SO_3H$, —CN, —$NH_2$, or a halogen;

X, Y, and Z are independently selected from —O, —NH, —S, —N—$(C_1-C_{30})$-alkyl, or —$(C_1-C_{30})$-aryl;

$R_2$ is selected from —$(C_1-C_{30})$-alkyl, —O, —OH, —$SO_2$, —SO, or —$SOCH_3$; and $R_4$ is selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})\text{-alkyl}]_2$, —$(C_6-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SH, —$SO_3H$, —CN, —$NH_2$, or a halogen.

Still another embodiment provides the compound of Formula IV:

Formula IV

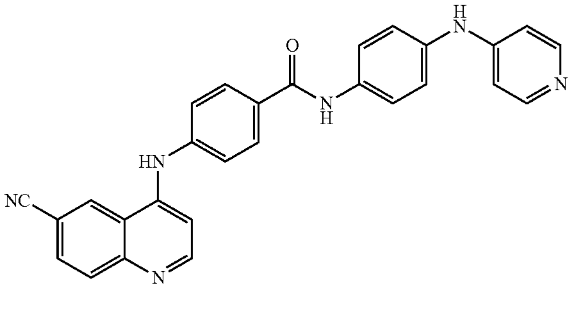

or a pharmaceutically acceptable enantiomer, salt, or solvate thereof.

The compound of Formula IV, also referred to as mJJ64A, and enantiomers, polymorphs, pharmaceutically acceptable salts, and derivatives thereof can be used to induce, promote, or increase Akt3 bioactivity in immune cells.

In some embodiments, the Atk3 activator is a derivative of Formula I, Formula II, Formula III or Formula IV. The term "derivative" or "derivatized" as used herein includes one or more chemical modifications of Formula I, Formula II, Formula III, or Formula IV, or an enantiomer, polymorph, or pharmaceutically acceptable salt thereof. That is, a "derivative" may be a functional equivalent of Formula I, Formula II, Formula III or Formula IV which is capable of inducing the improved pharmacological functional activity and/or behavioral response in a given subject. Illustrative of such chemical modifications would be replacement of hydrogen by a halo group, an alkyl group, an acyl group or an amino group.

The chemical modification of Formula I, Formula II, Formula III, or Formula IV, an enantiomer, polymorph, or pharmaceutically acceptable salt thereof may either enhance or reduce hydrogen bonding interaction, charge interaction, hydrophobic interaction, Van Der Waals interaction or dipole interaction between the compound and its target.

In some embodiments, the compound of Formula I, Formula II, Formula III or Formula IV may act as a model (for example, a template) for the development of other derivative compounds which are a functional equivalent of the compound and which is capable of inducing the improved pharmacological functional activity and/or effect and/or behavioral response in a given subject.

The compound of Formula I, Formula II, Formula III or Formula IV may be a racemic compound and/or optically active isomers thereof. In this regard, some of the compounds can have asymmetric carbon atoms, and therefore, can exist either as racemic mixtures or as individual optical isomers (enantiomers). Compounds described herein that contain a chiral center include all possible stereoisomers of the compound, including compositions including the racemic mixture of the two enantiomers, as well as compositions including each enantiomer individually, substantially free of the other enantiomer. Thus, for example, contemplated herein is a composition including the S enantiomer of a compound substantially free of the R enantiomer, or the R enantiomer substantially free of the S enantiomer. If the named compound includes more than one chiral center, the scope of the present disclosure also includes compositions including mixtures of varying proportions between the diastereomers, as well as compositions including one or more diastereomers substantially free of one or more of the other diastereomers. By "substantially free" it is meant that the composition includes less than 25%, 15%, 10%, 8%, 5%, 3%, or less than 1% of the minor enantiomer or diastereomer (s).

Akt3, also referred to as RAC-gamma serine/threonine-protein kinase is an enzyme that in humans is encoded by the Akt3 gene. Akt kinases are known to be regulators of cell signaling in response to insulin and growth factors and are associated with a broad range of biological processes including cell proliferation, differentiation, apoptosis, tumorigenesis, as well as glycogen synthesis and glucose uptake. Akt3 has been shown to be stimulated by platelet-derived growth factor (PDGF), insulin, and insulin-like growth factor 1 (IGF1).

Akt3 kinase activity mediates serine and/or threonine phosphorylation of a range of downstream substrates. Nucleic acid sequences for Akt3 are known in the art. See, for example, Genbank accession no. AF124141.1: Homo sapiens protein kinase B gamma mRNA, complete cds, which is specifically incorporated by references in its entirety, and provides the nucleic acid sequence:

(SEQ ID NO: 1)

```
AGGGGAGTCATCATGAGCGATGTTACCATTGTGAAGGAAGGTTGGGTTC
AGAAGAGGGGAGAATATATAAAAAACTGGAGGCCAAGATACTTCCTTTT
GAAGACAGATGGCTCATTCATAGGATATAAAGAGAAACCTCAAGATGTG
GATTTACCTTATCCCCTCAACAACTTTTCAGTGGCAAAATGCCAGTTAA
TGAAAACAGAACGACCAAAGCCAAACACATTTATAATCAGATGTCTCCA
GTGGACTACTGTTATAGAGAGAACATTTCATGTAGATACTCCAGAGGAA
AGGGAAGAATGGACAGAAGCTATCCAGGCTGTAGCAGACAGACTGCAGA
GGCAAGAAGAGGAGAGAATGAATTGTAGTCCAACTTCACAAATTGATAA
TATAGGACAGGAAGAGATGGATGCCTCTACAACCCATCATAAAAGAAAG
ACAATGAATGATTTTGACTATTTGAAACTACTAGGTAAAGGCACTTTTG
GGAAAGTTATTTTGGTTCGAGAGAAGGCAAGTGGAAAATACTATGCTAT
GAAGATTCTGAAGAAAGAAGTCATTATTGCAAAGGATGAAGTGGCACAC
ACTCTAACTGAAAGCAGAGTATTAAAGAACACTAGACATCCCTTTTTAA
CATCCTTGAAATATTCCTTCCAGACAAAAGACCGTTTGTGTTTTGTGAT
GGAATATGTTAATGGGGGCGAGCTGTTTTTCCATTTGTCGAGAGAGCGG
GTGTTCTCTGAGGACCGCACACGTTTCTATGGTGCAGAAATTGTCTCTG
CCTTGGACTATCTACATTCCGGAAAGATTGTGTACCGTGATCTCAAGTT
GGAGAATCTAATGCTGGACAAAGATGGCCACATAAAAATTACAGATTTT
GGACTTTGCAAAGAAGGGATCACAGATGCAGCCACCATGAAGACATTCT
GTGGCACTCCAGAATATCTGGCACCAGAGGTGTTAGAAGATAATGACTA
TGGCCGAGCAGTAGACTGGTGGGGCCTAGGGGTTGTCATGTATGAAATG
ATGTGTGGGAGGTTACCTTTCTACAACCAGGACCATGAGAAACTTTTTG
AATTAATATTAATGGAAGACATTAAATTTCCTCGAACACTCTCTTCAGA
```

-continued

```
TGCAAAATCATTGCTTTCAGGGCTCTTGATAAAGGATCCAAATAAACGC
CTTGGTGGAGGACCAGATGATGCAAAAGAAATTATGAGACACAGTTTCT
TCTCTGGAGTAAACTGGCAAGATGTATATGATAAAAAGCTTGTACCTCC
TTTTAAACCTCAAGTAACATCTGAGACAGATACTAGATATTTTGATGAA
GAATTTACAGCTCAGACTATTACAATAACACCACCTGAAAAATATGATG
AGGATGGTATGGACTGCATGGACAATGAGAGGCGGCCGCATTTCCCTCA
ATTTTCCTACTCTGCAAGTGGACGAGAATAAGTCTCTTTCATTCTGCTA
CTTCACTGTCATCTTCAATTTATTACTGAAAATGATTCCTGGACATCAC
CAGTCCTAGCTCTTACACATAGCAGGGGCACCTTCCGACATCCCAGACC
AGCCAAGGGTCCTCACCCCTCGCCACCTTTCACCCTCATGAAAACACAC
ATACACGCAAATACACTCCAGTTTTTGTTTTTGCATGAAATTGTATCTC
AGTCTAAGGTCTCATGCTGTTGCTGCTACTGTCTTACTATTA.
```

Amino acid sequences are also known in the art. See, for example, UniProtKB/Swiss-Prot accession no. Q9Y243 (Akt3_HUMAN), which is specifically incorporated by reference in its entirety and provides the amino acid sequence:

(SEQ ID NO: 2)

```
MSDVTIVKEGWVQKRGEYIKNWRPRYFLLKTDGSFIGYKEKPQDVDLPY
PLNNFSVAKCQLMKTERPKPNTFIIRCLQWTTVIERTFHVDTPEEREEW
TEAIQAVADRLQRQEEERMNCSPTSQIDNIGEEEMDASTTHHKRKTMND
FDYLKLLGKGTFGKVILVREKASGKYYAMKILKKEVIIAKDEVAHTLTE
SRVLKNTRHPFLTSLKYSFQTKDRLCFVMEYVNGGELFFHLSRERVFSE
DRTRFYGAEIVSALDYLHSGKIVYRDLKLENLMLDKDGHIKITDFGLCK
EGITDAATMKTFCGTPEYLAPEVLEDNDYGRAVDWWGLGVVMYEMMCGR
LPFYNQDHEKLFELILMEDIKFPRTLSSDAKSLLSGLLIKDPNKRLGGG
PDDAKEIMRHSFFSGVNWQDVYDKKLVPPFKRQVTSETDTRYFDEEFTA
QTITITPPEKYDEDGMDCMDNERRPHFPQFSYSASGRE.
```

The domain structure of Akt3 is reviewed in Romano, Scientifica, Volume 2013 (2013), Article ID 317186, 12 pages, and includes an N-terminal pleckstrin homology domain (PH), followed by a catalytic kinase domain (KD), and the C-terminal regulatory hydrophobic region. The catalytic and regulatory domains are both important for the biological actions mediated by Akt protein kinases and exhibit the maximum degree of homology among the three Akt isoforms. The PH domain binds lipid substrates, such as phosphatidylinositol (3,4) diphosphate (PIP2) and phosphatidylinositol (3,4,5) triphosphate (PIP3). The ATP binding site is situated approximately in the middle of the catalytic kinase domain, which has a substantial degree of homology with the other components of the AGCkinases family, such as p70 S6 kinase (S6K) and p90 ribosomal S6 kinase (RSK), protein kinase A (PKA) and protein kinase B (PKB). The hydrophobic regulatory moiety is a typical feature of the AGC kinases family. With reference to SEQ ID NO:2, Akt 3 is generally considered to have the following molecule processing and domain structure outlined below.

| Molecule Processing: | | | |
|---|---|---|---|
| Feature key | Position(s) | Length | Description |
| Initiator methionine | 1 | 1 | Removed |
| Chain | 2-479 | 478 | Akt3 |

| Regions: | | | |
|---|---|---|---|
| Feature key | Position(s) | Length | Description |
| Domain | 5-107 | 103 | PH |
| Domain | 148-405 | 258 | Protein kinase |
| Domain | 406-479 | 74 | AGC-kinase C-terminal |
| Nucleotide binding | 154-162 | 9 | ATP |

| Sites: | | | |
|---|---|---|---|
| Feature key | Position(s) | Length | Description |
| Active site | 271 | 1 | Proton acceptor |
| Binding site | 177 | 1 | ATP |

The initiator methionine of SEQ ID NO:2 is disposable for Akt3 function. Therefore, in some embodiments, the compound directly or indirectly inhibits expression or bio-availability of an Akt3 having the amino acid sequence

```
                                      (SEQ ID NO: 3)
SDVTIVKEGWVQKRGEYIKNWRPRYFLLKTDGSFIGYKEKPQDVDLPYP

LNNFSVAKCQLMKTERPKPNTFIIRCLQWTTVIERTFHVDTPEEREEWT

EAIQAVADRLQRQEEERMNCSPTSQIDNIGEEEMDASTTHHKRKTMNDF

DYLKLLGKGTFGKVILVREKASGKYYAMKILKKEVIIAKDEVAHTLTES

RVLKNTRHPFLTSLKYSFQTKDLRCFVMEYVNGGELFFHLSRERVFSED

RTRFYGAEIVSALDYLHSGKIVYRDLKLENLMLDKDGHIKITDFGLCKE

GITDAATMKTFCGTPEYLAPEVLEDNDYGRAVDWWGLGVVMYEMMCGRL

PFYNQDHEKLFELILMEDIKFPRTLSSDAKSLLSGLLIKDPNKRLGGGP

DDAKEIMRHSFFSGVNWQDVYDKKLVPPFKPQVTSETDTRYFDEEFTAQ

TITITPPEKYDEDGMDCMDNERRPHFPQFSYSASGRE.
```

Two specific sites, one in the kinase domain (Thr-305 with reference to SEQ ID NO:2) and the other in the C-terminal regulatory region (Ser-472 with reference to SEQ ID NO:2), need to be phosphorylated for full activation of Akt3. Interaction between the PH domain of Akt3 and TCL1A enhances Akt3 phosphorylation and activation. IGF-1 leads to the activation of Akt3, which may play a role in regulating cell survival.

A. Formulations

Another embodiment provides formulations of and pharmaceutical compositions including one or more of compounds according to Formulas I, II, III, IV, or an enantiomer, polymorph, or pharmaceutically acceptable salt thereof. Generally, dosage levels, for the compounds disclosed herein are between about 0.0001 mg/kg of body weight to about 1,000 mg/kg, more preferably of 0.001 to 500 mg/kg, more preferably 0.01 to 50 mg/kg of body weight daily are administered to mammals.

1. Delivery Vehicles

Compounds of Formulas I, II, III, and IV can be administered to a subject, preferably a human subject, where it is taken up into the cells of a subject with or without the aid of a delivery vehicle. Appropriate delivery vehicles for the disclosed active agents are known in the art and can be selected to suit the particular active agent. For example, in some embodiments, the compound is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly (lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

In some embodiments, compounds according to Formula I, Formula II, Formula III, or Formula IV, or an enantiomer, polymorph, or pharmaceutically acceptable salt thereof and a second therapeutic agent are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

The compounds according to Formula I, Formula II, Formula III, or Formula IV, or an enantiomer, polymorph, or pharmaceutically acceptable salt thereof can be incorporated into a delivery vehicle prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C. The release point and/or period of release can be varied as discussed above.

2. Pharmaceutical Compositions

Pharmaceutical compositions including compounds according to Formula I, Formula II, Formula III or Formula IV with or without a delivery vehicle are provided. Pharmaceutical compositions can be formulated for administration by parenteral (intramuscular, intraperitoneal, intravenous (IV) or subcutaneous injection), enteral, transmucosal (nasal, vaginal, rectal, or sublingual), or transdermal (either passively or using iontophoresis or electroporation) routes of administration or using bioerodible inserts and can be formulated in dosage forms appropriate for each route of administration.

In certain embodiments, the compositions are administered locally, for example by injection directly into a site to be treated (e.g., into a tumor). In some embodiments, the compositions are injected or otherwise administered directly into the vasculature onto vascular tissue at or adjacent to the intended site of treatment (e.g., adjacent to a tumor). Typically, local administration causes an increased localized concentration of the composition which is greater than that which can be achieved by systemic administration.

a. Formulations for Parenteral Administration

Compounds according to Formula I, Formula II, Formula III, or Formula IV, or an enantiomer, polymorph, or pharmaceutically acceptable salt thereof and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Enteral Formulations

Compounds according to Formula I, Formula II, Formula III, or Formula IV, or an enantiomer, polymorph, or pharmaceutically acceptable salt thereof can formulated for enteral administration. Suitable oral dosage forms of compounds of Formula I, Formula II, Formula III, or Formula IV, or an enantiomer, polymorph, or pharmaceutically acceptable salt thereof include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the trade name Eudragit®. In further preferred embodiments, the acrylic polymer comprises a mixture of two acrylic resin lacquers commercially available from Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules, etc. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

c. Formulations for Pulmonary and Mucosal Administration

Active agent(s) and compositions thereof can be applied formulated for pulmonary or mucosal administration. The administration can include delivery of the composition to the lungs, nasal, oral (sublingual, buccal), vaginal, or rectal mucosa.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, CA).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter, and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

d. Transdermal

Transdermal formulations may also be prepared. These will typically be ointments, lotions, sprays, or patches, all of which can be prepared using standard technology. Transdermal formulations can include penetration enhancers.

III. Methods of Selectively Activating Akt3

The disclosed compositions for selectively activating Akt3 can be used to modulate an immune response by decreasing a suppressive function of nTregs. In some embodiments, compounds according to Formula I, Formula II, Formula III, or Formula IV, or an enantiomer, polymorph, or pharmaceutically acceptable salt thereof is administered systemically. In other embodiments, compounds according to Formula I, Formula II, Formula III, or Formula IV, or an enantiomer, polymorph, or pharmaceutically acceptable salt thereof is administered locally or regionally. For example, in some embodiments, compositions containing compounds according to Formula I, Formula II, Formula III, or Formula IV, or an enantiomer, polymorph, or pharmaceutically acceptable salt thereof are delivered to or specifically target the tissue or organs in need of modulation. Tregs can be modulated by targeting or delivering the compositions to the lymph nodes. nTregs can be modulated by targeting or specifically delivering the compositions to the thymus or spleen. iTregs can be modulated by targeting or specifically delivering the compositions to conventional T cells outside the thymus.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. Exemplary symptoms, pharmacologic, and physiologic effects are discussed in more detail below.

In some embodiments, the effect of the composition on a subject is compared to a control. For example, the effect of the composition on a particular symptom, pharmacologic, or physiologic indicator can be compared to an untreated subject or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based measuring the symptom, pharmacologic, or physiologic indicator in one or more subjects that do not have the disease or condition to be treated (e.g., healthy subjects). In some embodiments, the effect of the treatment is compared to a conventional treatment that is known the art. For example, if the disease to be treated is cancer, a conventional treatment could a chemotherapeutic agent.

In some embodiments, the immune modulating compositions disclosed herein are administered in combination with one or more additional active agents. The combination therapies can include administration of the active agents together in the same admixture, or in separate admixtures. Therefore, in some embodiments, the pharmaceutical composition includes two, three, or more active agents. The pharmaceutical compositions can be formulated as a pharmaceutical dosage unit, referred to as a unit dosage form. Such formulations typically include an effective amount of one or more of the disclosed immune modulating compounds. The different active agents can have the same, or different mechanisms of action. In some embodiments, the combination results in an additive effect on the treatment of the disease or disorder. In some embodiments, the combinations result in a more than additive effect on the treatment of the disease or disorder.

Preferably, the disclosed compounds and methods of use specifically activate the activity of Akt3 without increasing or decreasing the activity of Akt1, Akt2, or the combination thereof.

A. Increasing Immune Suppressive Responses and Decreasing Immune Stimulatory Responses 1. Methods of Treatment The disclosed compounds or an enantiomer, polymorph, or pharmaceutically acceptable salt thereof are useful as therapeutic agents. Immune cells, preferably T cells, can be contacted in vivo or ex vivo with compounds according to Formula I, Formula II, Formula III, or Formula IV, or an enantiomer, polymorph, or pharmaceutically acceptable salt thereof to decrease or inhibit immune responses including, but not limited to inflammation. The T cells contacted with compounds according to Formula I, Formula II, Formula III, or Formula IV, or an enantiomer, polymorph, or pharmaceutically acceptable salt thereof can be any immune cell that expresses Akt3 or has Akt3 activity and has the ability to become Foxp3+. Exemplary immune cells that can be treated with the compounds according to Formula I, Formula II, Formula III, or Formula IV, or an enantiomer, polymorph, or pharmaceutically acceptable salt thereof include, but are not limited to regulatory cells such as ThI, TcI, Th25 Tc2, Th3, ThI 7, Th22, Treg, nTreg, iTreg, and TrI cells and cells that secrete, or cause other cells to secrete, inflammatory molecules, including, but not limited to, IL-Iβ, TNF-α, TGF-beta, IFN-γ, IL-17, IL-6, IL-23, IL-22, IL-21, and MMPs. The disclosed compounds or an enantiomer, polymorph, or pharmaceutically acceptable salt thereof can also be used to increase or promote the activity or production of Tregs, increase the production of cytokines such as IL-10 from Tregs, increase the differentiation of Tregs, increase the number of Tregs, or increase the survival of Tregs.

The disclosed compounds or an enantiomer, polymorph, or pharmaceutically acceptable salt thereof can be used to increase expression of FoxP3 on immune cells.

One embodiment provides a method of increasing an immune suppressive response in subject in need thereof by contacting immune cells ex vivo with the disclosed compounds, or an enantiomer, polymorph, or pharmaceutically acceptable salt thereof, in an amount effective to increase expression of FoxP3 on the immune cells, and administering the contacted immune cells to the subject. In one embodiment, the immune cells are autologous immune cells. The immune cells can include T cells including but not limited to Tregs and iTregs.

In some embodiments, the disclosed compounds or an enantiomer, polymorph, or pharmaceutically acceptable salt thereof are administered in combination with a second therapeutic. Combination therapies may be useful in immune modulation. In some embodiments, the disclosed compounds or an enantiomer, polymorph, or pharmaceutically acceptable salt thereof can be used to attenuate or reverse the activity of a pro-inflammatory drug, and/or limit the adverse effects of such drugs.

B. Methods of Treating Inflammatory Responses

One embodiment provides methods for treating or alleviating one or more symptoms of inflammation. In a more preferred embodiment, the compositions according to Formula I, Formula II, Formula III or Formula IV and disclosed methods are useful for treating chronic and persistent inflammation. Inflammation in general can be treated using the compounds according to Formula I, Formula II, Formula III, or Formula IV, or an enantiomer, polymorph, or pharmaceutically acceptable salt thereof.

An immune response including inflammation can be inhibited or reduced in a subject, preferably a human, by administering an effective amount disclosed compounds or an enantiomer, polymorph, or pharmaceutically acceptable salt thereof to increase or promote the biological activity Akt3 in an immune cell, reduce the amounts of proinflammatory molecules at a site of inflammation, induce or increase expression of FoxP3, induce or increase the proliferation of iTregs, or combinations thereof. Exemplary proinflammatory molecules include, but are not limited to, IL-1B, TNF-α, TGF-beta, IFN-γ, IL-17, IL-6, IL-23, IL-22, IL-21, and MMPs.

Compounds according to Formula I, Formula II, Formula III, or Formula IV, or an enantiomer, polymorph, or pharmaceutically acceptable salt thereof can cause Tregs to have an enhanced suppressive effect on an immune response. Tregs can suppress differentiation, proliferation, activity, and/or cytokine production and/or secretion by Th1, Th17, Th7, Th22, and/or other cells that secrete, or cause other cells to secrete, inflammatory molecules, including, but not limited to, IL-Iβ, TNF-α, TGF-beta, IFN-γ, IL-17, IL-6, IL-23, IL-22, IL-21, and MMPs. For example, compounds according to Formula I, Formula II, Formula III, or Formula IV, or an enantiomer, polymorph, or pharmaceutically acceptable salt thereof can cause Tregs to have an enhanced suppressive effect on Th1 and/or Th 17 cells to reduce the level of IFN-γ and IL-17 produced, respectively. The disclosed compounds or an enantiomer, polymorph, or pharmaceutically acceptable salt thereof can also act directly on Tregs to promote or enhance production of IL-10 to suppress the Th1 and Th 17 pathway, or to increase the number of Tregs.

1. Diseases to Treat

Compositions containing the disclosed compounds or an enantiomer, polymorph, or pharmaceutically acceptable salt thereof that selectively increase Akt3 activity or expression can be used to decrease an immune stimulatory response in subject. In some embodiments, the subjects have an inflammatory disease including but not limited to autoimmune disease.

Representative inflammatory or autoimmune diseases and disorders that may be treated using disclosed compounds or an enantiomer, polymorph, or pharmaceutically acceptable salt thereof or compositions containing the disclosed compounds or an enantiomer, polymorph, or pharmaceutically acceptable salt thereof include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, obesity, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

2. Combination Therapies

The disclosed compounds or an enantiomer, polymorph, or pharmaceutically acceptable salt thereof and compositions thereof can be used alone or in combination with additional therapeutic agents. The disclosed compounds can be administered together or in alternation with additional therapeutic agents. The additional therapeutic agents include, but are not limited to, immunosuppressive agents (e.g., antibodies against other lymphocyte surface markers (e.g., CD40, alpha-4 integrin) or against cytokines), other fusion proteins (e.g., CTLA-4-Ig, abatacept (Orencia®), TNF-α blockers such as TNFR-Ig, etanercept (Enbrel®)), infliximab (Remicade®), certolizumab (Cimzia®) and adalimumab (Humira®), cyclophosphamide (CTX) (i.e., Endoxan®, Cytoxan®, Neosar®, Procytox®, Revimmune™), methotrexate (MTX) (i.e., Rheumatrex®, Trexall®), belimumab (i.e., Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

Additional immunosuppressive agents include, but are not limited to prednisone, budesonide, prednisolone, cyclosporine, tacrolimus, sirolimus, everolimus, azathioprine, leflunomide, mycophenolate, anakinra, golimumab, ixekizumab, natalizumab, rituximab, secukinumab, tocilizumab, ustekinumab, vedolizumab, basiliximab, daclizumab, muromonab, or combinations thereof.

One embodiment provides an additional therapeutic agent that functions to inhibit or reduce T cell activation through a separate pathway. In one such embodiment, the additional therapeutic agent is a CTLA-4 fusion protein, such as CTLA-4-Ig (abatacept). CTLA-4-Ig fusion proteins compete with the co-stimulatory receptor, CD28, on T cells for binding to CD80/CD86 (B7-1/B7-2) on antigen presenting cells, and thus function to inhibit T cell activation. In another embodiment, the additional therapeutic agent is a CTLA-4-Ig fusion protein known as belatacept. Belatacept contains two amino acid substitutions (L104E and A29Y) that markedly increase its avidity to CD86 in vivo. In another embodiment, the additional therapeutic agent is Maxy-4.

In another embodiment, the second therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. In a another embodiment, compounds of Formula I or an enantiomer, polymorph, or pharmaceutically acceptable salt thereof and CTX are co-administered in effective amount to inhibit, reduce, or treat a chronic autoimmune disease or disorder such as Systemic lupus erythematosus (SLE).

In another embodiment, the second therapeutic agent preferentially treats chronic inflammation, whereby the treatment regimen targets both acute and chronic inflammation.

In another embodiment, the compositions according to Formula I, Formula II, Formula III, or Formula IV, or an enantiomer, polymorph, or pharmaceutically acceptable salt thereof are used in combination, alternation, or succession with compounds that increase Treg activity or production. Exemplary Treg enhancing agents include but are not limited to glucocorticoid fluticasone, salmeteroal, antibodies to IL-12, IFN-γ, and IL-4; vitamin D3, and dexamethasone, and combinations thereof.

Antibodies to other proinflammatory molecules can also be used in combination or alternation with the disclosed compounds according to Formula I, Formula II, Formula III, or Formula IV, or an enantiomer, polymorph, or pharmaceutically acceptable salt thereof, fusion proteins, or fragments thereof. Preferred antibodies bind to IL-6, IL-23, IL-22 or IL-21.

Another embodiment provides a method for treating transplant rejection by administering to a subject in need thereof and effective amount of the disclosed compounds according to Formula I, Formula II, Formula III, or Formula IV, or an enantiomer, polymorph, or pharmaceutically acceptable salt thereof to increase expression of FoxP3 on immune cells.

Another embodiment provides a method of treating Graft-Versus-Host disease by administering to a subject in need thereof an effective amount of the disclosed compounds according to Formula I, Formula II, Formula III, or Formula IV, or an enantiomer, polymorph, or pharmaceutically acceptable salt thereof to increase expression of FoxP3 on immune cells.

Still another embodiment provides a method for inhibiting or reducing transplant rejection in a host in need thereof by administering to a subject in need thereof and effective amount of the disclosed compounds or an enantiomer, polymorph, or pharmaceutically acceptable salt thereof to increase expression of FoxP3 on immune cells.

Another embodiment provides a method for treating chronic infection by administering to a subject in need thereof and effective amount of the disclosed compounds according to Formula I, Formula II, Formula III, or Formula IV, or an enantiomer, polymorph, or pharmaceutically acceptable salt thereof to increase expression of FoxP3 on immune cells.

One embodiment provides a method for treating obesity by administering to a subject in need thereof an effective amount of the disclosed compounds according to Formula I, Formula II, Formula III, or Formula IV, or an enantiomer, polymorph, or pharmaceutically acceptable salt thereof to increase Akt3 activity. Without being bound by any one theory, it is believed that Akt3 regulates adipogenesis and that dysregulation of Akt3 signaling can lead to increased adipogenesis, obesity, and insulin resistance.

IV. Kits

Medical kits are also disclosed. The medical kits can include, for example, a dosage supply of the disclosed compounds or an enantiomer, polymorph, or pharmaceutically acceptable salt thereof or compositions thereof. The disclosed compounds or an enantiomer, polymorph, or pharmaceutically acceptable salt thereof or compositions thereof can be supplied alone (e.g., lyophilized), or in a pharmaceutical composition. The disclosed compounds or an enantiomer, polymorph, or pharmaceutically acceptable salt thereof or compositions thereof can be in a unit dosage, or in a stock that should be diluted prior to administration. In some embodiments, the kit includes a supply of pharmaceutically acceptable carrier. The kit can also include devices for administration of the active agent(s) or composition(s), for example, syringes and needles. The kits can include printed instructions for administering the disclosed compounds in a use as described above.

EXAMPLES

Example 1: mJJ64A Significantly Increases Expression of FoxP3 on iTregs

Results

The data show mJJ64A significantly increased expression of FoxP3 on iTregs and slightly increased proliferation of iTregs (FIGS. 2A-2H).

Figure 3A:
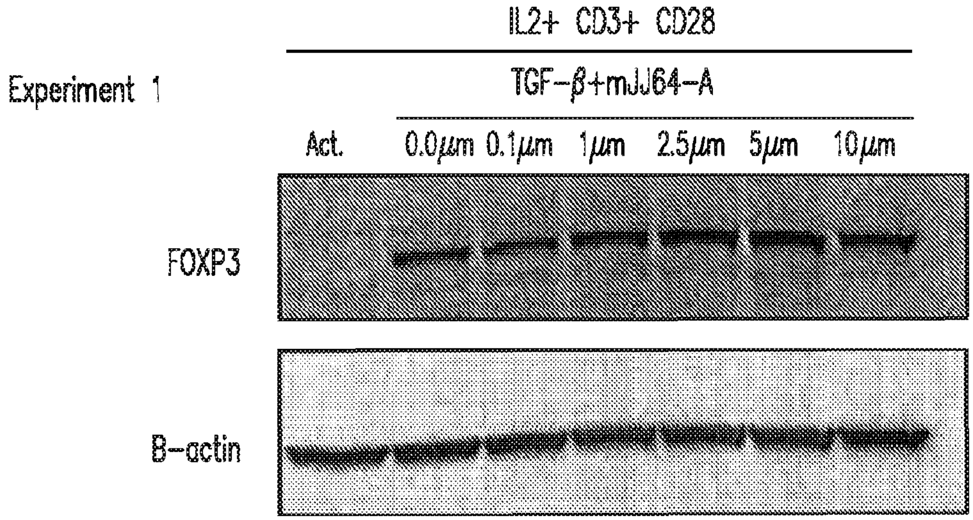
FIG. 3A is an autoradiograph of a Western Blot showing Foxp3 expression in iTregs induction and treatment with the indicated amount of mJJ64A. β-actin serves as the control.
Figure 3B:
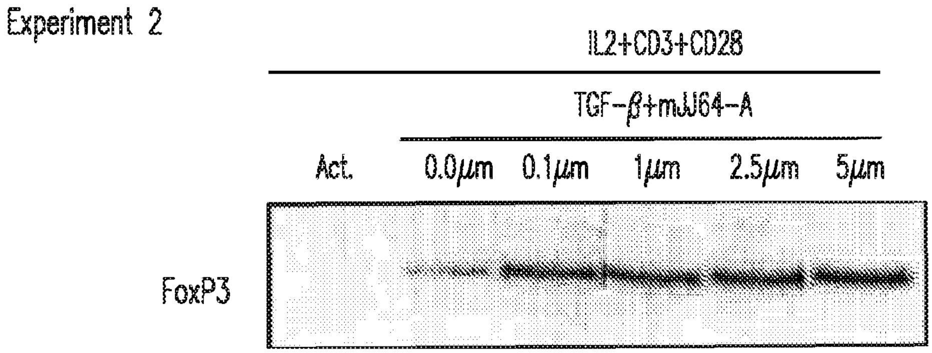
FIG. 3B is a repeat of the experiment in FIG. 3A.

Example 2: mJJ64A Increases FoxP3 Expression When Added During iTreg Induction Results The data show that mJJ64A increased FoxP3 expression when added during iTreg induction (FIGS. 3A and 3B).

Figure 4A:
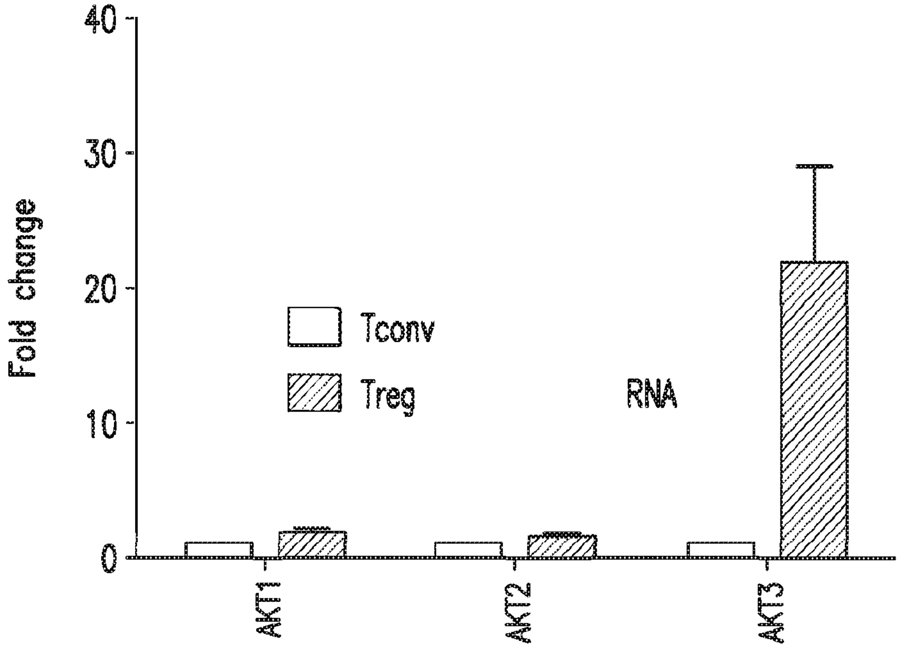
FIG. 4A is a bar graph representing the expression of three isoforms of Akt (Akt1, Akt2, and Akt3) in Tconv (gray bar) and Treg (black bar) cells.
Figure 4B:
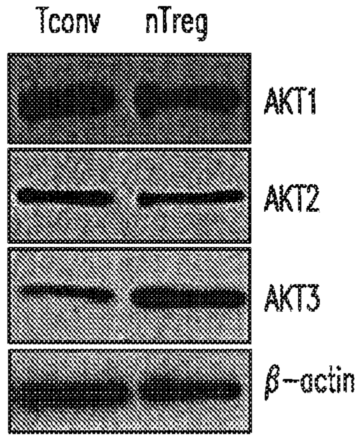
FIG. 4B is a western blot showing the expression of Akt1, Akt2, and Akt3 in Tconv and Treg cells. β-actin serves as a loading control.
Figure 4C:
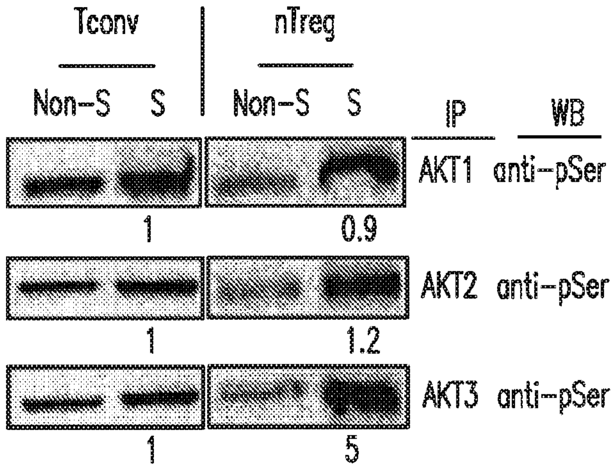
FIG. 4C is a western blot showing pSer expression in an IP pulldown of Akt1, Akt2, or Akt3 in non-stimulated or stimulated Tconv and nTreg cells.
Figure 4D:
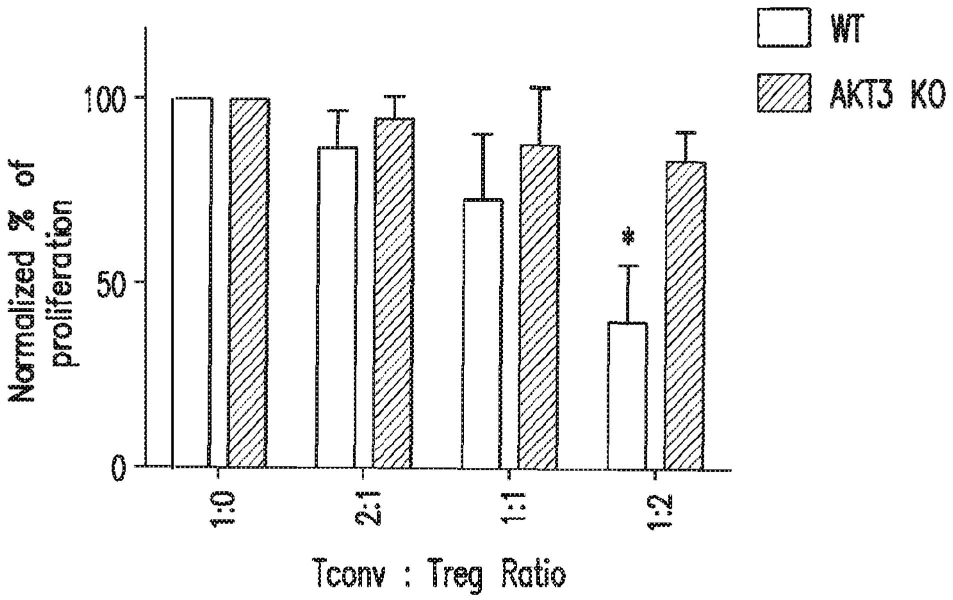
FIG. 4D is a bar graph showing suppressive activity of Tregs from WT (gray bar) and Akt3 KO (black bar) mice. The X-axis represents Tconv to Treg ratio. The Y-axis represents normalized percent of proliferation.
Figure 4E:
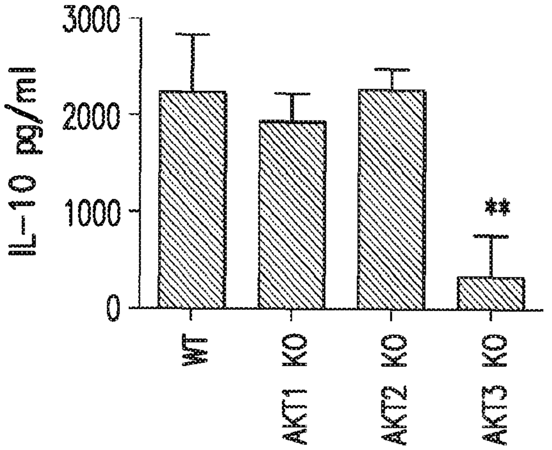
FIG. 4E is a bar graph representing IL-10 levels (pg/ml) in Tregs from WT, Akt1 KO, Akt2 KO, or Akt3 KO mice.
Figure 4F:
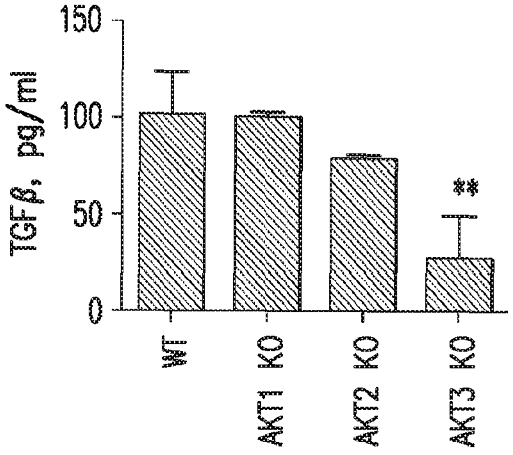
FIG. 4F is a bar graph representing TGFβ levels (pg/ml) in Tregs from WT, Akt1 KO, Akt2 KO, or Akt3 KO mice.
Figure 5A:
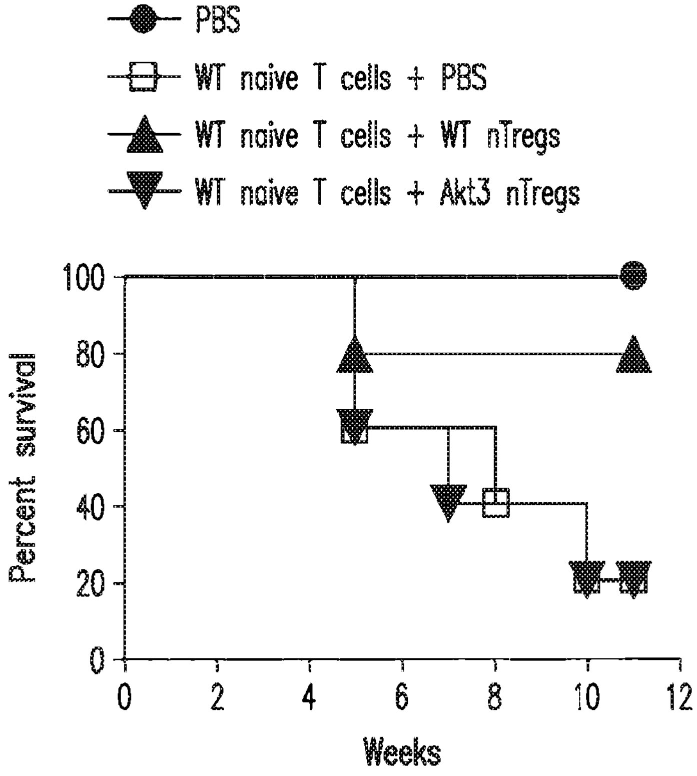
FIG. 5A is a line graph representing percent survival of RAG colitis mice treated with PBS (●), WT naïve T cells+PBS (□), WT naïve T cells+WT nTregs (▲), or WT naïve T cells+Akt3 nTregs (▼).
Figure 5B:
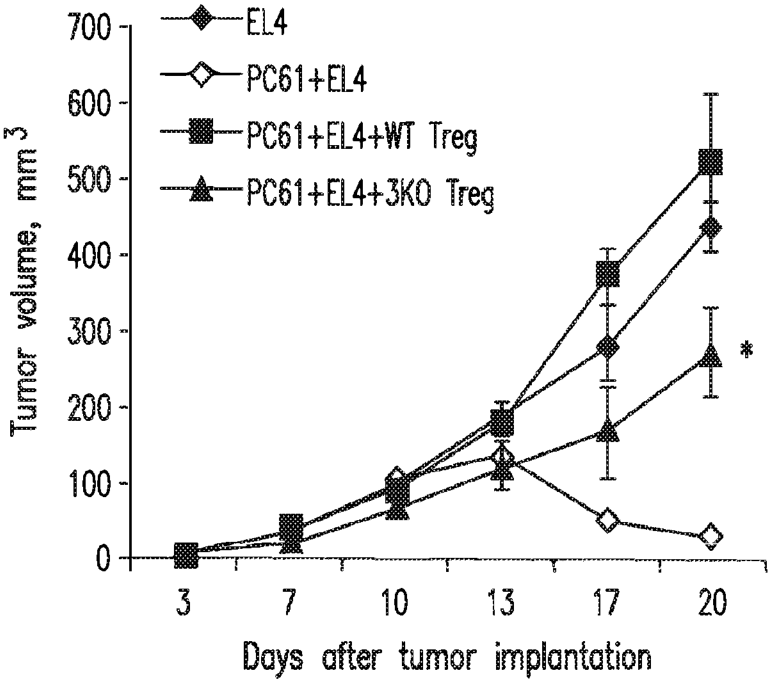
FIG. 5B is a line graph representing tumor volume ($mm^3$) over time (days) in mice with adoptive transfer of EL4 (♦), PC61+EL4 (◇), PC61+EL4+WT Treg (■), or PC61+EL4+Akt3 KO Treg (▲).

Example 3: Akt3 Specifically Regulates Both Types of Tregs, nTregs and iTregs Results The data show that Akt3 is the key regulator of nTregs (FIG. 4A-4F). The suppressive activity of Tregs from Akt3 KO mice was due to decreased levels of inhibitory cytokines IL-10 and TGFβ (FIGS. 4E and 4F). The data also show that in the absence of Akt3, but not other isoforms, the suppressive activity of Tregs was impaired in vivo (FIG. 5A-5B). Tregs from Akt3 KO mice showed impaired suppressive activity in a RAG colitis model (FIG. 5A). Additionally, the adoptive transfer of Tregs from Akt3 KO mice into Treg-depleted tumor-bearing mice show impaired suppression of anti-tumor immunity (FIG. 5B).

Figure 6A:
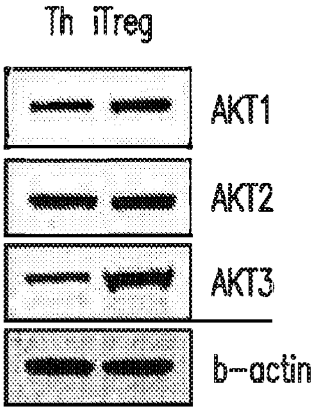
FIG. 6A is a western blot showing expression of Akt1, Akt2, and Akt3 in Th and iTreg cells. β-actin is used as a loading control.
Figure 6B:
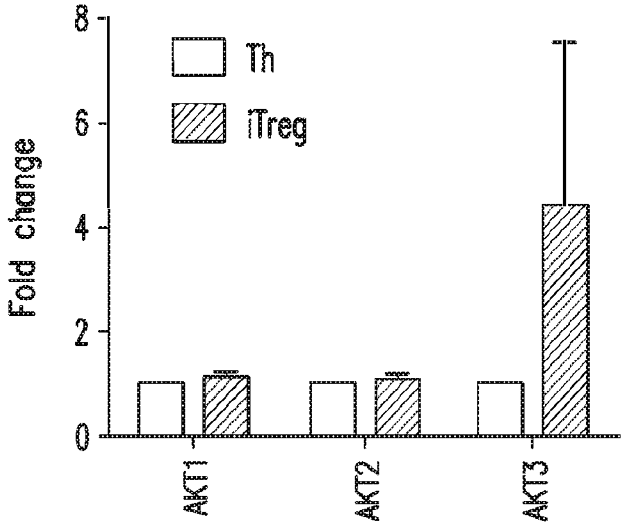
FIG. 6B is a bar graph representing RNA expression of Akt1, Akt2, and Akt3 in Th (gray bar) and iTreg (black bar) cells.
Figure 6C:
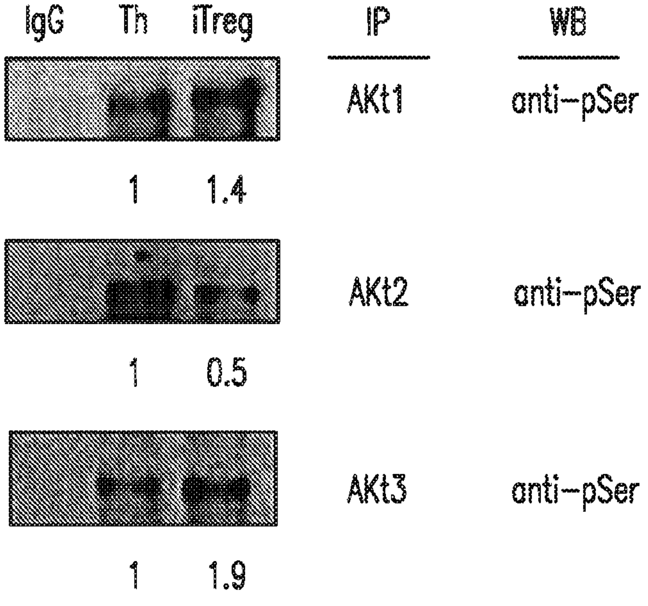
FIG. 6C is a western blot showing pSer expression in Th or Treg cells after IP pulldown of Akt1, Akt2, or Akt3.
Figure 6D:
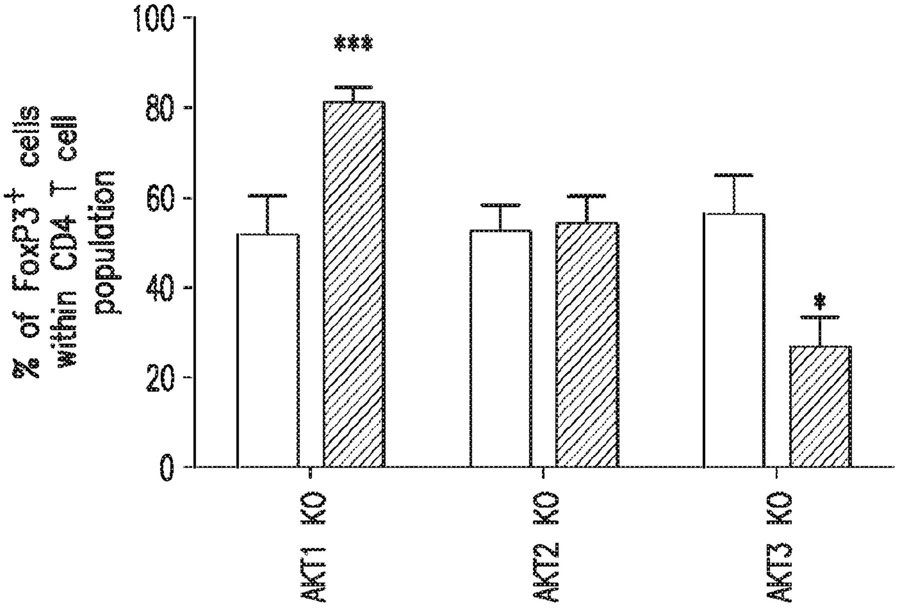
FIG. 6D is a bar graph showing the percent of $FoxP3^+$ cells within CD4 T cell population in Th (gray bar) and iTreg (black bar) cells in Akt1 KO mice, Akt2 KO mice and Akt3 KO mice.
Figure 6E:
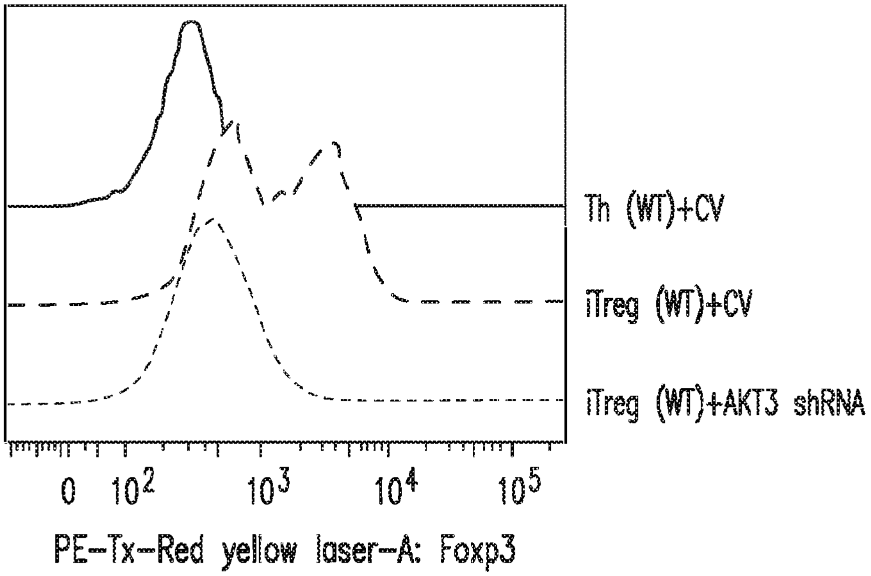
FIG. 6E is a histogram showing FoxP3 induction in Tconvs in response to TGFβ in Th (WT)+CV (solid line), iTreg (WT)+CV (dotted line), and iTreg (WT)+Akt3 shRNA (dashed line).
Figure 7A:
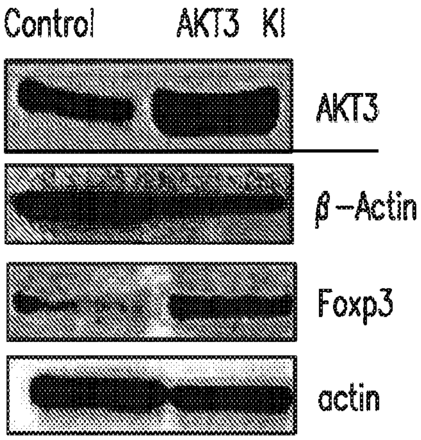
FIG. 7A is a western blot showing Akt3 and FoxP3 expression in control and Akt3 knock-in Tregs. β-actin is used as a loading control.
Figure 7B:
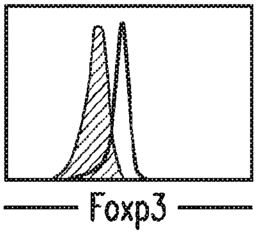
FIG. 7B is a histogram showing FoxP3 expression.
Figure 7C:
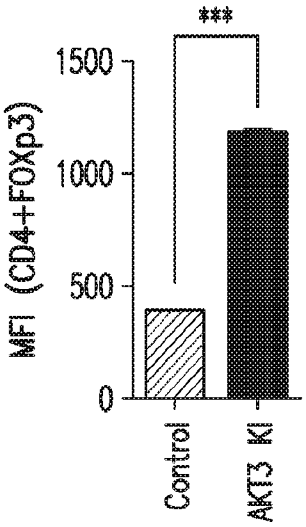
FIG. 7C is a bar graph showing MFI (CD4+FoxP3) in control and Akt3 KI Tregs.
Figure 7D:
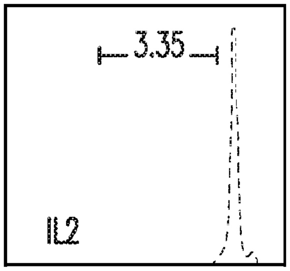
FIG. 7D-I shows histograms representing expression of IL2 and actin in control and Akt3 KI Tregs.
Figure 7E:
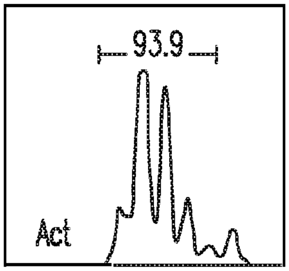
Figure 7F:
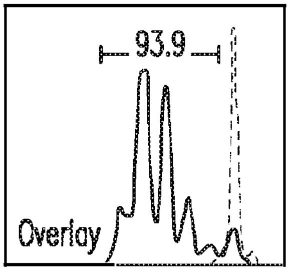
Figure 7G:
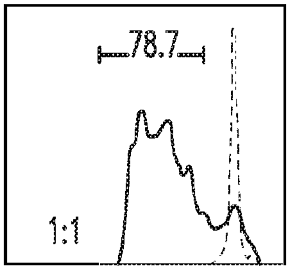
Figure 7H:
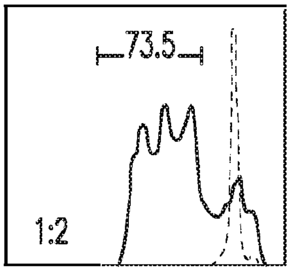
Figure 7I:
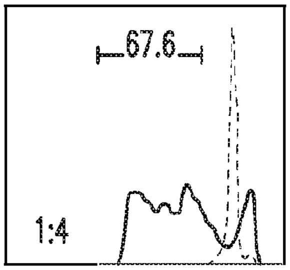

The data also showed that Akt3 was the key regulator of iTregs (FIG. 6A-6E). Akt3 RNA, protein, and Akt3 phosphorylation were upregulated in iTregs (FIG. 6A-6C). In Akt3 KO mice the conversion of Tconv cells into iTregs was significantly inhibited (FIG. 6D). In addition, knocking down Akt3 from WT Tconv cells abrogated FoxP3 induction in response to TGFβ (FIG. 6E).

FIG. 7A-I show that Akt3 knock-in was sufficient to induce Tregs as shown by FoxP3 activation.

Figure 8:
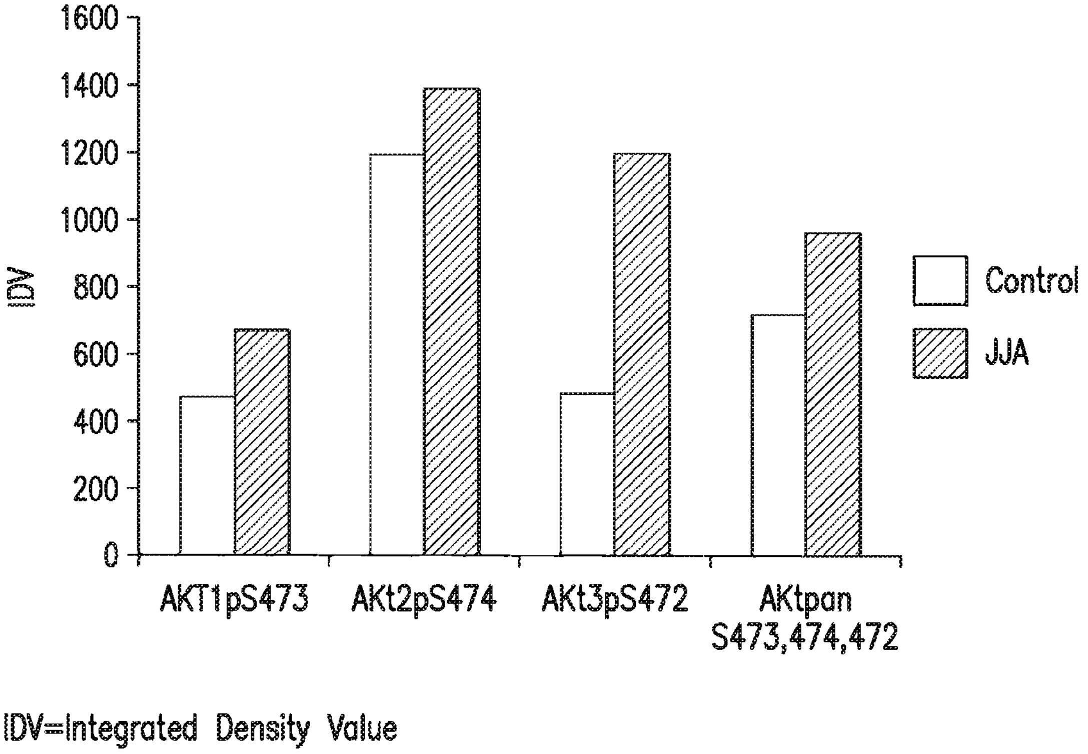
FIG. 8 is a bar graph showing the effect of mJJ64A on the expression of Akt1 pS473, Akt2 pS474, Akt3 pS472, and Akt pan S473,474,472 in A2780 cells compared to control. The Y axis represents integrated density value.

Example 4: mJJ64A Increases Akt3 Phosphorylation in Human Ovarian Carcinoma Cells Results The data show that mJJ64A significantly increases the phosphorylation of Akt3, but not Akt1 or Akt2 in human ovarian carcinoma cells (FIG. 8)

Figure 9A:
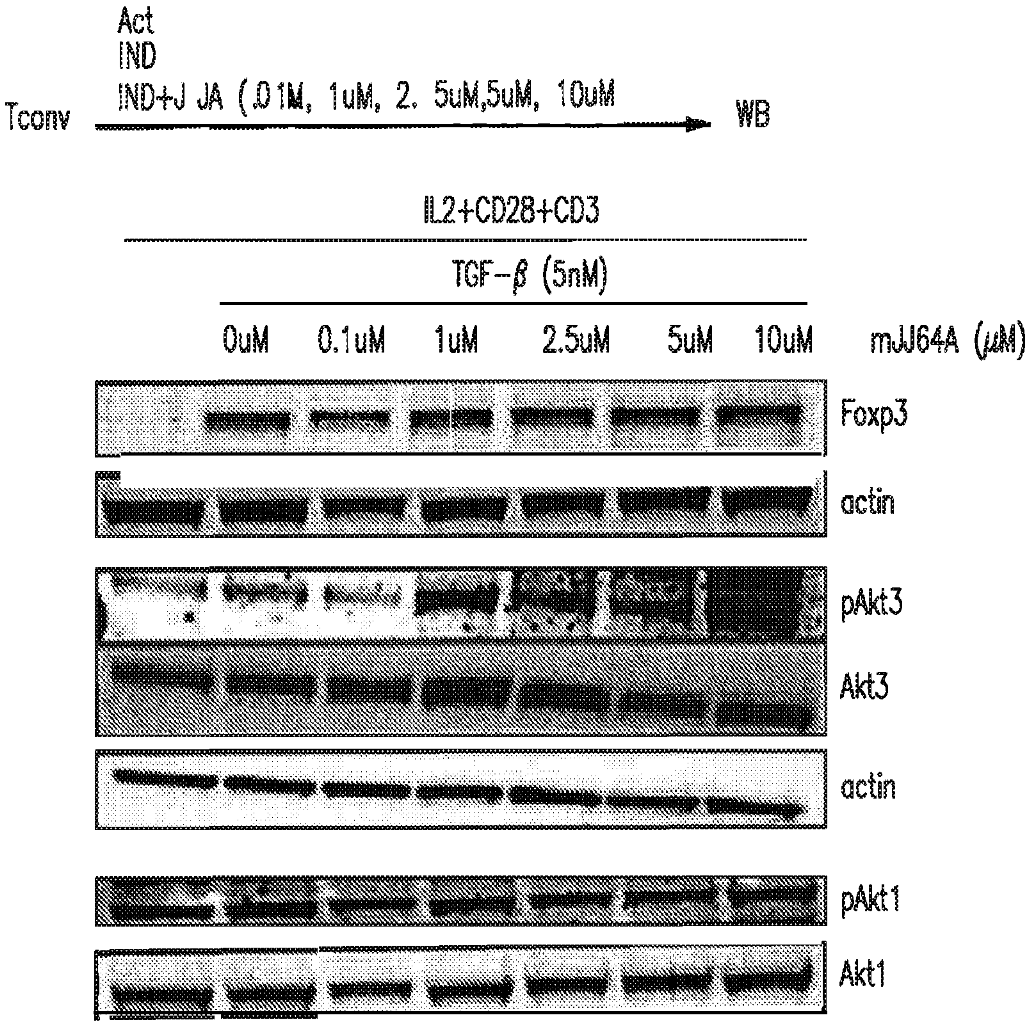
FIG. 9A is a western blot showing the expression of FoxP3, pAkt3, Akt3, pAkt1, and Akt1 in activated Tconv cells induced with TGF-β and treated with various concentrations of mJJ64A.
Figure 9B:
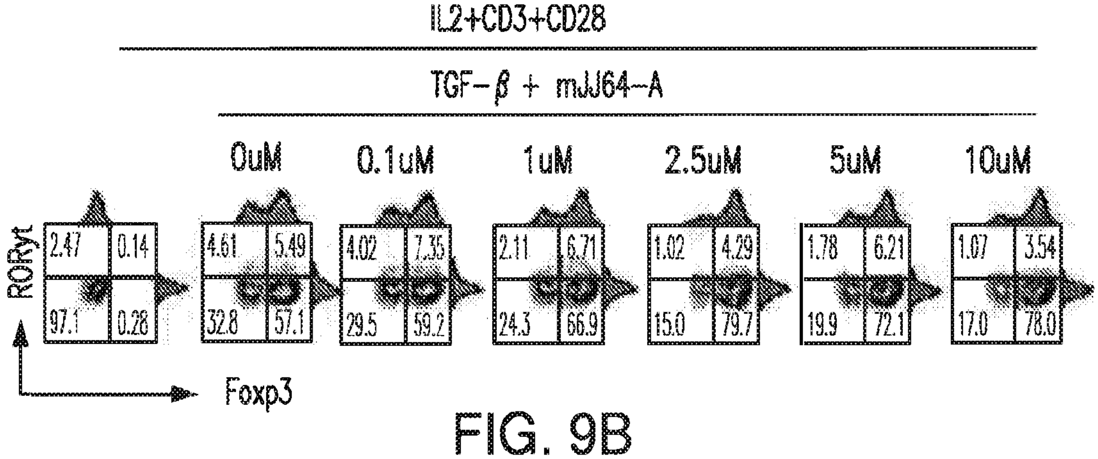
FIG. 9B is a histogram showing the expression of RORγt and FoxP3 in activated iTregs induced with TGF-β and treated with various concentrations of mJJ64A.
Figure 9C:
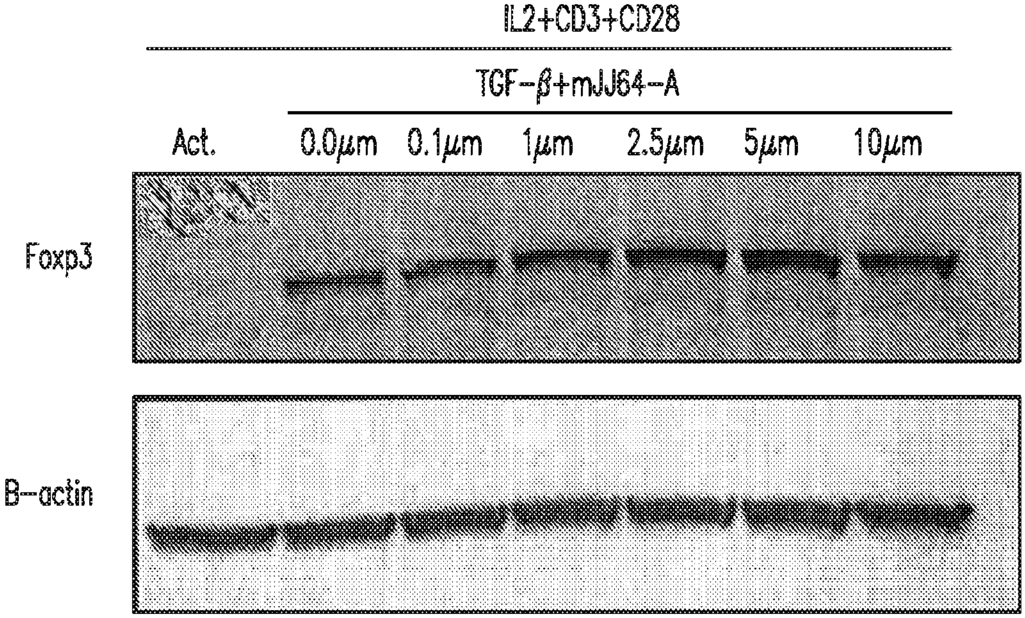
FIG. 9C is a western blot showing FoxP3 expression in activated iTregs induced with TGF-β treated with various concentrations of mJJ64A.

Example 5: mJJ64A Enhances FoxP3 and Akt3 in Tconv Cells During iTreg Induction Results The data show that mJJ64A treatment increased the expression of FoxP3 and Akt3 in Tconv cells during iTreg induction (FIG. 9A-9B).

Example 6: mJJ64A Increases Proliferation of iTregs and nTregs

Figure 10A:
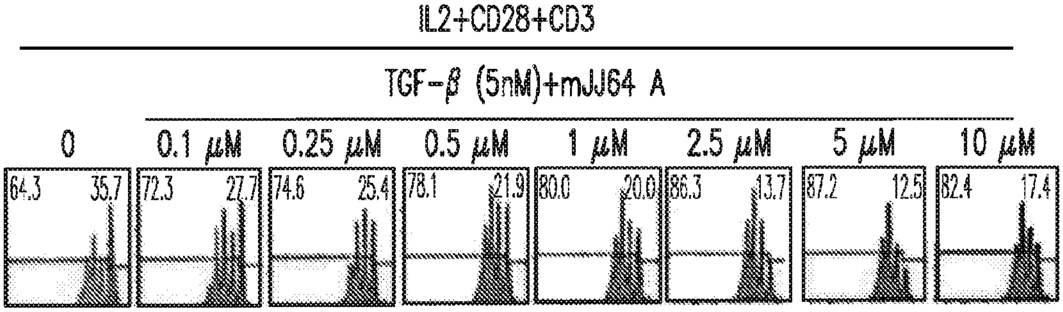
FIG. 10A shows histograms representing proliferation of activated iTregs induced with TGF-β and treated with various concentrations of mJJ64A.
Figure 10B:
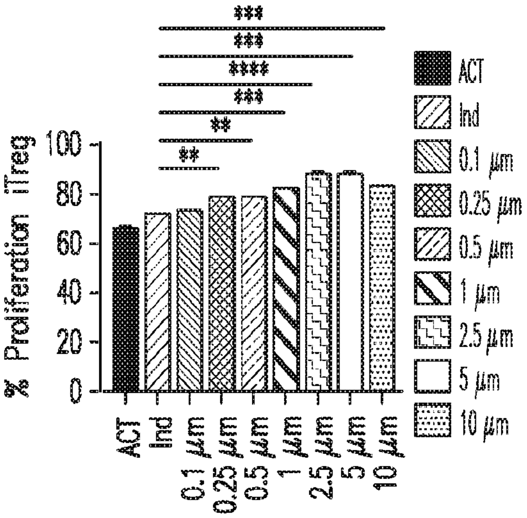
FIG. 10B is a bar graph showing percent proliferation of iTregs treated with various concentrations of mJJ64A. The X-axis represents concentration of mJJ64A. The Y-axis represents percent proliferation.
Figure 10C:
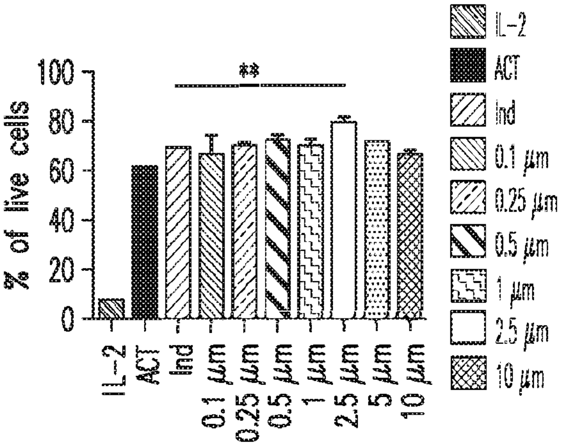
FIG. 10C is a bar graph showing the percent of live cells in iTregs treated with various concentrations of mJJ64A. The X axis represents treatment and the Y axis represents percentage of live cells.
Figure 10D:
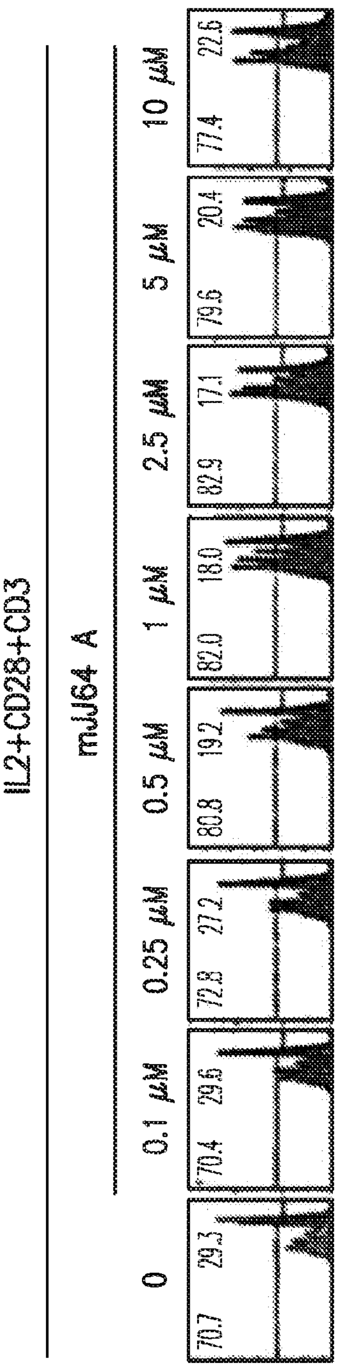
FIG. 10D is a set of histograms showing proliferation of activated nTregs treated with various concentrations of mJJ64A.
Figure 10E:
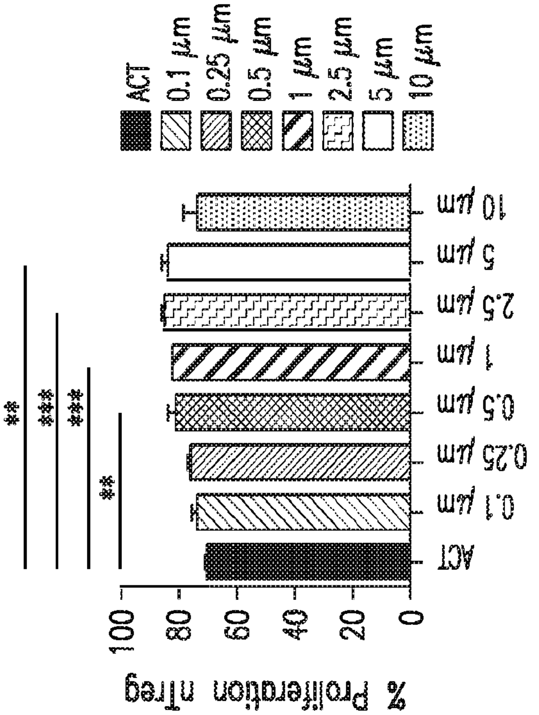
FIG. 10E is a bar graph showing percent proliferation of nTregs treated with various concentrations of mJJ64A. The X-axis represents treatment and the Y-axis represents percent proliferation.
Figure 10F:
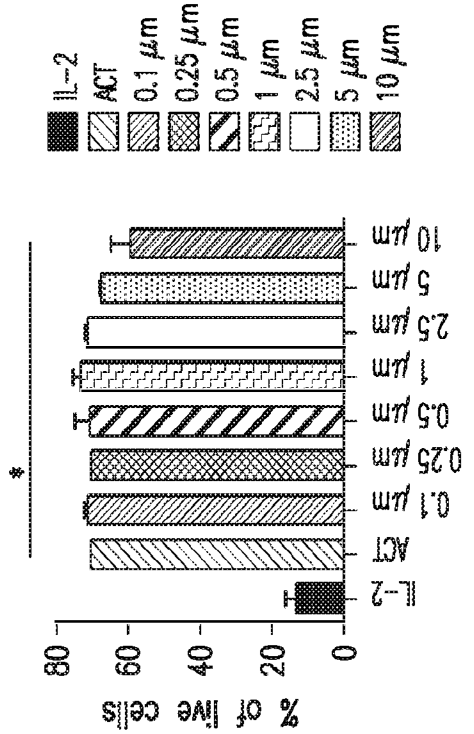
FIG. 10F is a bar graph showing the percent of live cells in nTregs treated with various concentrations of mJJ64A. The X-axis represents treatment and the Y-axis represents percentage of live cells.
Figure 10G:
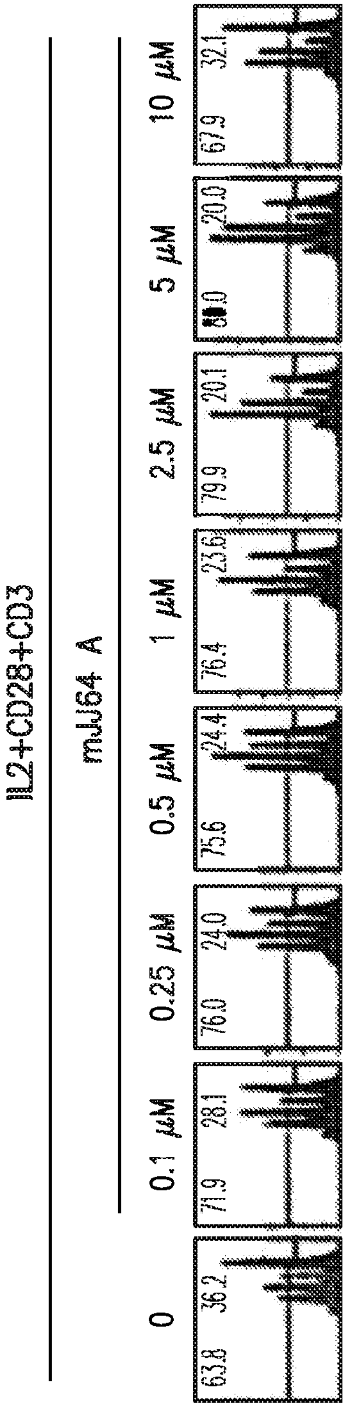
FIG. 10G is a set of histograms showing proliferation of CD4 T cells treated with various concentrations of mJJ64A.
Figure 10H:
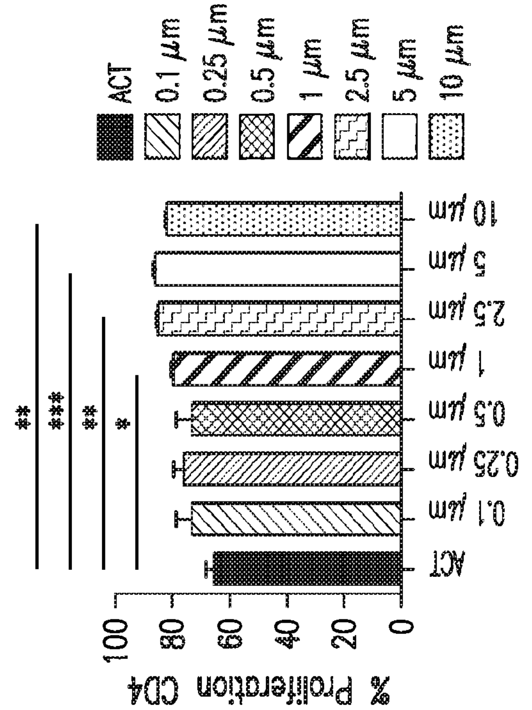
FIG. 10H is a bar graph showing percent proliferation of CD4 T cells treated with various concentrations of mJJ64A. The X-axis represents concentration of mJJ64A. The Y-axis represents percent proliferation.
Figure 10I:
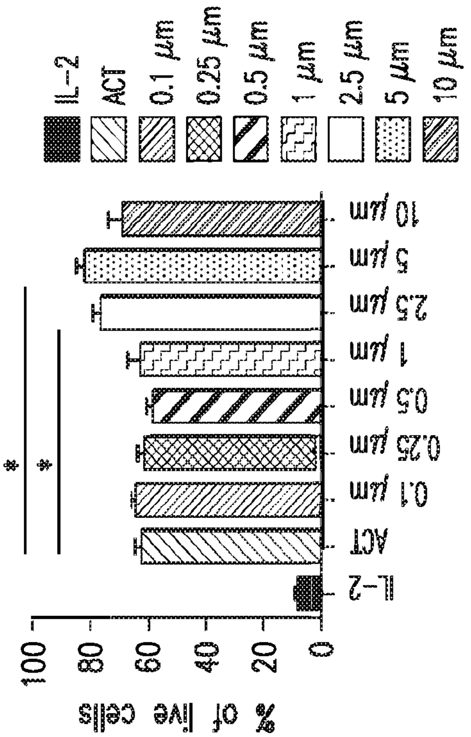
FIG. 10I is a bar graph showing the percent of live cells in CD4 T cells treated with various concentrations of mJJ64A. The X-axis represents treatment and the Y-axis represents percentage of live cells.
Figures 10J, 10K, 10L:
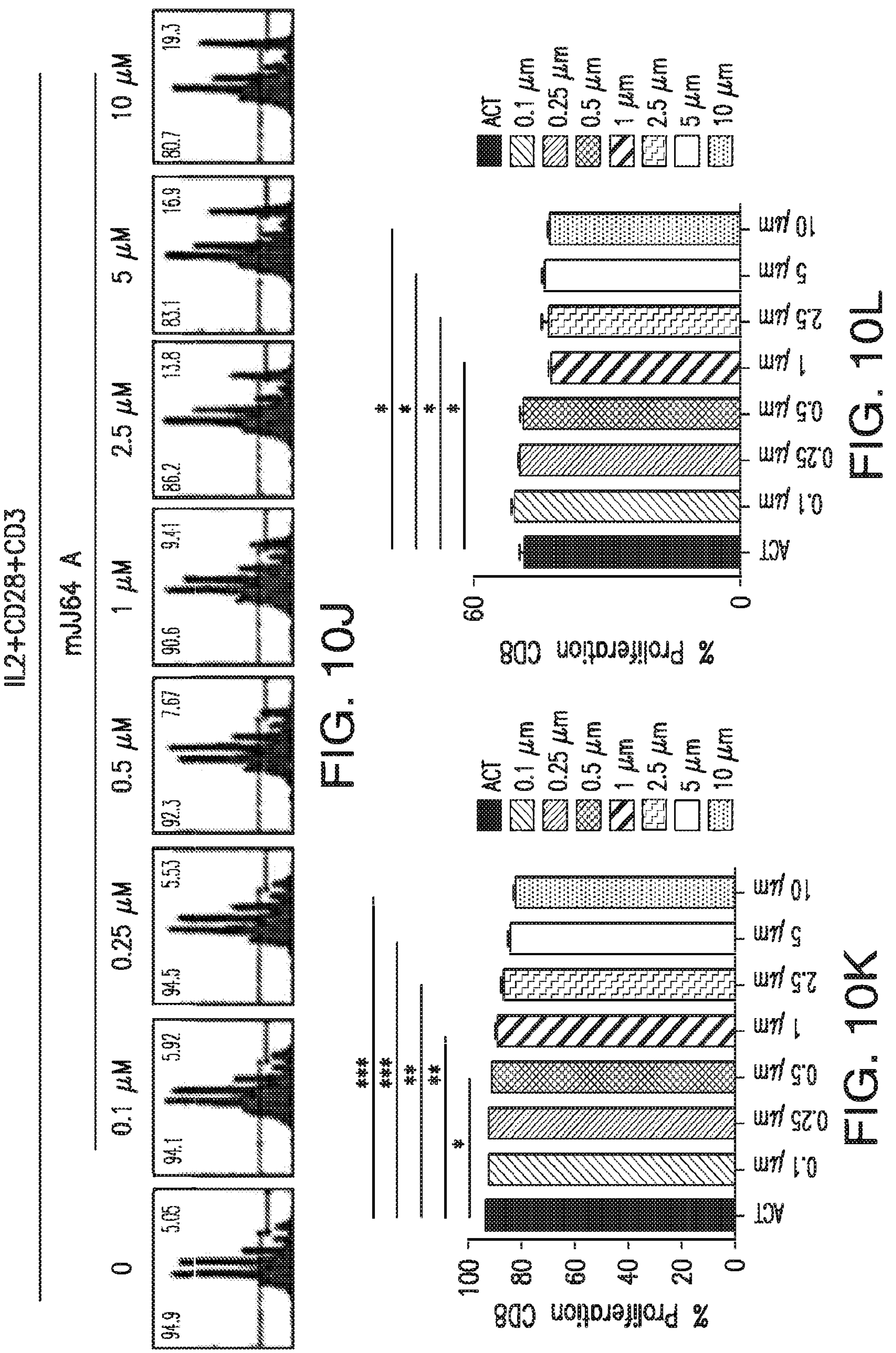
FIG. 10J is a set of histograms showing proliferation of CD8 T cells treated with various concentrations of mJJ64A.
FIG. 10K is a bar graph showing percent proliferation of CD8 T cells treated with various concentrations of mJJ64A. The X-axis represents concentration of mJJ64A. The Y-axis represents percent proliferation.
FIG. 10L is a bar graph showing the percent of live cells in CD8 T cells treated with various concentrations of mJJ64A. The X-axis represents treatment and the Y-axis represents percentage of live cells.
Figure 11A:
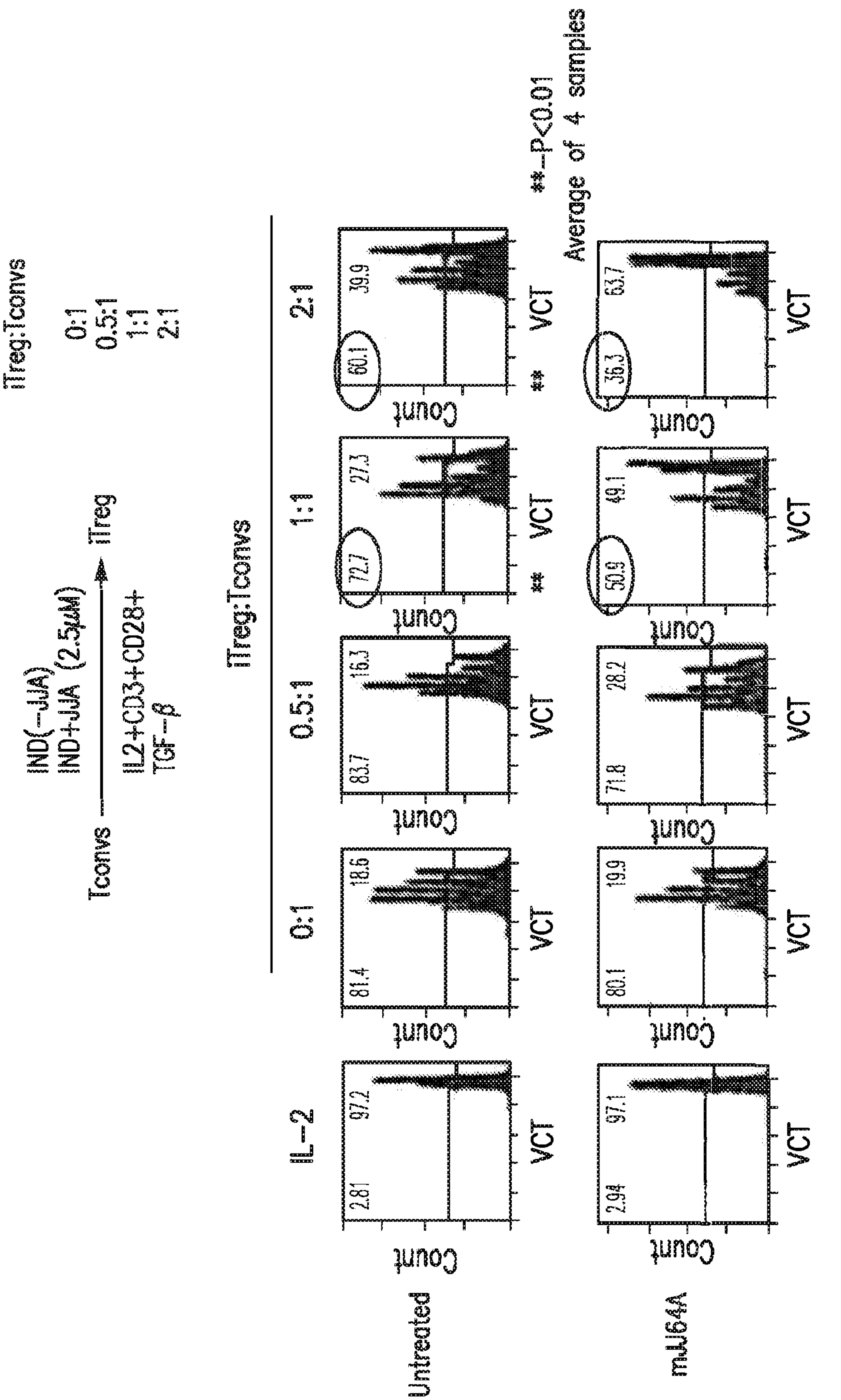
FIG. 11A is a set of histograms showing the suppressive function of mouse iTregs in untreated and mJJ64A treated iTregs. The ratio of iTreg to Tconv cells was 0:1, 0.5:1, 1:1, and 2:1.
Figure 11C:
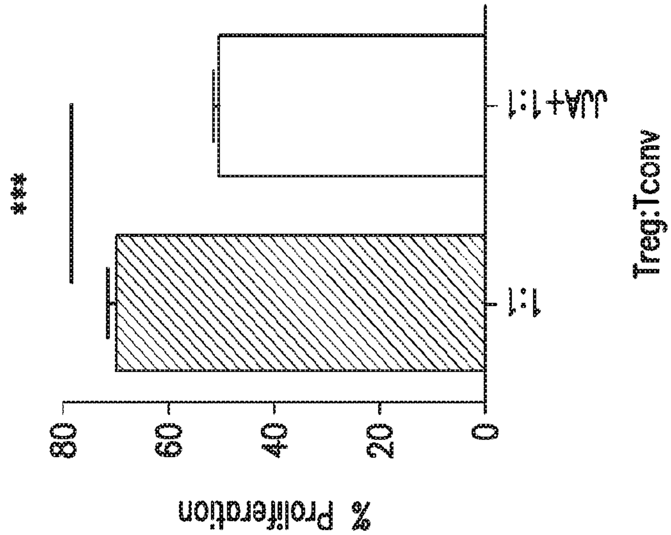
FIG. 11C is a bar graph showing the percent proliferation in untreated (black bar) and mJJ64A treated (gray bar) cells at a Treg:Tconv ratio of 1:1. The X-axis represents the experimental group and the Y axis represents percent proliferation.
Figure 11B:
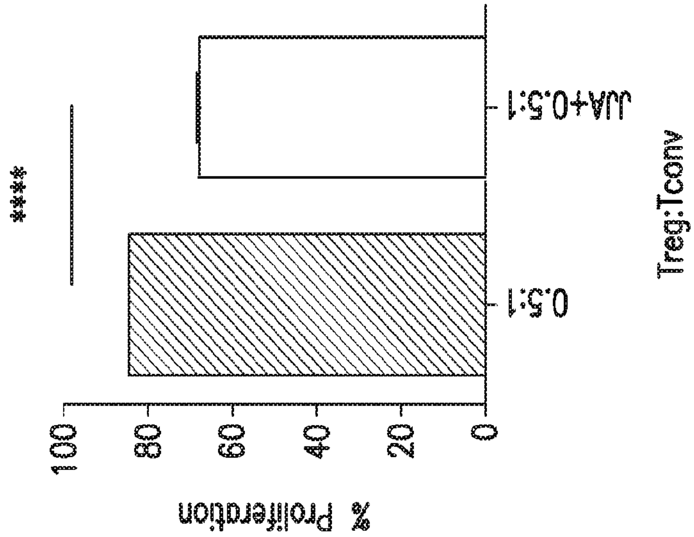
FIG. 11B is a bar graph showing the percent proliferation in untreated (black bar) and mJJ64A treated (gray bar) cells at a Treg:Tconv ratio of 0.5:1. The X-axis represents the experimental group and the Y-axis represents percent proliferation.
Figure 11D:
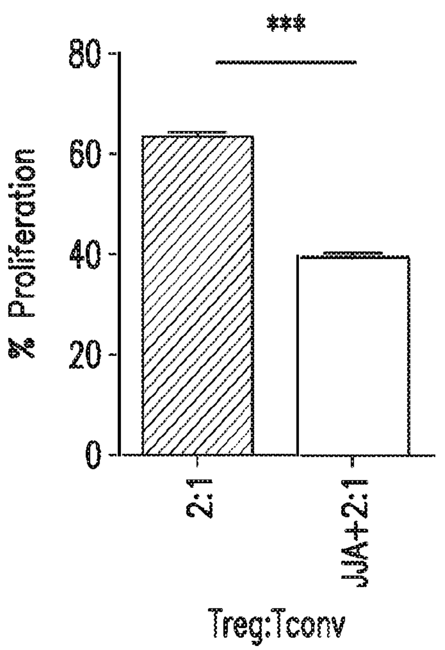
FIG. 11D is a bar graph showing the percent proliferation in untreated (black bar) and mJJ64A treated (gray bar) cells at a Treg:Tconv ratio of 2:1. The X-axis represents the experimental group and the Y-axis represents percent proliferation.
Figure 12A:
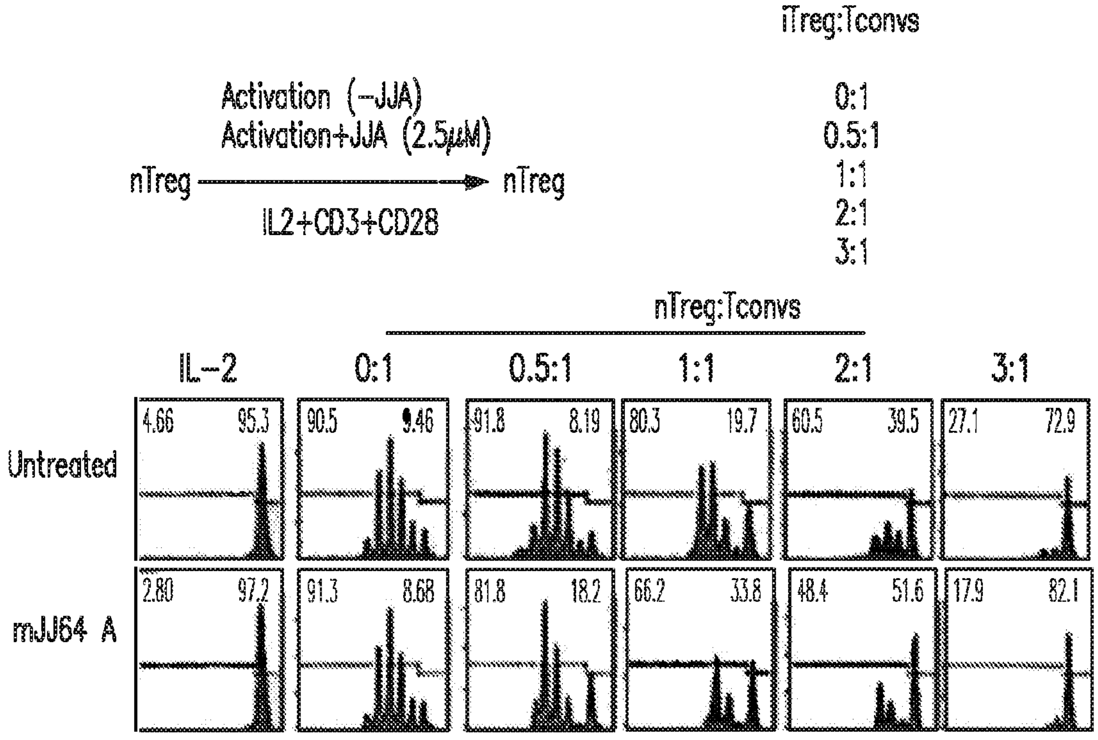
FIG. 12A is a set of histograms showing the suppressive function of untreated and mJJ64A treated nTregs. The ratio of nTreg to Tconv cells is 0:1, 0.5:1, 1:1, 2:1, and 3:1.
Figure 12B:
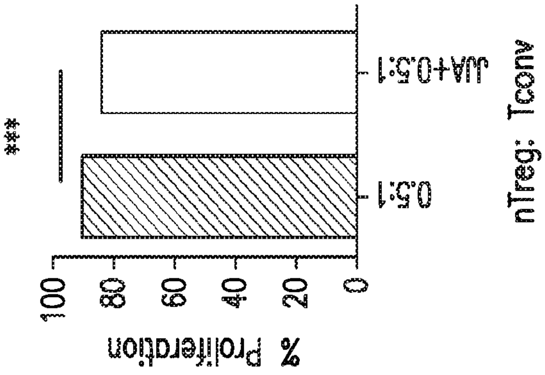
FIG. 12B is a bar graph showing the percent proliferating cells in untreated and mJJ64A treated nTregs in a mixture of nTreg and Tconv (0.5:1).
Figure 12C:
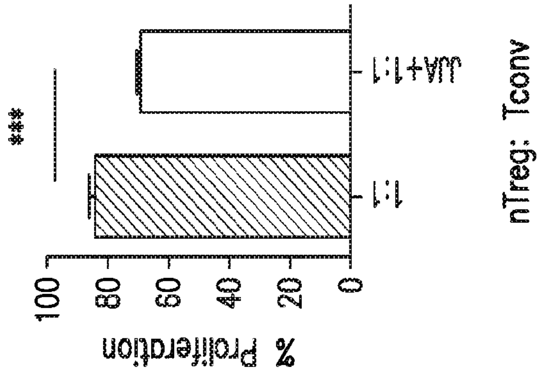
FIG. 12C is a bar graph showing the percent proliferating cells in untreated and mJJ64A treated nTregs in a mixture of nTreg and Tconv (1:1).
Figure 12D:
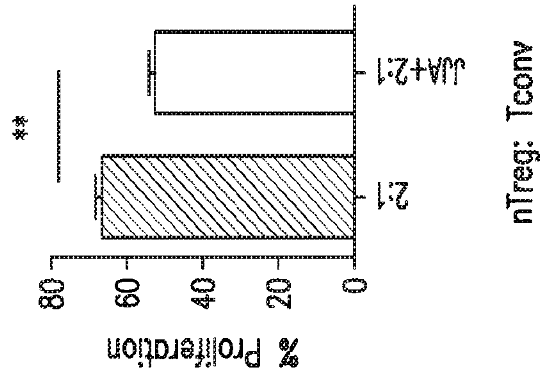
FIG. 12D is a bar graph showing the percent proliferating cells in untreated and mJJ64A treated nTregs in a mixture of nTreg and Tconv (2:1).
Figure 12E:
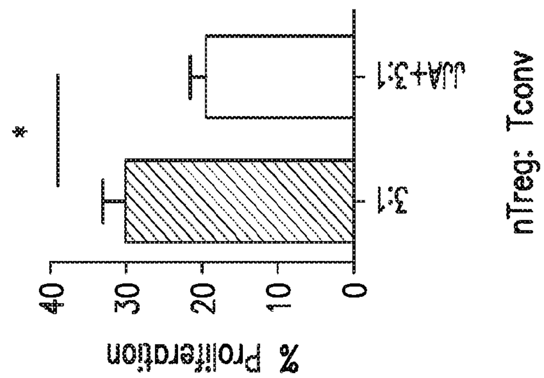
FIG. 12E is a bar graph showing the percent proliferating cells in untreated and mJJ64A treated nTregs in a mixture of nTreg and Tconv (3:1).
Figure 12F:
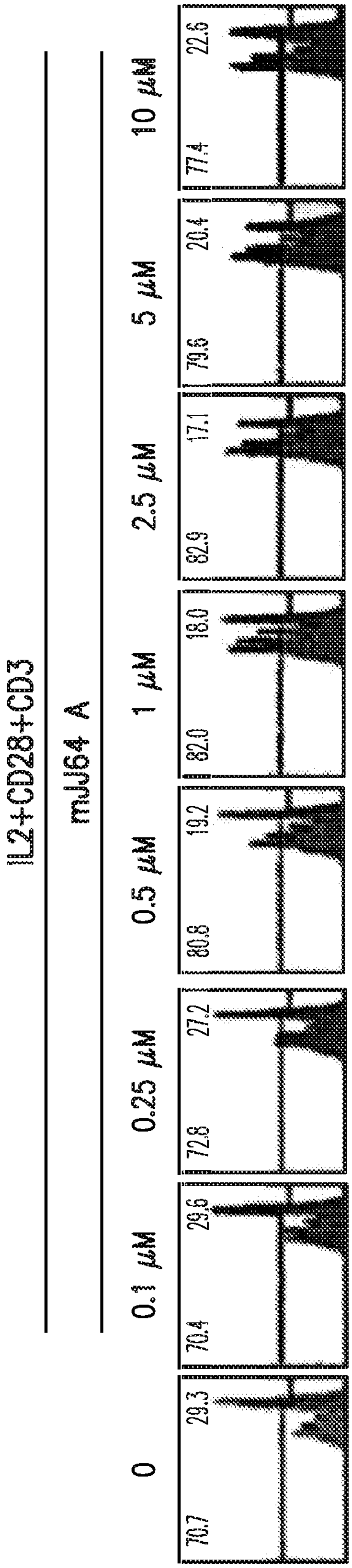
FIG. 12F is a histogram showing proliferation of nTregs treated with various concentrations of mJJ64A.
Figure 12G:
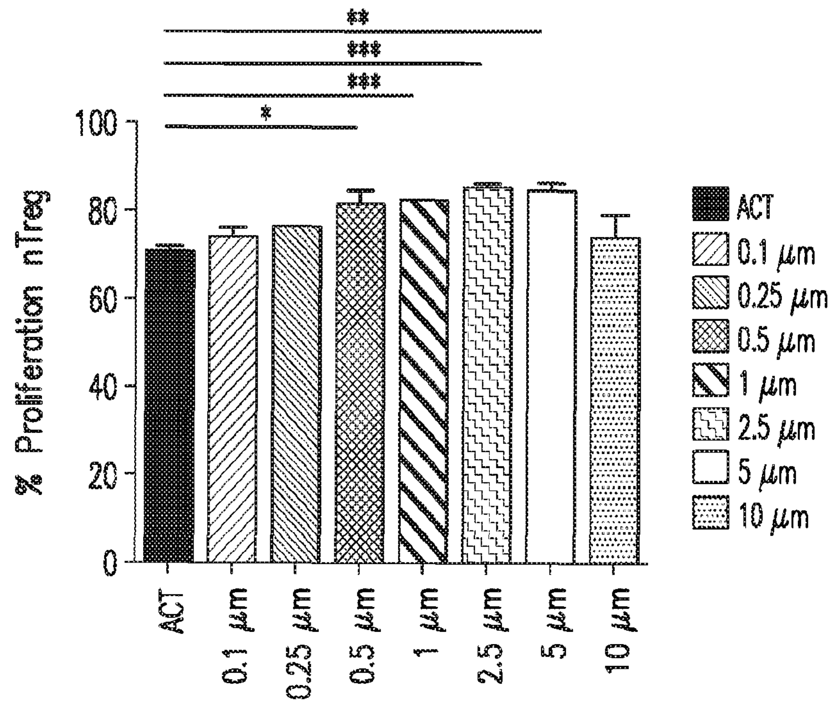
FIG. 12G is a bar graph representing the percent proliferation of nTregs treated with various concentrations of mJJ64A. The X-axis represents treatment group and the Y-axis represents percent proliferation.
Figure 12H:
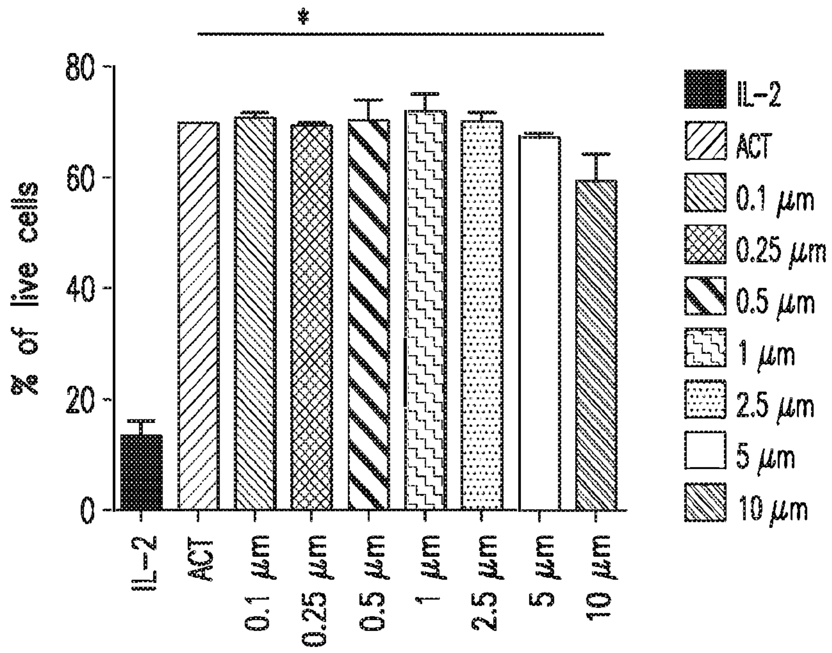
FIG. 12H is a bar graph representing percent live cells in nTregs treated with various concentrations of mJJ64A. The X-axis represents treatment group and the Y-axis represents percent proliferation.

Results mJJ64A treatment increased proliferation of iTregs (FIGS. 10A-10C) and nTregs (FIGS. 10D-10F), but not non-Treg CD4 (FIGS. 10G-10I) and CD8 (FIGS. 10J-10L) T cells.

Example 7: mJJ64A Increases Suppressive Function of Mouse iTregs and nTregs

Results

FIG. 11A-11D shows that mJJ64A treatment increased the suppressive function of mouse iTreg cells in vitro. mJJ64A treatment also increased the suppressive function of mouse nTregs cells in vitro and increased nTreg proliferation without affecting their viability (FIG. 12A-12H).

Example 8: mJJ64A Enhances IL-10 Production by nTreg

Results

Figure 13A:
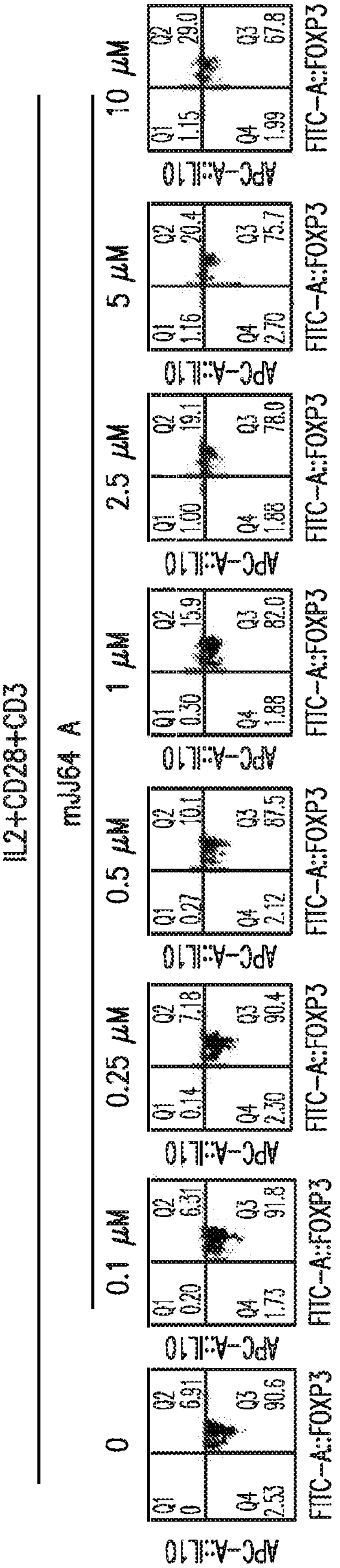
FIG. 13A is a set of histograms showing FoxP3 and IL10 expression in nTreg cells treated with various concentrations of mJJ64A.
Figure 13B:
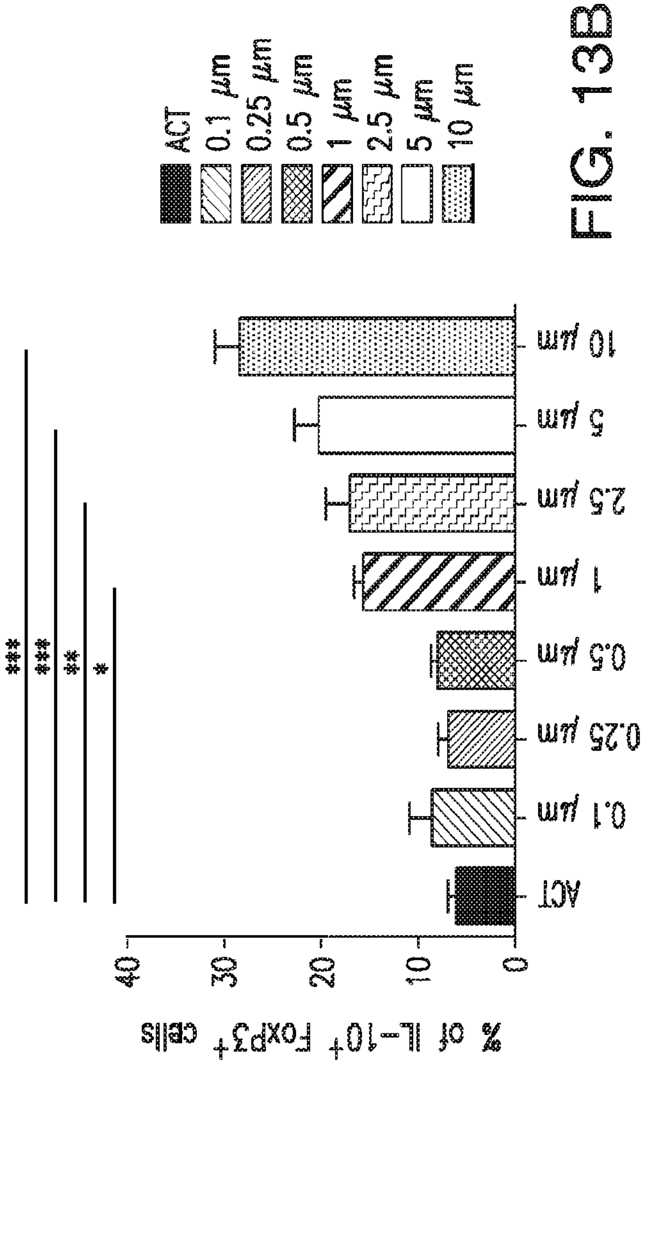
FIG. 13B is a bar graph representing the percent of $IL\text{-}10^+$ $FoxP3^+$ cells in nTregs treated with various concentrations of mJJ64A.

The data show that mJJ64A treatment increased IL-10 production by nTregs (FIG. 13A-13B).

Figure 14A:
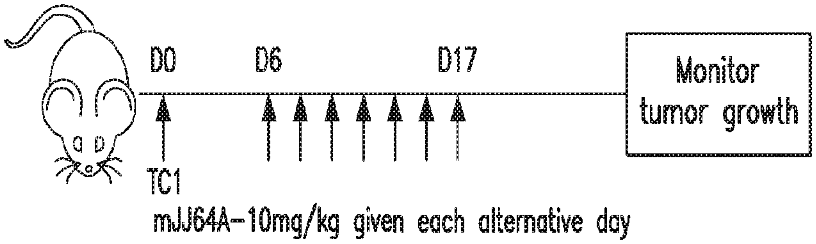
FIG. 14A is an illustration showing the experimental method and treatment schematic for TC-1 tumor experiments.
Figure 14B:
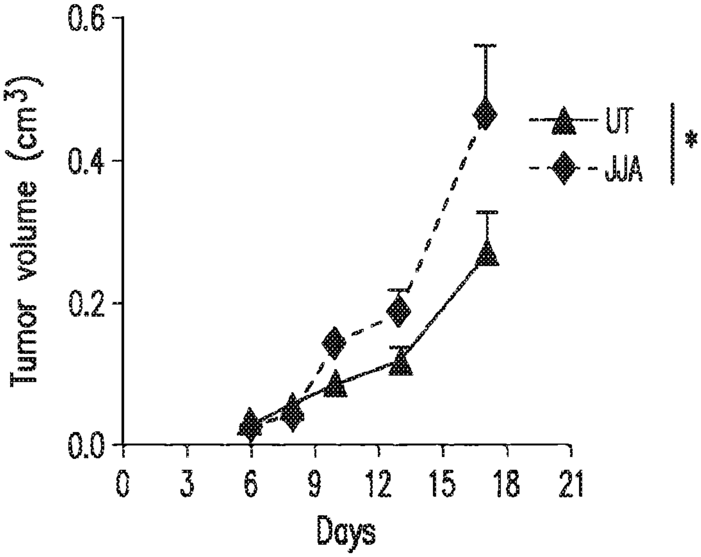
FIG. 14B is a line graph showing tumor volume ($cm^3$) over time (days) for untreated (▲) and mJJ64A treated (♦) TC1 tumor bearing mice.
Figure 15A:
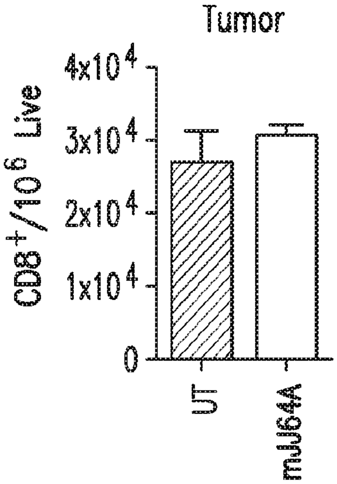
FIG. 15A is a bar graph representing the number of $CD8^+$ cells per $10^6$ live cells in tumors from untreated (black bar) and mJJ64A treated (gray bar) mice.
Figure 15B:
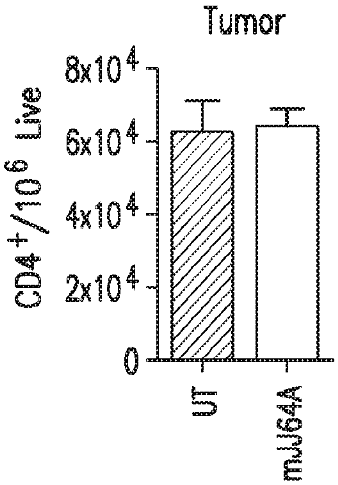
FIG. 15B is a bar graph representing the number of $CD4^+$ cells per $10^6$ live cells in tumors from untreated (black bar) and mJJ64A treated (gray bar) mice.
Figure 15C:
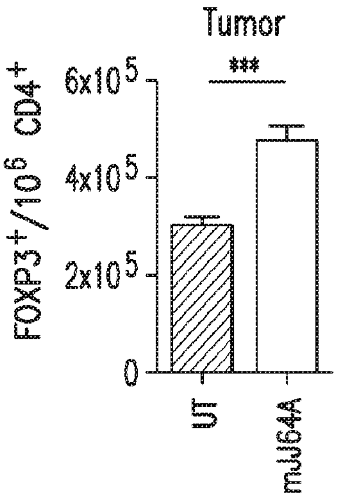
FIG. 15C is a bar graph representing the number of $FoxP3^+$ cells per $10^6$ $CD4^+$ cells in tumors from untreated (black bar) and mJJ64A treated (gray bar) mice.
Figure 15D:
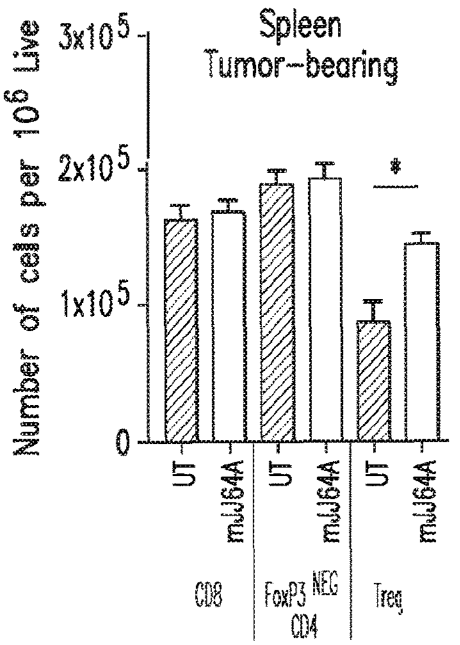
FIG. 15D is a bar graph representing the number of $CD8^+$, $FoxP3^{NEG}$ $CD4^+$, and Treg cells per $10^6$ live cells in the spleen of untreated (dark gray bar) or mJJ64A treated (light gray bar) tumor-bearing mice.
Figure 15E:
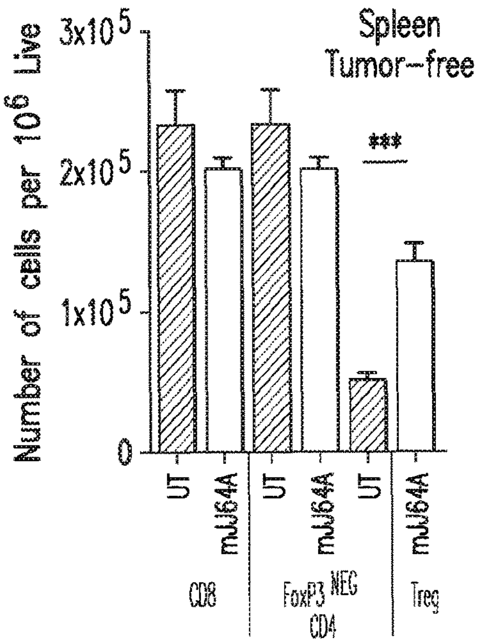
FIG. 15E is a bar graph representing the number of $CD8^+$, $FoxP3^{NEG}$ $CD4^+$, and Treg cells per $10^6$ live cells in the spleen of untreated (black bar) or mJJ64A treated (light gray bar) tumor-free mice.
Figure 16A:
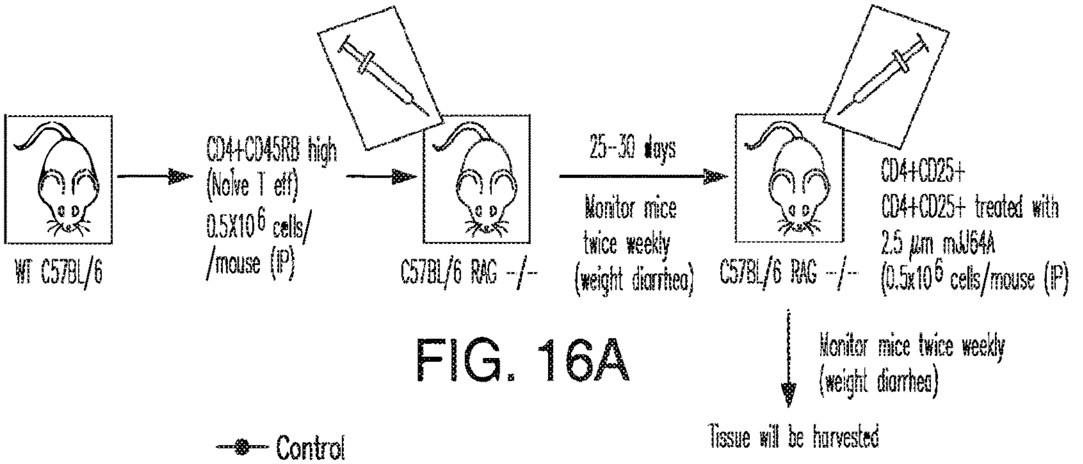
FIG. 16A is a schematic illustration of the experimental design of a colitis model.
Figure 16B:
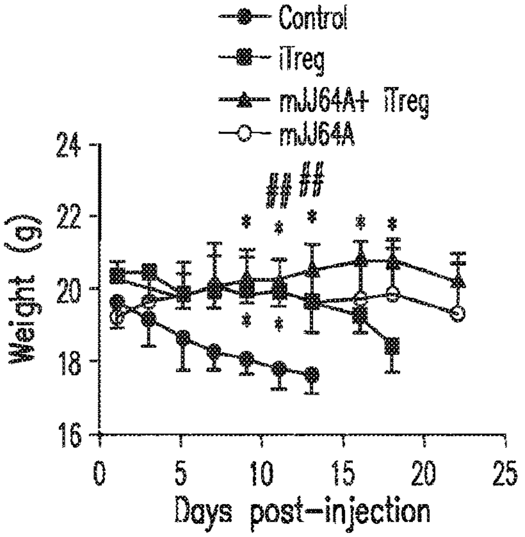
FIG. 16B is a line graph representing weight (g) over time (days post-injection) for control (●), iTreg (■), mJJ64A+iTreg (▲), and mJJ64A (○) treated colitis mice.
Figure 16C:
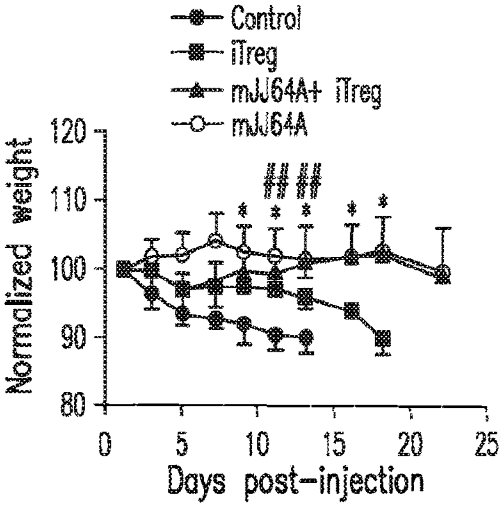
FIG. 16C is a line graph representing normalized weight over time (days post-injection) for control (●), iTreg (■), mJJ64A+iTreg (▲), and mJJ64A (○) treated colitis mice.
Figure 16D:
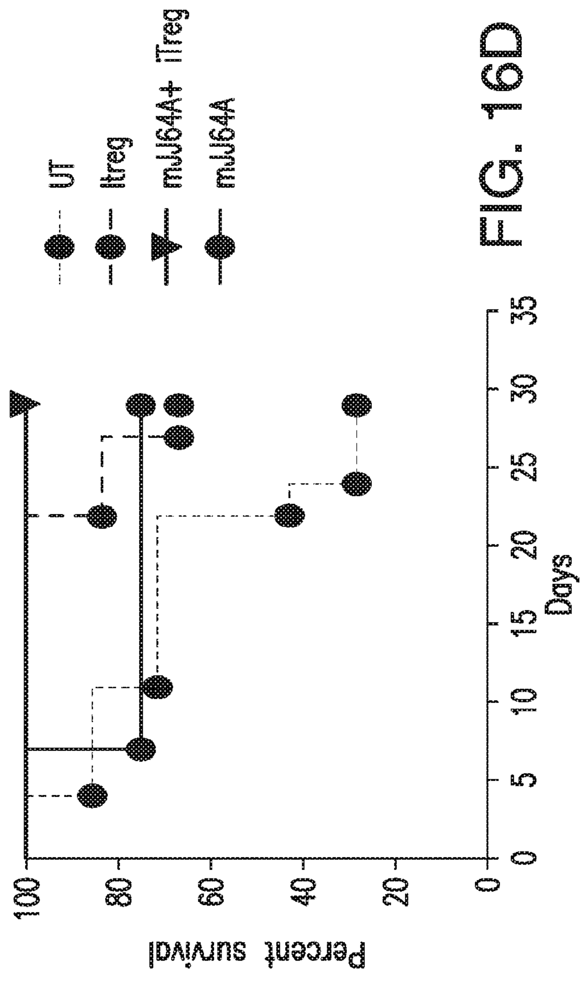
FIG. 16D is a line graph showing percent survival of untreated (●), iTreg (blue circle), mJJ64A+iTreg (▼), and mJJ64A (red circle) treated colitis mice. The X-axis represents time (days) and the Y-axis represents percent survival.
Figure 16E:
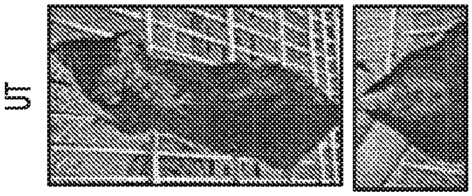
FIG. 16E-I are representative photos of untreated (FIG. 16E), iTreg treated (FIG. 16F), JJa treated iTreg (FIG. 16G), untreated (FIG. 16H), and mJJ64A treated (FIG. 16I) colitis mice. Lower image shows rectal prolapse in untreated groups.
Figure 16F:
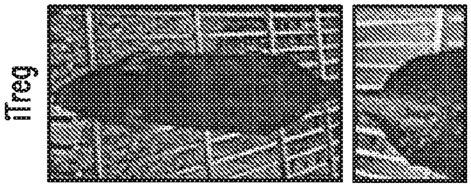
Figure 16G:
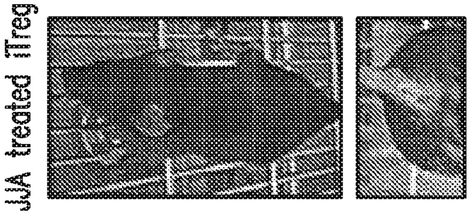
Figure 16H:
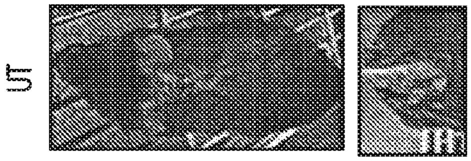
Figure 16I:
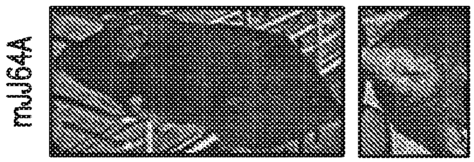
Figure 17A:
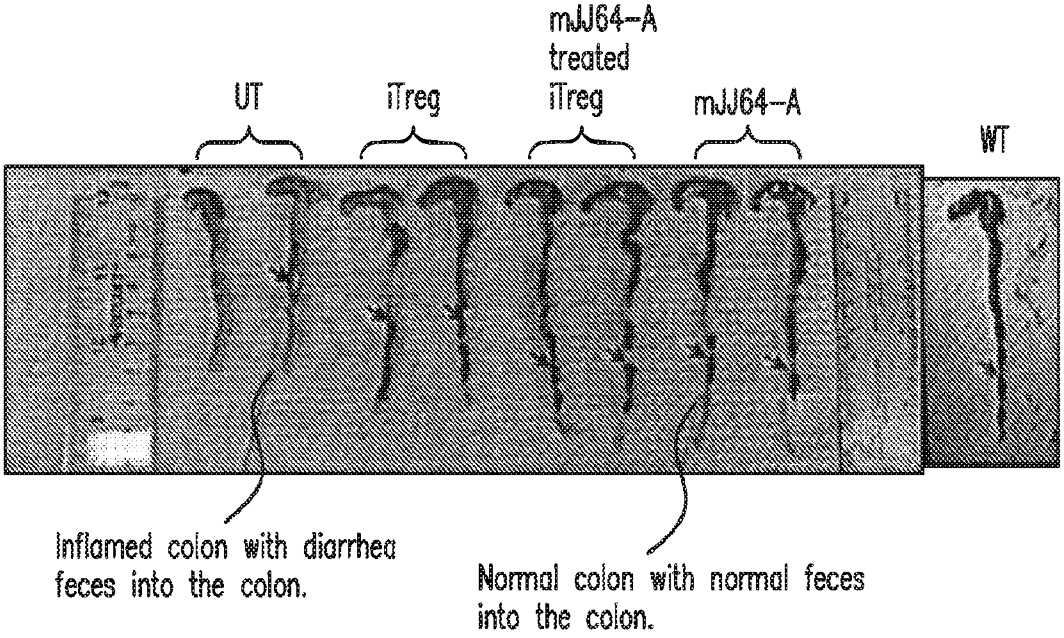
FIG. 17A is a photo showing representative colons from untreated (UT), iTreg, mJJ64A treated iTreg, mJJ64A, and wild-type (WT) mice.
Figure 17B:
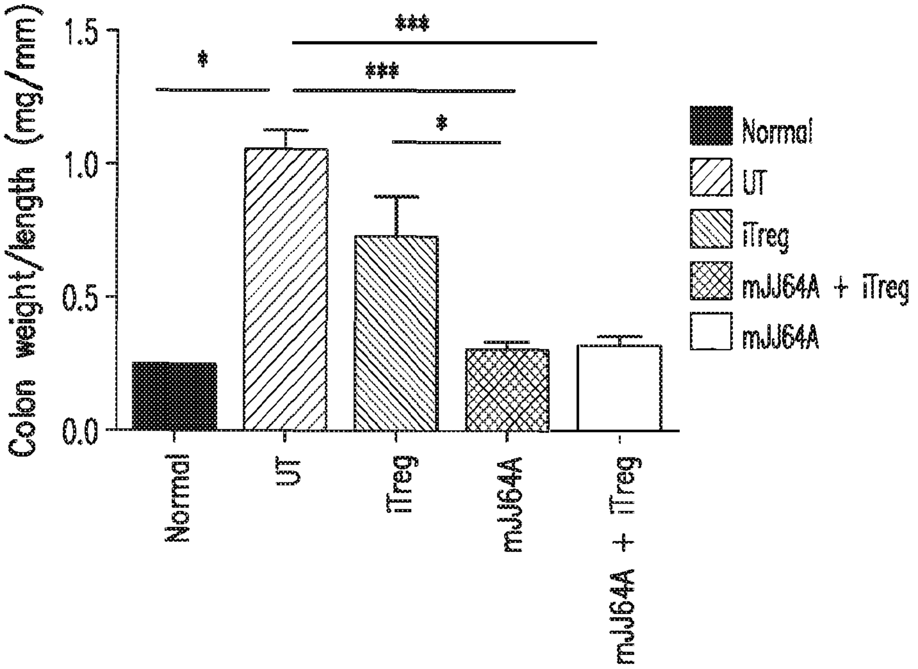
FIG. 17B is a bar graph representing length and weight of colons from normal, untreated (UT), iTreg, mJJ64A, and mJJ64A+iTreg mice. The X-axis represents the treatment group and the Y-axis represents colon weight/length (mg/mm).
Figure 17C:
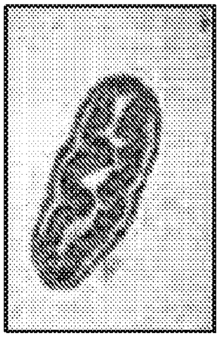
FIG. 17C-J show representative histology sections from colons from WT normal colon (FIG. 17C), $Rag^{-/-}$ colitis-untreated (FIG. 17D), WT-normal colon (FIG. 17E), $Rag^{-/-}$ colitis-untreated (FIG. 17F), $Rag^{-/-}$ colitis-iTreg treated (FIG. 17G), $Rag^{-/-}$ colitis-mJJ64A (10 mg/kg) treated (FIG. 17H), $Rag^{-/-}$ colitis-iTreg treated (FIG. 17I), and $Rag^{-/-}$ colitis-mJJ64A (10 mg/kg) treated (FIG. 17J).
Figure 17D:
Figure 17E:
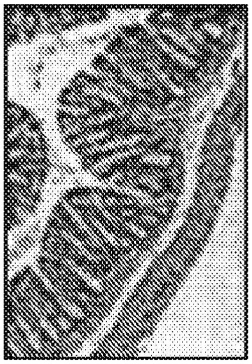
Figure 17F:
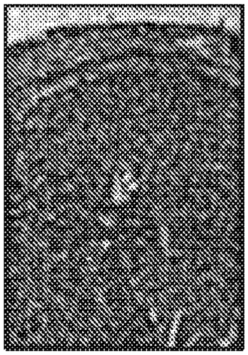
Figure 17G:
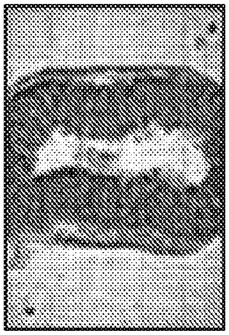
Figure 17H:
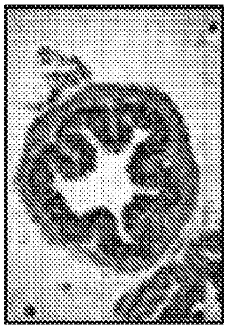
Figure 17I:
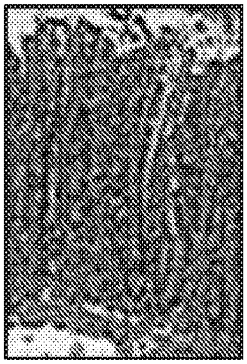
Figure 17J:
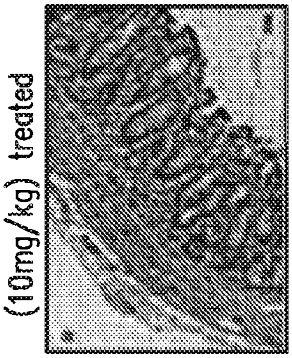
Figure 18A:
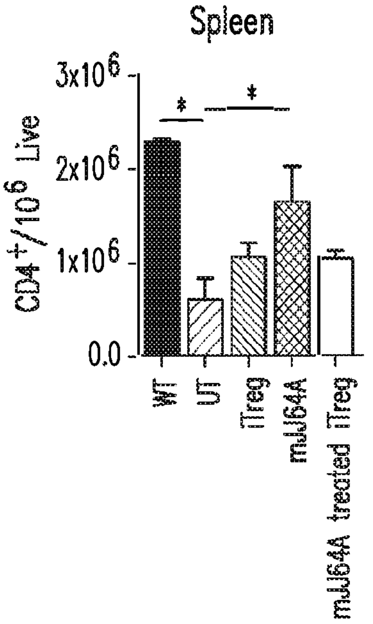
FIG. 18A is a bar graph showing the number of $CD4^+$ T cells per $10^6$ live cells in the spleen of WT, UT, iTreg, mJJ64A, and mJJ64A treated iTreg treated $Rag^{-/-}$ mice. The X-axis represents treatment group and the Y-axis represents number of $CD4^+$ cells per $10^6$ live cells.
Figure 18B:
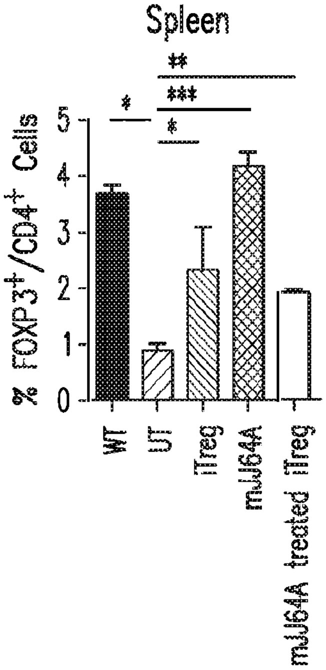
FIG. 18B is a bar graph showing the percent of $FoxP3^+$ cells per $CD4^+$ T cells in the spleen of WT, UT, iTreg, mJJ64A, and mJJ64A treated iTreg treated $Rag^{-/-}$ mice. The X-axis represents treatment group and the Y-axis represents number of $FoxP3^+$ cells per $CD4^+$ cells.
Figure 18C:
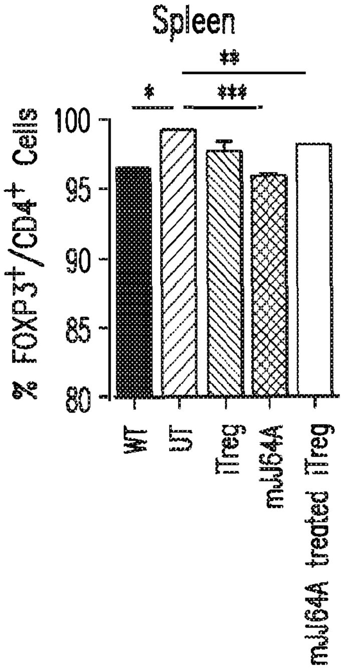
FIG. 18C is a bar graph showing the percent of $FoxP3^-$ cells per $CD4^+$ T cells in the spleen of WT, UT, iTreg, mJJ64A, and mJJ64A treated iTreg treated $Rag^{-/-}$ mice. The X-axis represents treatment group and the Y-axis represents number of $FoxP3^-$ cells per $CD4^+$ cells.
Figure 18D:
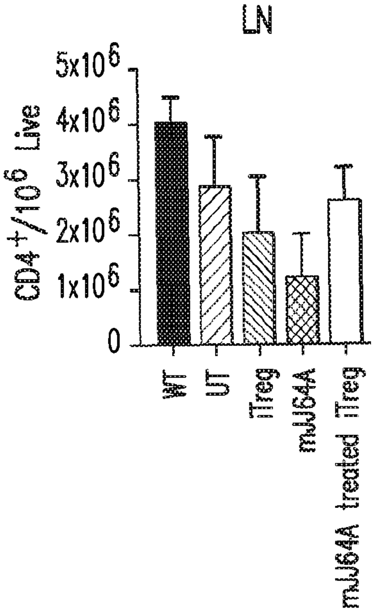
FIG. 18D is a bar graph showing the number of $CD4^+$ T cells per $10^6$ live cells in the lymph node of WT, UT, iTreg, mJJ64A, and mJJ64A treated iTreg treated $Rag^{-/-}$ mice. The X-axis represents treatment group and the Y-axis represents number of $CD4^+$ cells per $10^6$ live cells.
Figure 18E:
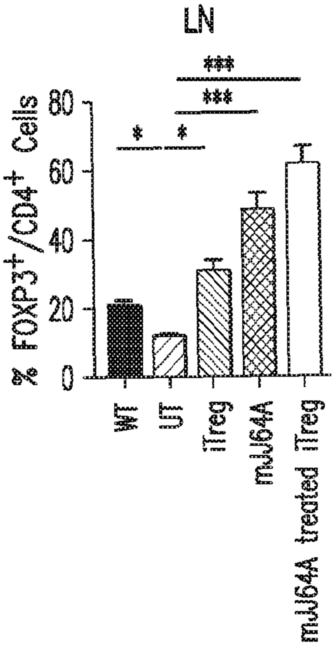
FIG. 18E is a bar graph showing the percent of $FoxP3^+$ cells per $CD4^+$ T cells in the lymph node of WT, UT, iTreg, mJJ64A, and mJJ64A treated iTreg treated $Rag^{-/-}$ mice. The X-axis represents treatment group and the Y-axis represents number of $FoxP3^+$ cells per $CD4^+$ cells.
Figure 18F:
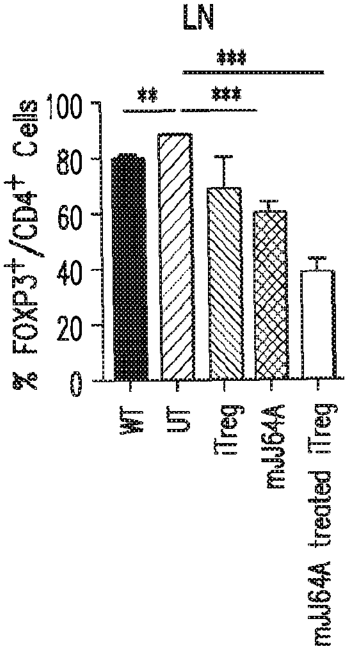
FIG. 18F is a bar graph showing the percent of $FoxP3^-$ cells per $CD4^+$ T cells in the lymph node of WT, UT, iTreg, mJJ64A, and mJJ64A treated iTreg treated $Rag^{-/-}$ mice. The X-axis represents treatment group and the Y-axis represents number of $FoxP3^-$ cells per $CD4^+$ cells.
Figure 19E:
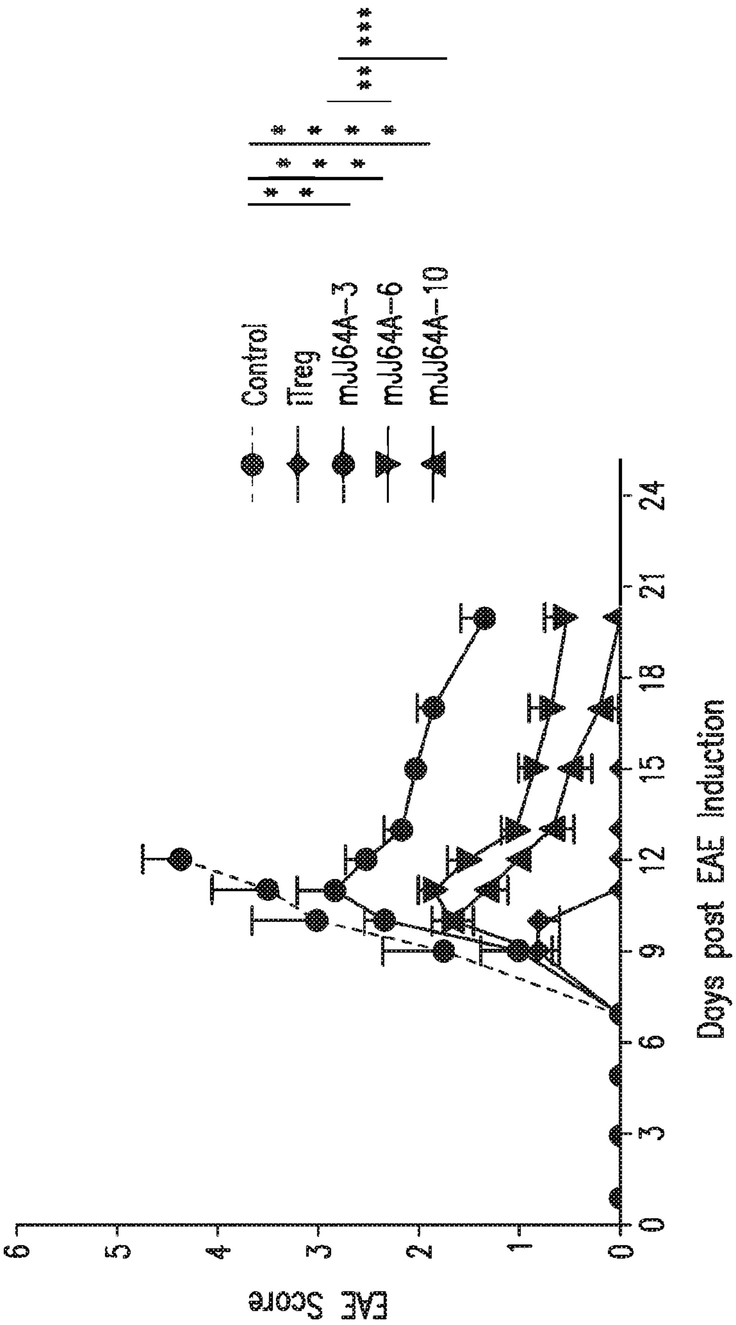
FIG. 19E is a line graph representing EAE score over time (days post EAE induction) for control (●), iTreg (◆), mJJ64A-3 (blue circle), mJJ64A-6 (▼), and mJJ64A-10 (▲) treated EAE mice. The X-axis represents time (days post EAE induction) and the Y-axis represents EAE score.
Figure 19F:
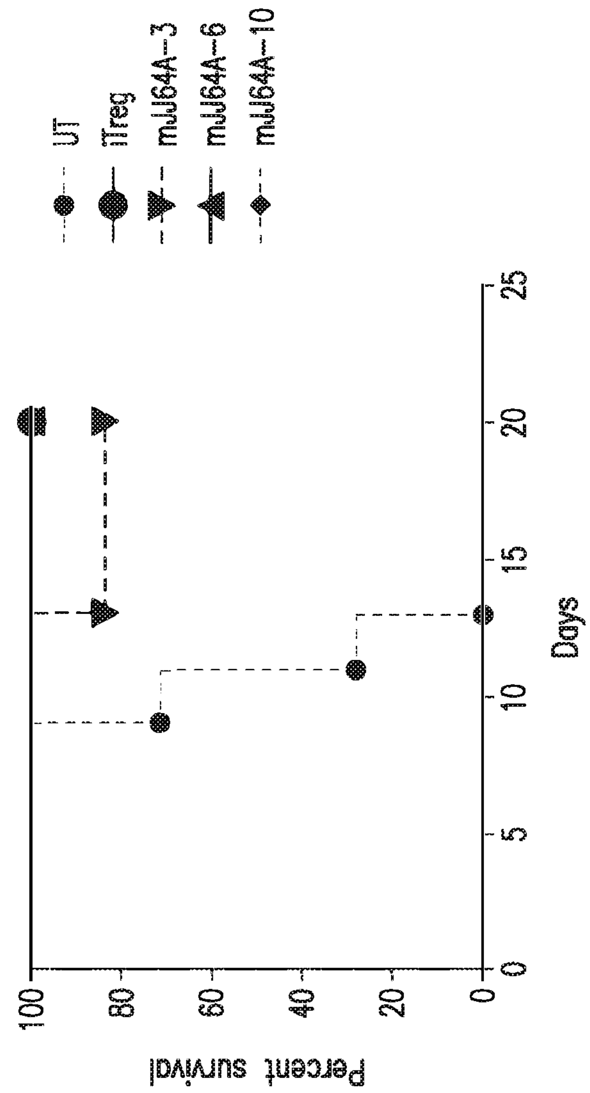
FIG. 19F is a line graph representing percent survival over time (days) for untreated (●), iTreg (blue circle), mJJ64A-3 (▼), mJJ64A-6 (▲), and mJJ64A-10 (◆) treated EAE mice. The X-axis represents time (days) and the Y-axis represents percent survival.
Figure 20A:
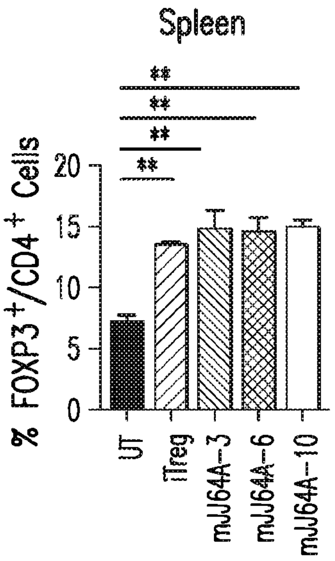
FIG. 20A-C are bar graphs showing the percent of $FoxP3^+$ cells per $CD4^+$ T cells in the spleen (FIG. 20A), blood (FIG. 20B), and brain (FIG. 20C) of UT, iTreg, mJJ64A-3, mJJ64A-6 and mJJ64A-10 treated EAE mice. The X-axis represents treatment group and the Y-axis represents number of $FoxP3^+$ cells per $CD4^+$ cells.
Figure 20B:
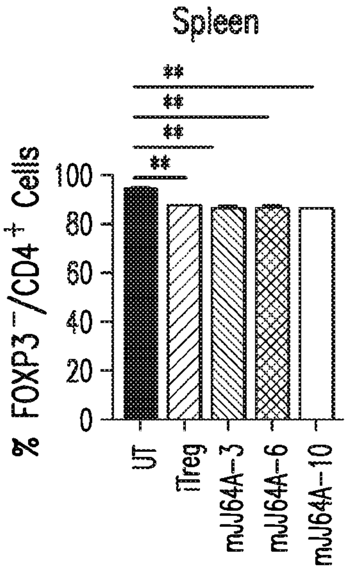
Figure 20C:
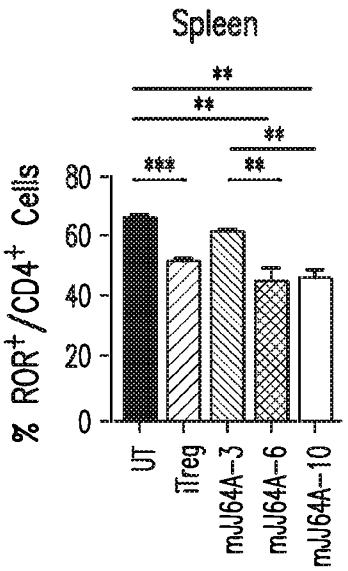
Figure 20D:
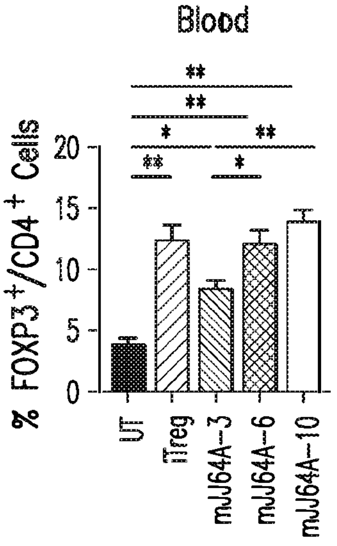
FIG. 20D-F are bar graphs showing the percent of $FoxP3^-$ cells per $CD4^+$ T cells in the spleen (FIG. 20D), blood (FIG. 20E), and brain (FIG. 20F) of UT, iTreg, mJJ64A-3, mJJ64A-6 and mJJ64A-10 treated EAE mice. The X-axis represents treatment group and the Y-axis represents number of $FoxP3^-$ cells per $CD4^+$ cells.
Figure 20E:
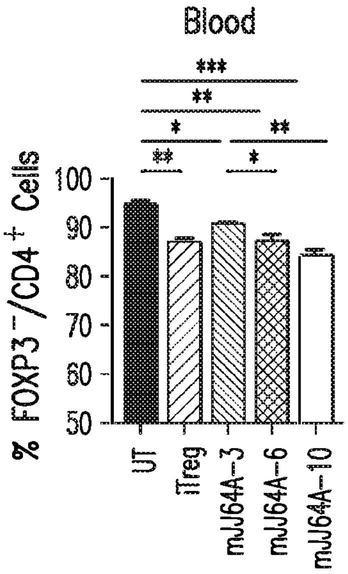
Figure 20F:
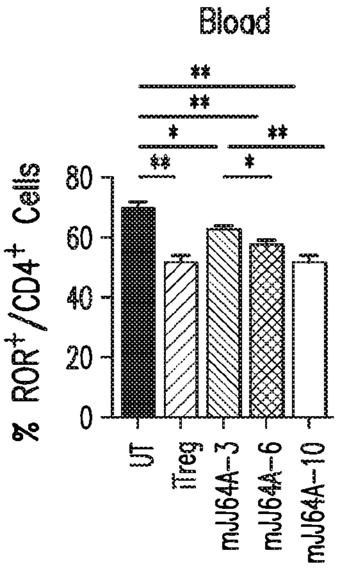
Figure 20G:
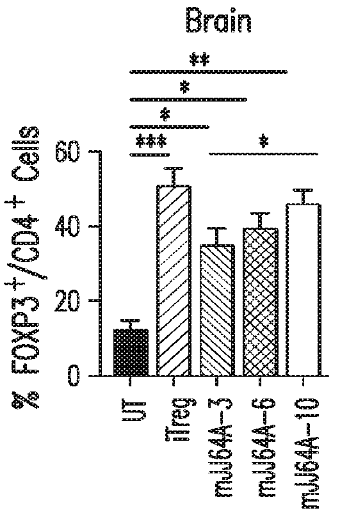
FIG. 20G-I are bar graph showing the percent of $ROR^+$ cells per $CD4^+$ T cells in the spleen (FIG. 20G), blood (FIG. 20H), and brain (FIG. 20I) of UT, iTreg, mJJ64A-3, mJJ64A-6 and mJJ64A-10 treated EAE mice. The X-axis represents treatment group and the Y-axis represents number of $ROR^+$ cells per $CD4^+$ cells.
Figure 20H:
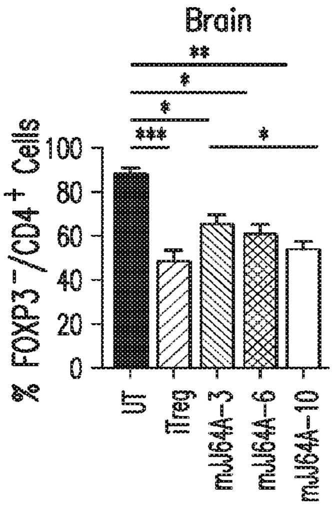
Figure 20I:
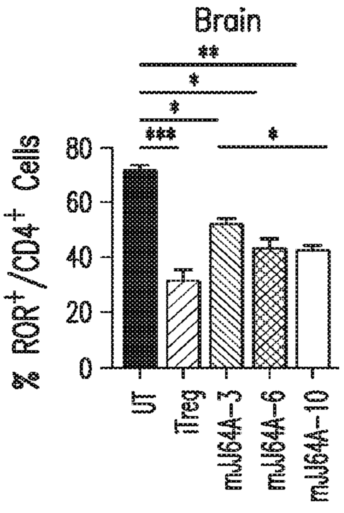

Example 9: mJJ64A Increases TC-1 Tumor Growth and Significantly Increases Tregs in Tumors and Spleens of Treated Mice Results The data show that TC-1 tumor-bearing mice treated with mJJ64A showed significantly increased tumor growth compared to untreated controls (FIGS. 14A and 14B). mJJ64A also increased the number of Tregs in the tumors and spleens of treated mice compared to untreated controls (FIGS. 15D and 15E). Tumor-infiltration of $CD8^+$ and $FoxP3^{NEG}$ CD4 T cells is not affected by mJJ64A treatment (FIGS. 15A-15C).

Example 10: mJJ64A Protects Against Experimental Colitis

Results

The data show that mJJ64A treatment protected against experimental colitis (FIGS. 16A-16I and FIGS. 17A-17J). In addition, treating mice with iclTregs that were treated with mJJ64A ex vivo also resulted in protection against experimental colitis (FIGS. 16A-16I and FIGS. 17A-17J).

Example 11: mJJ64A Enhances The Percent of Tregs in $Rag^{-/-}$ Mice

Results

The data show that treating Rag–/– mice with mJJ64A increased the percent of Tregs in the spleen and mesenteric lymph nodes when compared to untreated Rag–/– mice (FIG. 18A-F).

Example 12: Efficacy of mJJ64A in Mouse EAE-Model

Results mJJ64A reduced disease progression and increased survival rate in a mouse experimental autoimmune encephalomyelitis (EAE) model (FIG. 19A-19F). In addition, mJJ64A-induced iTregs also reduced disease progression and increased survival rate in the EAE model, compared to untreated controls (FIG. 19).

Figures 21A, 21B:
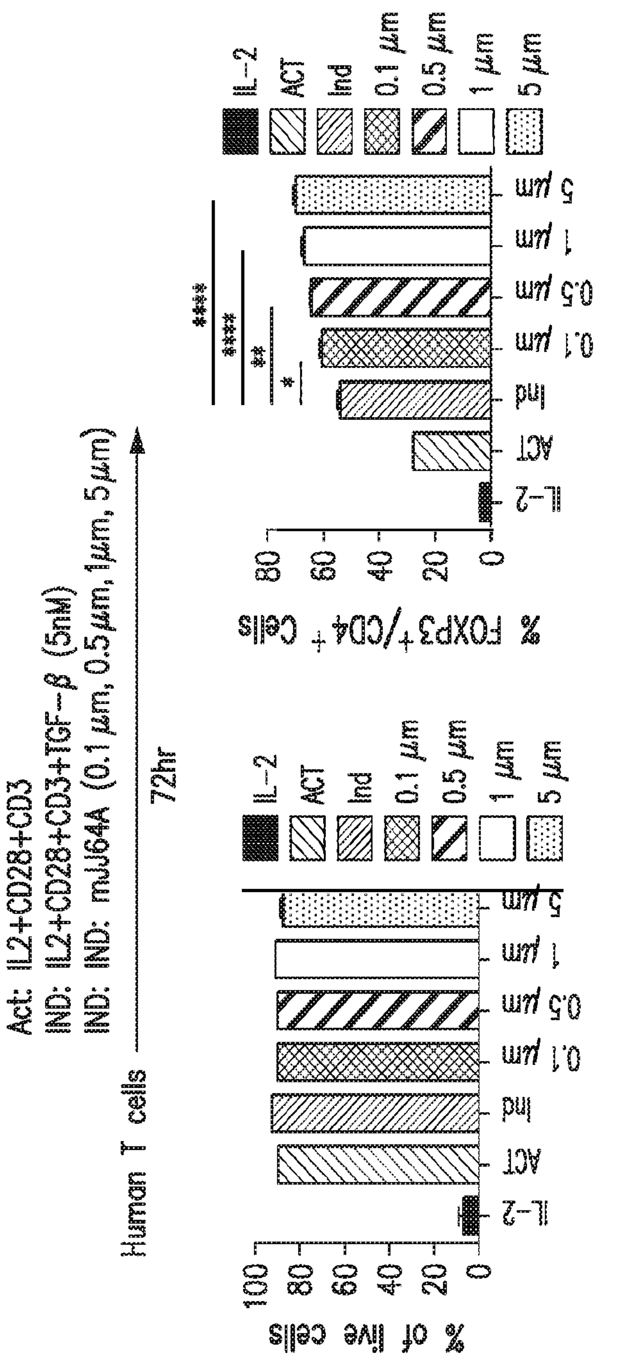
FIG. 21A is a bar graph showing the percent of live human iTregs in cells treated with various concentrations of mJJ64A. The X-axis represents treatment group and the Y-axis represents percent of live cells.
FIG. 21B is a bar graph showing the percent of $FoxP3^+CD4^+$ cells in human iTregs treated with various concentrations of mJJ64A. The X-axis represents treatment group and the Y-axis represents percent of $FoxP3^+CD4^+$ cells.

Example 13: mJJ64A Increases Induction of iTregs Without Affecting Cell Viability Results The data show that mJJ64A induced human iTregs (FIG. 21B) but did not affect cell viability (FIG. 21A).

We claim:

1. A compound according to Formula I:

Formula I

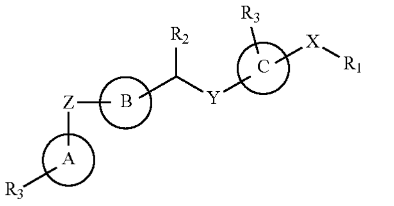

or a pharmaceutically acceptable enantiomer, or salt thereof, wherein:

rings A and C are independently phenyl, pyridine, pyrimidine, pyridazine, pyrazine, triazine, quinoline, quinazoline, isoquinoline, naphthalene, naphthyridine, indole, isoindole, cinnoline, phthalazine, quinoxaline, pteridine, purine, or benzimidazole;

ring B is a six-membered aryl, an N-containing heteroaryl mono- or bicyclic ring system containing one or more N atoms, or an aryl bicyclic ring system;

$R_1$ is selected from the group consisting of —$(C_1$-$C_{30})$-alkyl, —$(C_3$-$C_{12})$-cycloalkyl, —$(C_3$-$C_{12})$-heterocycloalkyl, —$(C_6$-$C_{20})$-aryl, or —$(C_3$-$C_{20})$-heteroaryl groups optionally substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—$[(C_1$-$C_{12})$-alkyl$]_2$, —COOH, —OH, —SH, —$SO_3H$, —CN, —$NH_2$, or a halogen;

X, Y, and Z are independently —O, —NH, —S, or —N—$(C_1$-$C_{30})$-alkyl;

$R_2$ is =O, —OH, —$SO_2$, —SO, or —$SOCH_3$;

$R_3$ on ring A is —$(C_1$-$C_{30})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl, —O—$(C_1$-$C_{12})$-alkyl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—$[(C_1$-$C_{12})$-alkyl$]_2$, —$(C_6$-$C_{20})$-aryl-$(C_1$-$C_{12})$-alkyl, —$(C_3$-$C_{20})$-heteroaryl-$(C_1$-$C_{12})$-alkyl, —COOH, —OH, —SH, —$SO_3H$, —CN, —$NH_2$, or a halogen; and $R_3$ on ring C is hydrogen, —$(C_1$-$C_{30})$-alkyl, —$(C_3$-$C_{12})$-cycloalkyl, —$(C_3$-$C_{12})$-heterocycloalkyl, —N—$[(C_1$-$C_{12})$-alkyl$]_2$, —COOH, —OH, —SH, —$SO_3H$, —CN, —$NH_2$, or a halogen, with the proviso that:

(i) when $R_1$ is unsubstituted pyridine or N-substituted pyridine by —$(C_1)$-alkyl, X, Y, Z are —NH, $R_2$ is =O, A is quinoline or pyridine, B is phenyl or pyridine, C is phenyl, $R_3$ on ring C is hydrogen, then $R_3$ on ring A is not —COO—$(C_1)$-alky, not —CO—$(C_1)$-alkyl, not —N—$[(C_1)$-alkyl$]_2$, not —COOH, not —CN, and not —F;

(ii) when the compound has the structure of Formula III,

Formula III

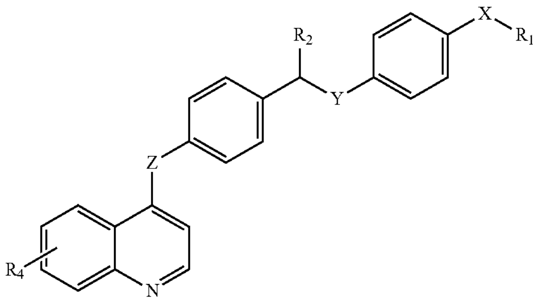

$R_1$ is unsubstituted pyridine, N-substituted pyridine by —$(C_1$-$C_3)$-alkyl, or pyrimidine substituted by —$(C_1)$-alkyl and —$NH_2$, X, Y, Z are —NH, $R_2$ is =O, then $R_4$ is not halogen, not —$(C_1)$-alkyl, not —O—$(C_1)$-alkyl, not —$NH_2$, and not —N—$[(C_1)\text{-alkyl}]_2$ (iii) when $R_1$ is unsubstituted pyridine, unsubstituted quinoline, quinoline substituted by —$NH_2$, —$NO_2$, or —N—$[(C_1)\text{-alkyl}]_2$, or pyrimidine substituted by —$(C_1)$-alkyl and —$NH_2$, X, Y, Z are —NH, $R_2$ is =O, A is pyridine, naphthalene, or pyrimidine, B is phenyl, C is phenyl, $R_3$ on ring C is hydrogen, then $R_3$ on ring A is not —$(C_1\text{-}C_2)$-alkyl and not —$NH_2$;

(iv) when $R_1$ is acridine, X, Y, Z are —NH, $R_2$ is =O, A is pyridine or pyrimidine substituted by —$(C_1)$-alkyl and —$NH_2$, B is phenyl, C is phenyl, $R_3$ on ring C is hydrogen, then $R_3$ on ring A is not —$(C_1)$-alkyl; and (v) when A is pyridine or quinazoline, B is phenyl, C is phenyl, X is —O, Z is —O or —NH, Y is —NH, $R_2$ is =O, $R_3$ on ring A is pyrimidine, phenyl, or —CONH—$(C_1)$-alkyl, $R_3$ on ring C is halogen or —$(C_1)$-alkyl, then $R_1$ is not —$(C_1)$-alkyl, not —$(C_2\text{-}C_3)$-alkyl substituted by —N—$[(C_1)\text{-alkyl}]_2$ or —$(C_4)$-heterocycloalkyl.

2. The compound according to claim 1, wherein ring B is a six-membered aryl.

3. The compound according to claim 2, wherein ring B is phenyl.

4. The compound according to claim 1, wherein ring B is an N-containing heteroaryl mono- or bicyclic ring system containing one or more N atoms.

5. The compound according to claim 4, wherein ring B is pyridine, pyrimidine, pyridazine, pyrazine, triazine, quinoline, quinazoline, isoquinoline, naphthyridine, indole, isoindole, cinnoline, phthalazine, quinoxaline, pteridine, purine, or benzimidazole.

6. The compound according to claim 1, wherein ring B is an aryl bicyclic ring system.

7. The compound according to claim 6, wherein ring B is naphthalene.

8. The compound according to claim 1, wherein ring A is pyridine.

9. The compound according to claim 1, wherein ring A is quinoline.

10. The compound according to claim 1, wherein $R_3$ on ring A is-CN, —N—$[(C_1\text{-}C_{12})\text{-alkyl}]_2$, or —$(C_3\text{-}C_{12})$-heterocycloalkyl.

11. The compound according to claim 1, wherein $R_3$ on ring C is hydrogen, —$(C_1\text{-}C_{30})$-alkyl, or halogen.

12. The compound according to claim 1, wherein $R_1$ is phenyl, pyridine, pyrimidine, pyridazine, —$(C_3\text{-}C_{12})$-cycloalkyl, or —$(C_3\text{-}C_{12})$-heterocycloalkyl, optionally substituted by one or more —$(C_1\text{-}C_{12})$-alkyl, —$NH_2$, —CN, halogen, —$(C_3\text{-}C_{20})$-cycloalkyl, or —$(C_3\text{-}C_{20})$-heteroaryl.

13. The compound according to claim 1, wherein X, Y, and Z are independently —O, —NH—, or —N—$(C_1\text{-}C_{30})$-alkyl.

14. A pharmaceutical composition comprising a compound according to Formula I, or an enantiomer, or a pharmaceutically acceptable salt thereof; and an excipient, Formula I

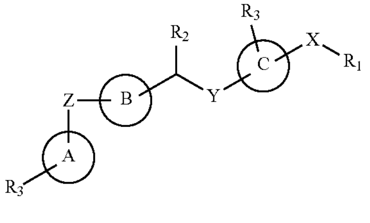

or a pharmaceutically acceptable enantiomer, or salt thereof, wherein:

rings A and C are independently phenyl, pyridine, pyrimidine, pyridazine, pyrazine, triazine, quinoline, quinazoline, isoquinoline, naphthalene, naphthyridine, indole, isoindole, cinnoline, phthalazine, quinoxaline, pteridine, purine, or benzimidazole;

ring B is six-membered aryl, N-containing heteroaryl mono- or bicyclic ring system containing one or more N atoms, or aryl bicyclic ring system;

$R_1$ is selected from the group consisting of-$(C_1\text{-}C_{30})$-alkyl, —$(C_3\text{-}C_{12})$-cycloalkyl, —$(C_3\text{-}C_{12})$-heterocycloalkyl, —$(C_6\text{-}C_{20})$-aryl, or —$(C_3\text{-}C_{20})$-heteroaryl groups optionally substituted by one or more substituents selected from —$(C_1\text{-}C_{12})$-alkyl, —$(C_3\text{-}C_{12})$-cycloalkyl, —$(C_3\text{-}C_{12})$-heterocycloalkyl, —O—$(C_1\text{-}C_{12})$-alkyl, —O—$(C_3\text{-}C_{12})$-cycloalkyl, —S—$(C_1\text{-}C_{12})$-alkyl, —S—$(C_3\text{-}C_{12})$-cycloalkyl, —COO—$(C_1\text{-}C_{12})$-alkyl, —COO—$(C_3\text{-}C_{12})$-cycloalkyl, —CONH—$(C_1\text{-}C_{12})$-alkyl, —CONH—$(C_3\text{-}C_{12})$-cycloalkyl, —CO—$(C_1\text{-}C_{12})$-alkyl, —CO—$(C_3\text{-}C_{12})$-cycloalkyl, —N—$[(C_1\text{-}C_{12})\text{-alkyl}]_2$, —COOH, —OH, —SH, —$SO_3H$, —CN, —$NH_2$, or a halogen;

X, Y, and Z are independently —O, —NH, —S, or —N—$(C_1\text{-}C_{30})$-alkyl;

$R_2$ is =O, —OH, —$SO_2$, —SO, or —$SOCH_3$;

$R_3$ on ring A is —$(C_1\text{-}C_{30})$-alkyl, —$(C_3\text{-}C_{12})$-cycloalkyl, —$(C_3\text{-}C_{12})$-heterocycloalkyl, —$(C_6\text{-}C_{20})$-aryl, —$(C_3\text{-}C_{20})$-heteroaryl, —O—$(C_1\text{-}C_{12})$-alkyl, —O—$(C_3\text{-}C_{12})$-cycloalkyl, —S—$(C_1\text{-}C_{12})$-alkyl, —S—$(C_3\text{-}C_{12})$-cycloalkyl, —COO—$(C_1\text{-}C_{12})$-alkyl, —COO—$(C_3\text{-}C_{12})$-cycloalkyl, —CONH—$(C_1\text{-}C_{12})$-alkyl, —CONH—$(C_3\text{-}C_{12})$-cycloalkyl, —CO—$(C_1\text{-}C_{12})$-alkyl, —CO—$(C_3\text{-}C_{12})$-cycloalkyl, —N—$[(C_1\text{-}C_{12})\text{-alkyl}]_2$, —$(C_6\text{-}C_{20})$-aryl-$(C_1\text{-}C_{12})$-alkyl, —$(C_3\text{-}C_{20})$-heteroaryl-$(C_1\text{-}C_{12})$-alkyl, —COOH, —OH, —SH, —$SO_3H$, —CN, —$NH_2$, or a halogen; and $R_3$ on ring C is hydrogen, —$(C_1\text{-}C_{30})$-alkyl, —$(C_3\text{-}C_{12})$-cycloalkyl, —$(C_3\text{-}C_{12})$-heterocycloalkyl, —N—$[(C_1\text{-}C_{12})\text{-alkyl}]_2$, —COOH, —OH, —SH, —$SO_3H$, —CN, —$NH_2$, or a halogen, wherein the compound, or the enantiomer, polymorph, or pharmaceutically acceptable salt thereof, is in an amount effective to increase a suppressive immune response in a subject in need thereof when administered to the subject.

15. A method of increasing an immune suppressive response in a subject in need thereof comprising administering to the subject the pharmaceutical composition of claim 14.

16. The method of claim 15, wherein the subject has an inflammatory disorder or disease, an autoimmune disorder or disease, chronic infection, transplant rejection, or graft-versus-host disease.

17. The method of claim 16, wherein the inflammatory disorder or disease is selected from the group consisting of rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopeni purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, obesity, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

18. The method of claim 16, wherein the autoimmune disorder or disease is selected from the group consisting of rheumatoid arthritis, systemic lupus erythematosus, alopecia areata, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Crohn's disease multiple sclerosis, and myasthenia gravis.

19. The method of claim 15, wherein the immune suppressive response is selected from the group consisting of an immune suppressive function of natural Treg (nTreg) and induction of conventional T cells into induced Treg (iTreg).

20. The method of claim 19, wherein the immune suppressive function of nTreg is the secretion of one or more anti-inflammatory cytokines.

21. The method of claim 20, wherein the one or more anti-inflammatory cytokines are IL10, TGFβ, or a combination thereof.

22. The method of claim 15, further comprising administering to the subject a second immunosuppressive agent.

23. The method of claim 22, wherein the second immunosuppressive agent is a compound selected from the group consisting of prednisone, budesonide, prednisolone, cyclosporine, tacrolimus, sirolimus, everolimus, azathioprine, leflunomide, mycophenolate, abatacept, adalimumab, anakinra, certolizumab, etanercept, golimumab, infliximab, ixekizumab, natalizumab, rituximab, secukinumab, tocilizumab, ustekinumab, vedolizumab, basiliximab, daclizumab, and muromonab.

24. The method of claim 15, wherein the compound, or the enantiomer, or pharmaceutically acceptable salt thereof in the pharmaceutical composition is administered in an amount effective to increase FoxP3 on immune cells.

25. The method of claim 24, wherein the immune cells comprise iTregs.

26. The method of claim 15, wherein the compound, or the enantiomer, or pharmaceutically acceptable salt thereof in the pharmaceutical composition is administered in an amount effective to increase proliferation of iTregs.

27. A method of increasing an immune suppressive response in subject in need thereof comprising contacting immune cells ex vivo with the pharmaceutical composition of claim 14 in an amount effective to increase expression of FoxP3 on the immune cells; and administering the contacted immune cells to the subject.

28. The method of claim 27, wherein the immune cells comprise autologous immune cells.

29. The method of claim 27, wherein the immune cells comprise T cells.

30. The method of claim 29, wherein the T cells comprise Tregs.

31. The method of claim 30, wherein the Tregs comprise iTregs.

32. A method for treating obesity in a subject in need thereof comprising administering to the subject the pharmaceutical composition of claim 14.

* * * * *